(12) United States Patent
Greiner et al.

(10) Patent No.: US 8,966,324 B2
(45) Date of Patent: Feb. 24, 2015

(54) TRANSACTIONAL EXECUTION BRANCH INDICATIONS

(75) Inventors: Dan F. Greiner, San Jose, CA (US); Christian Jacobi, Schoenaich (DE); Donald W. Schmidt, Stone Ridge, NY (US); Timothy J. Slegel, Staatsburg, NY (US)

(73) Assignee: International Business Machines Corporation, Armonk, NY (US)

( * ) Notice: Subject to any disclaimer, the term of this patent is extended or adjusted under 35 U.S.C. 154(b) by 167 days.

(21) Appl. No.: 13/524,779

(22) Filed: Jun. 15, 2012

(65) Prior Publication Data

US 2013/0339796 A1 Dec. 19, 2013

(51) Int. Cl.
*G06F 11/00* (2006.01)
(52) U.S. Cl.
USPC .............................................. 714/45; 712/234
(58) Field of Classification Search
CPC ............. G06F 11/3636; G06F 11/348; G06F 11/3466; G06F 11/3648; G06F 11/3476
USPC .............................................. 714/45; 712/234
See application file for complete search history.

(56) References Cited

U.S. PATENT DOCUMENTS

| | | | |
|---|---|---|---|
| 4,454,578 A | 6/1984 | Matsumoto et al. |
| 5,471,591 A | 11/1995 | Edmondson et al. |
| 5,504,900 A | 4/1996 | Raz |
| 5,551,013 A | 8/1996 | Beausoleil et al. |
| 5,574,873 A | 11/1996 | Davidian |
| 5,655,100 A | 8/1997 | Ebrahim et al. |
| 5,701,480 A | 12/1997 | Raz |
| 5,790,825 A | 8/1998 | Traut |
| 5,925,125 A | 7/1999 | Alpert et al. |
| 6,009,261 A | 12/1999 | Scalzi et al. |
| 6,035,313 A | 3/2000 | Marchant |
| 6,119,129 A | 9/2000 | Traversat et al. |
| 6,148,299 A | 11/2000 | Yoshimoto |
| 6,195,744 B1 | 2/2001 | Favor et al. |
| 6,237,089 B1 | 5/2001 | Moyer et al. |
| 6,308,255 B1 | 10/2001 | Gorishek, IV et al. |
| 6,463,582 B1 | 10/2002 | Lethin et al. |
| 6,615,304 B1 | 9/2003 | Ishizuka |

(Continued)

FOREIGN PATENT DOCUMENTS

EP 2239657 A1 10/2010
WO WO2007115003 A1 10/2007

OTHER PUBLICATIONS

Notice of Allowance for U.S. Appl. No. 13/524,788 dated Jul. 18, 2013, pp. 1-28.

(Continued)

*Primary Examiner* — Yolanda L Wilson
(74) *Attorney, Agent, or Firm* — William A. Kinnaman, Jr., Esq.; Blanche E. Schiller, Esq.; Heslin Rothenberg Farley & Mesiti P.C.

(57) ABSTRACT

Transactional execution branch indications are placed into one or more transaction diagnostic blocks when a transaction is aborted. Each branch indication specifies whether a branch was taken, as a result of executing a branch instruction within the transaction. As the transaction executes and a branch instruction is encountered, a branch indication is set in a vector indicating whether the branch was taken. Then, if the transaction aborts, the indicators are stored in one or more transaction diagnostic blocks providing a branch history usable in diagnosing the failure.

19 Claims, 24 Drawing Sheets

(56) References Cited

U.S. PATENT DOCUMENTS

| | | | |
|---|---|---|---|
| 6,658,578 | B1 | 12/2003 | Laurenti et al. |
| 6,738,892 | B1 | 5/2004 | Coon et al. |
| 6,754,809 | B1 | 6/2004 | Guttag et al. |
| 6,769,003 | B2 | 7/2004 | Park |
| 6,892,286 | B2 | 5/2005 | Hangal et al. |
| 6,963,919 | B1 | 11/2005 | Gary et al. |
| 7,055,070 | B1* | 5/2006 | Uhler et al. ............... 714/45 |
| 7,185,183 | B1 | 2/2007 | Uhler et al. |
| 7,185,234 | B1* | 2/2007 | Thekkath ............... 714/45 |
| 7,206,903 | B1 | 4/2007 | Moir et al. |
| 7,246,123 | B2 | 7/2007 | Carr et al. |
| 7,392,264 | B2 | 6/2008 | Lord et al. |
| 7,395,382 | B1 | 7/2008 | Moir |
| 7,398,355 | B1 | 7/2008 | Moir et al. |
| 7,421,544 | B1 | 9/2008 | Wright et al. |
| 7,496,726 | B1* | 2/2009 | Nussbaum et al. ............ 711/163 |
| 7,546,446 | B2 | 6/2009 | Henry et al. |
| 7,568,023 | B2 | 7/2009 | Green et al. |
| 7,617,421 | B2* | 11/2009 | Caprioli et al. ............... 714/49 |
| 7,634,638 | B1 | 12/2009 | Jensen et al. |
| 7,669,040 | B2 | 2/2010 | Dice |
| 7,707,394 | B2* | 4/2010 | Ashfield et al. ............... 712/227 |
| 7,779,232 | B2 | 8/2010 | Doing et al. |
| 7,814,378 | B2 | 10/2010 | Manovit et al. |
| 7,818,510 | B2 | 10/2010 | Tremblay et al. |
| 7,865,701 | B1 | 1/2011 | Tene et al. |
| 7,890,472 | B2 | 2/2011 | Magruder et al. |
| 7,904,434 | B2 | 3/2011 | Yalamanchi et al. |
| 7,908,456 | B2 | 3/2011 | Hertzberg et al. |
| 7,930,695 | B2 | 4/2011 | Chaudhry et al. |
| 7,966,459 | B2 | 6/2011 | Nussbaum et al. |
| 8,001,421 | B2 | 8/2011 | Wang et al. |
| 8,041,900 | B2 | 10/2011 | Caprioli et al. |
| 8,140,497 | B2 | 3/2012 | Goodman et al. |
| 8,161,016 | B2 | 4/2012 | Masuda |
| 8,161,273 | B2 | 4/2012 | Caprioli |
| 8,229,907 | B2 | 7/2012 | Gray et al. |
| 8,276,153 | B2 | 9/2012 | Horii et al. |
| 8,442,962 | B2 | 5/2013 | Lee et al. |
| 8,479,053 | B2 | 7/2013 | Rajwar et al. |
| 2002/0161815 | A1 | 10/2002 | Bischof et al. |
| 2002/0174162 | A1 | 11/2002 | Perks et al. |
| 2002/0174229 | A1 | 11/2002 | Owen et al. |
| 2003/0135844 | A1 | 7/2003 | Yellin et al. |
| 2004/0068501 | A1 | 4/2004 | McGoveran |
| 2004/0162967 | A1 | 8/2004 | Tremblay et al. |
| 2005/0015775 | A1 | 1/2005 | Russell et al. |
| 2006/0064508 | A1 | 3/2006 | Panwar et al. |
| 2006/0168199 | A1 | 7/2006 | Chagoly et al. |
| 2006/0212757 | A1 | 9/2006 | Ross et al. |
| 2007/0150509 | A1 | 6/2007 | Lev et al. |
| 2007/0162246 | A1 | 7/2007 | Barcia |
| 2007/0162520 | A1* | 7/2007 | Petersen et al. ............... 707/202 |
| 2007/0198781 | A1 | 8/2007 | Dice |
| 2007/0239915 | A1 | 10/2007 | Saha et al. |
| 2007/0260608 | A1 | 11/2007 | Hertzberg |
| 2007/0260942 | A1 | 11/2007 | Rajwar et al. |
| 2007/0288902 | A1 | 12/2007 | Lev et al. |
| 2007/0300013 | A1 | 12/2007 | Kitamura |
| 2008/0005504 | A1 | 1/2008 | Barnes |
| 2008/0016325 | A1 | 1/2008 | Laudon et al. |
| 2008/0059717 | A1 | 3/2008 | Saha et al. |
| 2008/0086516 | A1 | 4/2008 | Claborn et al. |
| 2008/0126764 | A1 | 5/2008 | Wu |
| 2008/0126883 | A1 | 5/2008 | Caprioli et al. |
| 2008/0162881 | A1 | 7/2008 | Welc et al. |
| 2008/0172550 | A1 | 7/2008 | Su et al. |
| 2008/0244544 | A1 | 10/2008 | Neelakantam et al. |
| 2008/0256074 | A1 | 10/2008 | Lev et al. |
| 2008/0288730 | A1 | 11/2008 | Heller et al. |
| 2008/0288819 | A1 | 11/2008 | Heller |
| 2008/0307267 | A1 | 12/2008 | Chandrasekaran |
| 2008/0320282 | A1 | 12/2008 | Morris |
| 2009/0007107 | A1 | 1/2009 | Taillefer et al. |
| 2009/0077135 | A1 | 3/2009 | Yalamanchi et al. |
| 2009/0106329 | A1 | 4/2009 | Masuda |
| 2009/0138890 | A1 | 5/2009 | Blake et al. |
| 2009/0171962 | A1 | 7/2009 | Taillefer |
| 2009/0172303 | A1 | 7/2009 | Welc |
| 2009/0172317 | A1 | 7/2009 | Saha et al. |
| 2009/0217098 | A1 | 8/2009 | Farrell et al. |
| 2009/0222822 | A1 | 9/2009 | Riemers |
| 2009/0260011 | A1 | 10/2009 | Snover et al. |
| 2009/0282405 | A1 | 11/2009 | Moir |
| 2010/0005316 | A1* | 1/2010 | LeGendre et al. ............ 713/189 |
| 2010/0023703 | A1 | 1/2010 | Christie et al. |
| 2010/0023706 | A1 | 1/2010 | Christie et al. |
| 2010/0023707 | A1 | 1/2010 | Hohmuth et al. |
| 2010/0088702 | A1 | 4/2010 | Dern et al. |
| 2010/0122041 | A1 | 5/2010 | Nakaike et al. |
| 2010/0138836 | A1 | 6/2010 | Dice et al. |
| 2010/0153776 | A1 | 6/2010 | Vick et al. |
| 2010/0162249 | A1 | 6/2010 | Shpeisman et al. |
| 2010/0162250 | A1 | 6/2010 | Adl-tabatabai |
| 2010/0169581 | A1 | 7/2010 | Sheaffer |
| 2010/0205608 | A1 | 8/2010 | Nemirovsky et al. |
| 2010/0217945 | A1 | 8/2010 | Ge et al. |
| 2010/0229043 | A1 | 9/2010 | Saha et al. |
| 2010/0235326 | A1 | 9/2010 | Fashchik et al. |
| 2010/0262955 | A1 | 10/2010 | Bedichek et al. |
| 2010/0332538 | A1 | 12/2010 | Gray et al. |
| 2010/0332807 | A1 | 12/2010 | Sheaffer et al. |
| 2010/0332901 | A1 | 12/2010 | Nussbaum et al. |
| 2010/0333096 | A1 | 12/2010 | Dice et al. |
| 2011/0016295 | A1 | 1/2011 | Catherwood et al. |
| 2011/0040956 | A1 | 2/2011 | Kissell |
| 2011/0041000 | A1 | 2/2011 | Li et al. |
| 2011/0041006 | A1 | 2/2011 | Fowler |
| 2011/0055837 | A1 | 3/2011 | Kumar et al. |
| 2011/0066831 | A1 | 3/2011 | Blundell et al. |
| 2011/0119528 | A1 | 5/2011 | Karlsson et al. |
| 2011/0145209 | A1 | 6/2011 | Kahn et al. |
| 2011/0145498 | A1 | 6/2011 | Taillefer et al. |
| 2011/0145512 | A1 | 6/2011 | Adl-Tabatabai et al. |
| 2011/0145637 | A1 | 6/2011 | Gray et al. |
| 2011/0153960 | A1 | 6/2011 | Rajwar et al. |
| 2011/0191545 | A1 | 8/2011 | Miller et al. |
| 2011/0208921 | A1 | 8/2011 | Pohlack et al. |
| 2011/0209151 | A1 | 8/2011 | Chung et al. |
| 2011/0209155 | A1 | 8/2011 | Giampapa et al. |
| 2011/0246993 | A1 | 10/2011 | Moir et al. |
| 2011/0252203 | A1 | 10/2011 | Kottapalli |
| 2011/0283096 | A1 | 11/2011 | Abernathy et al. |
| 2011/0296148 | A1 | 12/2011 | Cain, III et al. |
| 2011/0302143 | A1 | 12/2011 | Lomet |
| 2011/0307689 | A1 | 12/2011 | Chung et al. |
| 2011/0320420 | A1 | 12/2011 | Pardon et al. |
| 2012/0005461 | A1 | 1/2012 | Moir et al. |
| 2012/0030518 | A1* | 2/2012 | Rajwar et al. ............... 714/38.13 |
| 2012/0030521 | A1* | 2/2012 | Aranguren et al. ............ 714/45 |
| 2012/0079246 | A1 | 3/2012 | Breternitz, Jr. et al. |
| 2012/0101990 | A1 | 4/2012 | Holenstein et al. |

OTHER PUBLICATIONS

Office Action for U.S. Appl. No. 13/524,857 dated Jul. 22, 2013, pp. 1-29.
Notice of Allowance for U.S. Appl. No. 13/524,921 dated Jul. 22, 2013, pp. 1-27.
International Search Report and Written Opinion for PCT/EP2013/062173 dated Aug. 6, 2013, pp. 1-10.
Lev et al., "Debugging with Transactional Memory," Proceedings of the First ACM Sigplan Workshop on Languages, Compilers and Hardware Support for Transactional Computing, Jun. 2006, pp. 1-10.
Caprioli, Paul, "An Instruction Trace Recorder in a Processor Supporting Transactional Memory," Research Disclosure, vol. 543, No. 12, Jul. 2009, p. 756.
International Search Report and Written Opinion for PCT/EP2013/059205 dated Aug. 7, 2013, pp. 1-10.
Rosenberg, Jonathan B., "Chapter 9—Multithreaded Debugging," How Debuggers Work—Algorithms, Data Structures and Architecture, Jan. 1996, pp. 173-184.
International Search Report and Written Opinion for PCT/EP2013/062171 dated Aug. 9, 2013, pp. 1-10.

(56) References Cited

OTHER PUBLICATIONS

"Enterprise Systems Architecture/390-Principles of Operation (Ninth Edition)," IBM Publication No. SA22-7201-08, Jun. 2003, pp. 1-1028.
International Search Report and Written Opinion for PCT/EP2013/060348 dated Aug. 22, 2013, pp. 1-9.
International Search Report and Written Opinion for PCT/EP2013/060297 dated Sep. 6, 2013, pp. 1-11.
International Search Report and Written Opinion for PCT/EP2013/060373 dated Sep. 6, 2013, pp. 1-14.
Final Office Action for U.S. Appl. No. 13/524,898 dated Sep. 9, 2013, pp. 1-30.
International Search Report and Written Opinion for PCT/EP2013/060275 dated Sep. 10, 2013, pp. 1-11.
"z/Architecture Principles of Operation," IBM® Publication No. SA22-7832-08, Ninth Edition, Aug. 2010.
"Transactional Synchronization in Haswell—Blogs—Inte]® Software Network," http://software.intel.com/en-us/blogs/2012/02/07/transational-synchronization-in-haswell//, Feb. 7, 2012, pp. 1-5.
"Intel® Architecture Instruction Set Extensions Programming Reference," 319433-012A, Feb. 2012, pp. 1-1 thru 1-6.
Olszewski, Marek, "A Dynamic Instrumentation Approach to Software Transactional Memory," University of Toronto, 2007.
IBM TDB, "Optimization of Transaction Contexts in a Nested Object Model," http://www.ip.com/pubview/IPCOM000014568D; Aug. 2001.
IBM, "Method and System to Filter, Analyze and Statistics Transaction's Performance of Database," http://www.ip.com/pubview/IPCOM00015498D; Jul. 2007.
McDonald, A., et al. "Architectural Semantics for Practical Transactional Memory," Proceedings of the 33$^{rd}$ International Symposium on Computer Architecture (ISCA'06), SIGARCH Comput. Archit. News, May 2006, 34(2).
Minh, C.C. et al., "An Effective Hybrid Transactional Memory System with Strong Isolation Guarnatees," ISCA'07, SIGARCH Comput. Archit. News. 35(2), pp. 69-80, Jun. 2007.
Zilles et al., "Extending Hardware Transactional Memory to Support Non-busy Waiting and Non-transactional Actions," Transact First ACM SIGPLAN Workshop on Languages Compilers and Hardware Support for Transactional Computing, 2006, 10 pages.
Anonymous, "A Novel Squash and Recovery Mechanism in Transactional Memory System," IP.COM, IP.com No. IPCOM000196579D, pp. 1-2.
Abadi, M. et al., "Transactional Memory with Strong Atomicity Using Off-The-Shelf Memory Protection Hardware," PPoPP'09, Proceedings of the 14$^{th}$ ACM SIGPLAN Not. 44(4), pp. 185-196.
Manovit, C., et al., "Testing Implementations of Transactional Memory," In Proceedings of 15$^{th}$ International Conference of Parallel Architectures and Compilation Techniques (PACT '06), pp. 134-143, 2006.
Hangal, S., et al., "TSOtool: A Program for Verifying Memory Systems Using the Memory Consistency Model," Proceedings of the 31$^{th}$ Annual International Symposium on Computer Architecture (ISCA '04) pp. 1-10, Mar. 2004.
Etessami et al., "An Abort-Aware Model of Transactional Programming," In Proceedings of the 10$^{th}$ International Conference on Verification, Model Checking, and Abstract Interpretation (VMCAI '09), 2008.
Maessen, J-W., et al., "Store Atomicity for Transactional Memory, Electronic Notes in Theoretical Computer Science," 174(9), pp. 117-137, Jun. 2007.
Adl-Tabatabai, A-R. et al., "Compiler and Runtime Support for Efficient Software Transactional Memory," In Proceedings of the 2006 ACM SIGPLAN Conference on Programming Language Design and Implementation (PLDI '06), pp. 26-37, 2006.
Paxton, WH., et al., "A Client-Based Transaction System to Maintain Data Integrity," http://www.ip.com/pubview/IPCOM000128891D, Dec. 1980.
Cristian, F., et al., "Coordinator Log Transaction Execution Protocol," http://www.ip.com/pubview/IPCOM000100278D; Mar. 1990.
Lindsay, B., et al., "Presumed Abort Protocols," http://www.ip.com/pubview/IPCOM000047739D, Feb. 2005.
Greiner, Dan et al., "Transactional Processing," U.S. Appl. No. 13/524,921, filed Jun. 15, 2012, pp. 1-119.
Greiner, Dan et al., "Transactional Processing," U.S. Appl. No. 13/789,808, filed Mar. 8, 2013, pp. 1-118.
Greiner, Dan et al., "Transactional Diagnostic Block," U.S. Appl. No. 13/524,916, filed Jun. 15, 2012, pp. 1-116.
Greiner, Dan et al., "Transactional Diagnostic Block," U.S. Appl. No. 13/789,857, filed Mar. 8, 2013, pp. 1-112.
Greiner, Dan et al., "Program Event Recording Within a Transactional Environment," U.S. Appl. No. 13/524,903, filed Jun. 15, 2012, pp. 1-131.
Greiner, Dan et al., "Program Event Recording Within a Transactional Environment," U.S. Appl. No. 13/789,885, filed Mar. 8, 2013, pp. 1-128.
Greiner, Dan et al., "Transactional Execution Branch Indications," U.S. Appl. No. 13/783,366, filed Mar. 8, 2013, pp. 1-116.
Greiner, Dan et al., Selectively Controlling Instruction Execution in Transactional Processing, U.S. Appl. No. 13/524,898, filed Jun. 15, 2012, pp. 1-113.
Greiner, Dan et al., Selectively Controlling Instruction Execution in Transactional Processing, U.S. Appl. No. 13/789,307, filed Mar. 7, 2013, pp. 1-112.
Greiner, Dan et al., "Nontransactional Store Instruction," U.S. Appl. No. 13/524,887, filed Jun. 15, 2012, pp. 1-92.
Greiner, Dan et al., "Nontransactional Store Instruction," U.S. Appl. No. 13/783,359, filed Mar. 3, 2013, pp. 1-89.
Greiner, Dan et al., "Program Interruption Filtering in Transactional Execution," U.S. Appl. No. 13/524,839, filed Jun. 15, 2012, pp. 1-123.
Greiner, Dan et al., "Program Interruption Filtering in Transactional Execution," U.S. Appl. No. 13/789,963, filed Mar. 8, 2013, pp. 1-120.
Greiner, Dan et al., "Randomized Testing Within Transactional Execution," U.S. Appl. No. 13/524,796, filed Jun. 15, 2012, pp. 1-113.
Greiner, Dan et al., "Randomized Testing Within Transactional Execution," U.S. Appl. No. 13/783,357, filed Mar. 3, 2013, pp. 1-110.
Greiner, Dan et al., "Restricted Instructions in Transactional Execution," U.S. Appl. No. 13/524,765, filed Jun. 15, 2012, pp. 1-118.
Greiner, Dan et al., "Restricted Instructions in Transactional Execution," U.S. Appl. No. 13/783,572, filed Mar. 4, 2013, pp. 1-115.
Greiner, Dan et al., "Saving/Restoring Selected Registers in Transactional Processing," U.S. Appl. No. 13/524,882, filed Jun. 15, 2012, pp. 1-111.
Greiner, Dan et al., "Saving/Restoring Selected Registers in Transactional Processing," U.S. Appl. No. 13/783,353, filed Mar. 3, 2013, pp. 1-108.
Greiner, Dan et al., "Transaction Abort Instruction," U.S. Appl. No. 13/524,855, filed Jun. 15, 2012, pp. 1-108.
Greiner, Dan et al., "Transaction Abort Instruction," U.S. Appl. No. 13/789,999, filed Mar. 8, 2013, pp. 1-106.
Greiner, Dan et al., "Transaction Abort Processing," U.S. Appl. No. 13/524,877, filed Jun. 15, 2012, pp. 1-109.
Greiner, Dan et al., "Transaction Abort Processing," U.S. Appl. No. 13/790,020, filed Mar. 8, 2013, pp. 1-106.
Greiner, Dan et al., "Transaction Begin/End Instructions," U.S. Appl. No. 13/524,845, filed Jun. 15, 2012, pp. 1-119.
Greiner, Dan et al., "Transaction Begin/End Instructions," U.S. Appl. No. 13/789,219, filed Mar. 7, 2013, pp. 1-114.
Greiner, Dan et al., "Constrained Transaction Execution," U.S. Appl. No. 13/524,788, filed Jun. 15, 2012, pp. 1-104.
Greiner, Dan et al., "Constrained Transaction Execution," U.S. Appl. No. 13/783,327, filed Mar. 3, 2013, pp. 1-101.
Belmar, Brenton F. et al., "Facilitating Transaction Completion Subsequent to Repeated Aborts of the Transaction," U.S. Appl. No. 13/524,857, filed Jun. 15, 2012, pp. 1-126.
Belmar, Brenton F. et al., "Facilitating Transaction Completion Subsequent to Repeated Aborts of the Transaction," U.S. Appl. No. 13/783,316, filed Mar. 3, 2013, pp. 1-122.
Greiner, Dan et al., "Processor Assist Facility," U.S. Appl. No. 13/524,871, filed Jun. 15, 2012, pp. 1-123.

(56) References Cited

OTHER PUBLICATIONS

Greiner, Dan et al., "Processor Assist Facility," U.S. Appl. No. 13/789,183, filed May 7, 2013, pp. 1-120.
Alexander, Khary J., "Restricting Processing Within a Processor to Facilitate Transaction Completion," U.S. Appl. No. 13/524,833, filed Jun. 15, 2012, pp. 1- 125.
Alexander, Khary J., "Restricting Processing Within a Processor to Facilitate Transaction Completion," U.S. Appl. No. 13/788,919, filed Mar. 7, 2013, pp. 1-123.
Notice of Allowance for U.S. Appl. No. 13/524,845 dated Apr. 8, 2013, pp. 1-27.
International Search Report and Written Opinion for PCT/IB12/56622 dated Apr. 9, 2013, pp. 1-10.
Office Action for U.S. Appl. No. 13/524,898 dated Apr. 24, 2013, pp. 1-29.
International Search Report and Written Opinion for PCT/IB12/56733 dated May 21, 2013, pp. 1-7.
International Search Report and Written Opinion for PCT/IB12/56734 dated May 10, 2013, pp. 1-7.
International Search Report and Written Opinion for PCT/IB12/56735 dated May 20, 2013, pp. 1-7.
Office Action for U.S. Appl. No. 13/524,788 dated Mar. 6, 2013, pp. 1-22.
Office Action for U.S. Appl. No. 13/524,921 dated Mar. 11, 2013, pp. 1-23.
International Search Report and Written Opinion for PCT/IB2012/056625 dated Mar. 19, 2013, pp. 1-6.
Anonymous, "A Novel Squash and Recovery Mechanism in Transactional Memory System," IP.COM, IP.com No. IPCOM000196579D, Jun. 2010, pp. 1-3.
Final Office Action for U.S. Appl. No. 13/524,857 dated Dec. 13, 2013, pp. 1-16.
International Search Report and Written Opinion for PCT/IB2013/054813 dated Jan. 30, 2014, pp. 1-10.
Office Action for U.S. Appl. No. 13,524,916 dated Feb. 27, 2014, pp. 1-26.
Office Action for U.S. Appl. No. 13/789,857 dated Feb. 27, 2014, pp. 1-23.
Office Action for U.S. Appl. No. 13/783,366 dated Mar. 4, 2014, pp. 1-26.
Office Action for U.S. Appl. No. 13/789,307 dated Apr. 3, 2014, pp. 1-32.
Office Action for U.S. Appl. No. 13/783,316 dated Apr. 4, 2014, pp. 1-29.
Office Action for U.S. Appl. No. 13/783,327 dated Apr. 8, 2014, pp. 1-35.
International Search Report and Written Opinion for PCT/IB2013/054812 dated Mar. 28, 2014, pp. 1-10.
Christie, Dave et al., "Evaluation of AMD's Advanced Synchronization Facility Within a Complete Transactional Memory Stack," EuroSys'10, Apr. 2010, pp. 27-40.
Jacobi, Christian et al., "Transactional Memory Architecture and Implementation for IBM System z," MICRO-45 Proceedings of the 2012 45th Annual IEEE/ACM International Symposium on Microarchitecture, Dec. 2012, pp. 25-36.
Office Action for U.S. Appl. No. 13/789,808 dated Apr. 28, 2014, pp. 1-34.
Office Action for U.S. Appl. No. 13/789,219 dated May 15, 2014, pp. 1-33.
Notice of Allowance for U.S. Appl. No. 13/790,020 dated Jul. 21, 2014, 34 pages.
Notice of Allowance for U.S. Appl. No. 13/789,307 dated Aug. 11, 2014, 17 pages.
Notice of Allowance for U.S. Appl. No. 13/783,316 dated Sep. 17, 2014, 19 pages.
Notice of Allowance for U.S. Appl. No. 13/524,857 dated Sep. 17, 2014, 26 pages.

* cited by examiner

| CODE | REASON FOR ABORT | CC SET |
|---|---|---|
| 2 | EXTERNAL INTERRUPTION | 2 |
| 4 | PROGRAM INTERRUPTION (UNFILTERED) | 2 OR 3 + |
| 5 | MACHINE - CHECK INTERRUPTION | 2 |
| 6 | I/O INTERRUPTION | 2 |
| 7 | FETCH OVERFLOW | 2 OR 3 |
| 8 | STORE OVERFLOW | 2 OR 3 |
| 9 | FETCH CONFLICT | 2 |
| 10 | STORE CONFLICT | 2 |
| 11 | RESTRICTED INSTRUCTION | 3 |
| 12 | PROGRAM EXCEPTION CONDITION (FILTERED) | 3 |
| 13 | NESTING DEPTH EXCEEDED | 3 |
| 14 | CACHE FETCH RELATED | 2 OR 3 |
| 15 | CACHE STORE RELATED | 2 OR 3 |
| 16 | CACHE OTHER | 2 OR 3 |
| 255 | MISCELLANEOUS CONDITION | 2 OR 3 |
| >255 | TABORT INSTRUCTION | 2 OR 3 |
| ‡ | CANNOT BE DETERMINED; NO TDB STORED | 1 |

EXPLANATION:
+ CONDITION CODE IS BASED ON INTERRUPTION CODE

‡ THIS SITUATION OCCURS WHEN A TRANSACTION ABORTS, BUT THE TDB HAS BECOME INACCESSIBLE SUBSEQUENT TO THE SUCCESSFUL EXECUTION OF THE OUTERMOST TBEGIN INSTRUCTION. NO TBEGIN SPECIFIED TDB IS STORED, AND THE CONDITION CODE IS SET TO 1.

FIG. 10

TRANSACTIONAL EXECUTION BRANCH INDICATIONS

BACKGROUND

One or more aspects relate, in general, to multiprocessing computing environments, and in particular, to transactional processing within such computing environments.

An enduring challenge in multiprocessor programming is that of updates to the same storage location by multiple central processing units (CPUs). Many instructions that update storage locations, including even simple logical operations, such as AND, do so with multiple accesses to the location. For instance, first, the storage location is fetched, and then, the updated result is stored back.

In order for multiple CPUs to safely update the same storage location, access to the location is serialized. One instruction, the TEST AND SET instruction, introduced with the S/360 architecture formerly offered by International Business Machines Corporation, provided an interlocked update of a storage location. Interlocked update means that, as observed by other CPUs and the input/output (I/O) subsystem (e.g., channel subsystem), the entire storage access of the instruction appears to occur atomically. Later, the S/370 architecture offered by International Business Machines Corporation introduced the COMPARE AND SWAP and COMPARE DOUBLE AND SWAP instructions that provide a more sophisticated means of performing interlocked update, and allow the implementation of what is commonly known as a lock word (or semaphore). Recently added instructions have provided additional interlocked-update capabilities, including COMPARE AND SWAP AND PURGE, and COMPARE AND SWAP AND STORE. However, all of these instructions provide interlocking for only a single storage location.

More complex program techniques may require the interlocked update of multiple storage locations, such as when adding an element to a doubly-linked list. In such an operation, both a forward and backward pointer are to appear to be simultaneously updated, as observed by other CPUs and the I/O subsystem. In order to effect such a multiple location update, the program is forced to use a separate, single point of serialization, such as a lock word. However, lock words may provide a much courser level of serialization than is warranted; for example, the lock words may serialize an entire queue of millions of elements, even though only two elements are being updated. The program may structure the data to use finer-grained serialization (e.g., a hierarchy of lock points), but that introduces additional problems, such as potential deadlock situations if the hierarchy is violated, and recovery issues if the program encounters an error while holding one or more locks or if the lock cannot be acquired.

In addition to the above, there are numerous scenarios where a program may execute a sequence of instructions that may or may not result in an exception condition. If no exception condition occurs, then the program continues; however, if an exception is recognized, then the program may take corrective action to eliminate the exception condition. Java, as one example, can exploit such execution in, for instance, speculative execution, partial in-lining of a function, and/or in the re-sequencing of pointer null checking.

In classic operating system environments, such as z/OS and its predecessors offered by International Business Machines Corporation, the program establishes a recovery environment to intercept any program-exception condition that it may encounter. If the program does not intercept the exception, the operating system typically abnormally terminates the program for exceptions that the operating system is not prepared to handle. Establishing and exploiting such an environment is costly and complicated.

BRIEF SUMMARY

Shortcomings of the prior art are overcome and advantages are provided through the provision of a computer program product for providing diagnostic information on transaction aborts. The computer program product includes a computer readable storage medium readable by a processing circuit and storing instructions for execution by the processing circuit for performing a method. The method includes, for instance, executing a transaction, the transaction effectively delaying committing transactional stores to main memory until completion of a selected transaction; based on executing the transaction, determining whether the transaction includes one or more branching instructions; based on determining the transaction includes one or more branching instructions, setting one or more indicators corresponding to the one or more branching instructions, wherein an indicator indicates whether a branch was taken; determining that the transaction has aborted; and based on determining the transaction has aborted, storing the one or more indicators in a transaction diagnostic block (TDB) associated with the transaction.

Methods and systems relating to one or more embodiments are also described and claimed herein. Further, services relating to one or more embodiments are also described and may be claimed herein.

Additional features and advantages are realized through. Other embodiments and aspects are described in detail herein and are considered a part of the claimed invention.

BRIEF DESCRIPTION OF THE SEVERAL VIEWS OF THE DRAWINGS

One or more aspects are particularly pointed out and distinctly claimed as examples in the claims at the conclusion of the specification. The foregoing and other objects, features, and advantages are apparent from the following detailed description taken in conjunction with the accompanying drawings in which:

FIG. 10 depicts example reasons for abort, along with associated abort codes and condition codes;

DETAILED DESCRIPTION

Figure 1:
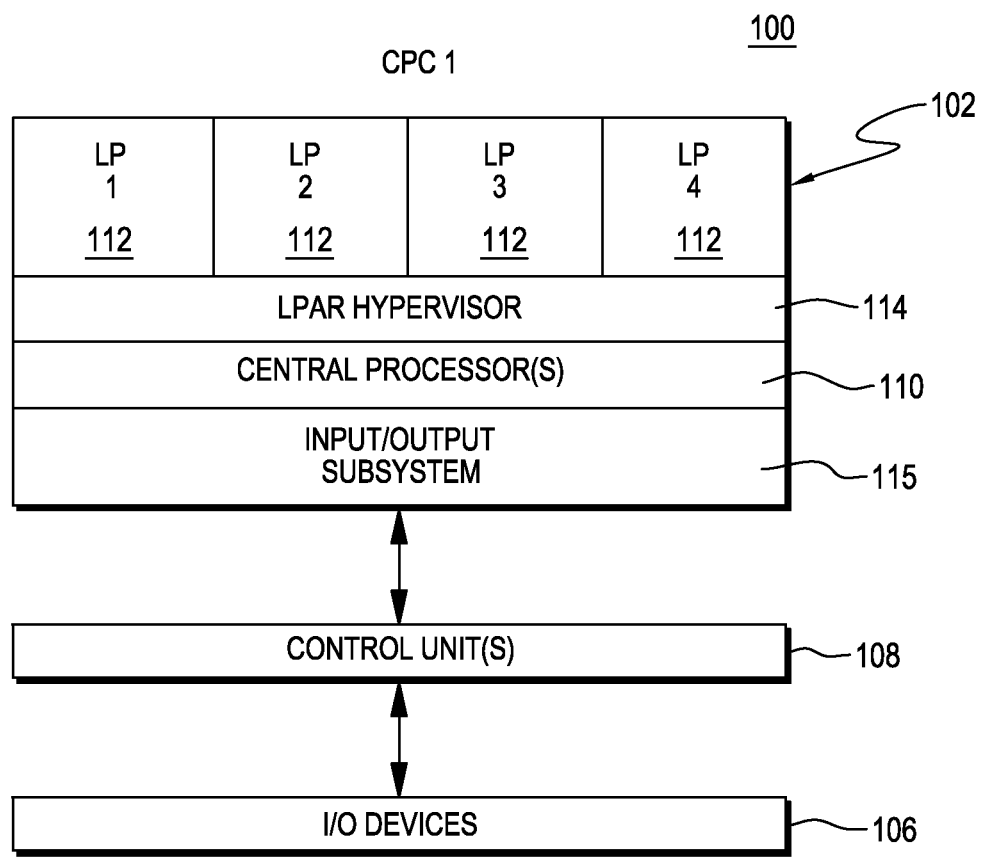
FIG. 1 depicts one embodiment of a computing environment.

In accordance with one aspect, a transactional execution (TX) facility is provided. This facility provides transactional processing for instructions, and in one or more embodiments, offers different execution modes, as described below, as well as nested levels of transactional processing.

The transactional execution facility introduces a CPU state called the transactional execution (TX) mode. Following a CPU reset, the CPU is not in the TX mode. The CPU enters the TX mode by a TRANSACTION BEGIN instruction. The CPU leaves the TX mode by either (a) an outermost TRANSACTION END instruction (more details on inner and outer to follow), or (b) the transaction being aborted. While in the TX mode, storage accesses by the CPU appear to be block-concurrent as observed by other CPUs and the I/O subsystem. The storage accesses are either (a) committed to storage when the outermost transaction ends without aborting (i.e., e.g., updates made in a cache or buffer local to the CPU are propagated and stored in real memory and visible to other CPUs), or (b) discarded if the transaction is aborted.

Transactions may be nested. That is, while the CPU is in the TX mode, it may execute another TRANSACTION BEGIN instruction. The instruction that causes the CPU to enter the TX mode is called the outermost TRANSACTION BEGIN; similarly, the program is said to be in the outermost transaction. Subsequent executions of TRANSACTION BEGIN are called inner instructions; and the program is executing an inner transaction. The model provides a minimum nesting depth and a model-dependent maximum nesting depth. An EXTRACT TRANSACTION NESTING DEPTH instruction returns the current nesting depth value, and in a further embodiment, may return a maximum nesting-depth value. This technique uses a model called "flattened nesting" in which an aborting condition at any nesting depth causes all levels of the transaction to be aborted, and control is returned to the instruction following the outermost TRANSACTION BEGIN.

During processing of a transaction, a transactional access made by one CPU is said to conflict with either (a) a transactional access or nontransactional access made by another CPU, or (b) a nontransactional access made by the I/O subsystem, if both accesses are to any location within the same cache line, and one or both of the accesses is a store. In other words, in order for transactional execution to be productive, the CPU is not to be observed making transactional accesses until it commits. This programming model may be highly effective in certain environments; for example, the updating of two points in a doubly-linked list of a million elements. However, it may be less effective, if there is a lot of contention for the storage locations that are being transactionally accessed.

In one model of transactional execution (referred to herein as a nonconstrained transaction), when a transaction is aborted, the program may either attempt to re-drive the transaction in the hopes that the aborting condition is no longer present, or the program may "fall back" to an equivalent non-transactional path. In another model of transactional execution (referred to herein as a constrained transaction), an aborted transaction is automatically re-driven by the CPU; in the absence of constraint violations, the constrained transaction is assured of eventual completion.

When initiating a transaction, the program can specify various controls, such as (a) which general registers are restored to their original contents if the transaction is aborted, (b) whether the transaction is allowed to modify the floating-point-register context, including, for instance, floating point registers and the floating point control register, (c) whether the transaction is allowed to modify access registers (ARs), and (d) whether certain program-exception conditions are to be blocked from causing an interruption. If a nonconstrained transaction is aborted, various diagnostic information may be provided. For instance, the outermost TBEGIN instruction that initiates a nonconstrained transaction may designate a program specified transaction diagnostic block (TDB). Further, the TDB in the CPU's prefix area or designated by the host's state description may also be used if the transaction is aborted due to a program interruption or a condition that causes interpretative execution to end, respectively.

Indicated above are various types of registers. These are further explained in detail herein. General registers may be used as accumulators in general arithmetic and logical operations. In one embodiment, each register contains 64 bit positions, and there are 16 general registers. The general registers are identified by the numbers 0-15, and are designated by a four-bit R field in an instruction. Some instructions provide for addressing multiple general registers by having several R fields. For some instructions, the use of a specific general register is implied rather than explicitly designated by an R field of the instruction.

In addition to their use as accumulators in general arithmetic and logical operations, 15 of the 16 general registers are also used as base address and index registers in address generation. In these cases, the registers are designated by a four-bit B field or X field in an instruction. A value of zero in the B or X field specifies that no base or index is to be applied, and thus, general register 0 is not to be designated as containing a base address or index.

Floating point instructions use a set of floating point registers. The CPU has 16 floating point registers, in one embodiment. The floating point registers are identified by the numbers 0-15, and are designated by a four bit R field in floating point instructions. Each floating point register is 64 bits long and can contain either a short (32-bit) or a long (64-bit) floating point operand.

A floating point control (FPC) register is a 32-bit register that contains mask bits, flag bits, a data exception code, and rounding mode bits, and is used during processing of floating point operations.

Further, in one embodiment, the CPU has 16 control registers, each having 64 bit positions. The bit positions in the registers are assigned to particular facilities in the system, such as Program Event Recording (PER) (discussed below), and are used either to specify that an operation can take place or to furnish special information required by the facility. In one embodiment, for the transactional facility, CR0 (bits 8 and 9) and CR2 (bits 61-63) are used, as described below.

The CPU has, for instance, 16 access registers numbered 0-15. An access register consists of 32 bit positions containing an indirect specification of an address space control element (ASCE). An address space control element is a parameter used by the dynamic address translation (DAT) mechanism to translate references to a corresponding address space. When the CPU is in a mode called the access register mode (controlled by bits in the program status word (PSW)), an instruction B field, used to specify a logical address for a storage operand reference, designates an access register, and the address space control element specified by the access register is used by DAT for the reference being made. For some instructions, an R field is used instead of a B field. Instructions are provided for loading and storing the contents of the access registers and for moving the contents of one access register to another.

Each of access registers 1-15 can designate any address space. Access register 0 designates the primary instruction space. When one of access registers 1-15 is used to designate an address space, the CPU determines which address space is designated by translating the contents of the access register. When access register 0 is used to designate an address space, the CPU treats the access register as designating the primary instruction space, and it does not examine the actual contents of the access register. Therefore, the 16 access registers can designate, at any one time, the primary instruction space and a maximum of 15 other spaces.

In one embodiment, there are multiple types of address spaces. An address space is a consecutive sequence of integer numbers (virtual addresses), together with the specific transformation parameters which allow each number to be associated with a byte location in storage. The sequence starts at zero and proceeds left to right.

In, for instance, the z/Architecture, when a virtual address is used by a CPU to access main storage (a.k.a., main memory), it is first converted, by means of dynamic address translation (DAT), to a real address, and then, by means of prefixing, to an absolute address. DAT may use from one to five levels of tables (page, segment, region third, region second, and region first) as transformation parameters. The designation (origin and length) of the highest-level table for a specific address space is called an address space control element, and it is found for use by DAT in a control register or as specified by an access register. Alternatively, the address space control element for an address space may be a real space designation, which indicates that DAT is to translate the virtual address simply by treating it as a real address and without using any tables.

DAT uses, at different times, the address space control elements in different control registers or specified by the access registers. The choice is determined by the translation mode specified in the current PSW. Four translation modes are available: primary space mode, secondary space mode, access register mode and home space mode. Different address spaces are addressable depending on the translation mode.

At any instant when the CPU is in the primary space mode or secondary space mode, the CPU can translate virtual addresses belonging to two address spaces—the primary address space and the second address space. At any instant when the CPU is in the access register mode, it can translate virtual addresses of up to 16 address spaces—the primary address space and up to 15 AR-specified address spaces. At any instant when the CPU is in the home space mode, it can translate virtual addresses of the home address space.

The primary address space is identified as such because it consists of primary virtual addresses, which are translated by means of the primary address space control element (ASCE). Similarly, the secondary address space consists of secondary virtual addresses translated by means of the secondary ASCE; the AR specified address spaces consist of AR specified virtual addresses translated by means of AR specified ASCEs; and the home address space consists of home virtual addresses translated by means of the home ASCE. The primary and secondary ASCEs are in control registers 1 and 7, respectively. AR specified ASCEs are in ASN-second-table entries that are located through a process called access-register translation (ART) using control registers 2, 5 and 8. The home ASCE is in control register 13.

One embodiment of a computing environment to incorporate and use one or more aspects of the transactional facility described herein is described with reference to FIG. 1.

Referring to FIG. 1, in one example, computing environment 100 is based on the z/Architecture, offered by International Business Machines (IBM®) Corporation, Armonk, N.Y. The z/Architecture is described in an IBM Publication entitled "z/Architecture—Principles of Operation," Publication No. SA22-7932-08, $9^{th}$ Edition, August 2010, which is hereby incorporated herein by reference in its entirety.

Z/ARCHITECTURE, IBM, and Z/OS and Z/VM (referenced below) are registered trademarks of International Business Machines Corporation, Armonk, N.Y. Other names used herein may be registered trademarks, trademarks or product names of International Business Machines Corporation or other companies.

As one example, computing environment 100 includes a central processor complex (CPC) 102 coupled to one or more input/output (I/O) devices 106 via one or more control units 108. Central processor complex 102 includes, for instance, one or more central processors 110, one or more partitions 112 (e.g., logical partitions (LP)), a logical partition hypervisor 114, and an input/output subsystem 115, each of which is described below.

Central processors 110 are physical processor resources allocated to the logical partitions. In particular, each logical partition 112 has one or more logical processors, each of which represents all or a share of a physical processor 110 allocated to the partition. The logical processors of a particular partition 112 may be either dedicated to the partition, so that the underlying processor resource 110 is reserved for that partition; or shared with another partition, so that the underlying processor resource is potentially available to another partition.

A logical partition functions as a separate system and has one or more applications, and optionally, a resident operating system therein, which may differ for each logical partition. In one embodiment, the operating system is the z/OS operating system, the z/VM operating system, the z/Linux operating system, or the TPF operating system, offered by International Business Machines Corporation, Armonk, N.Y.

Logical partitions 112 are managed by a logical partition hypervisor 114, which is implemented by firmware running on processors 110. As used herein, firmware includes, e.g., the microcode and/or millicode of the processor. It includes, for instance, the hardware-level instructions and/or data structures used in implementation of higher level machine code. In one embodiment, it includes, for instance, proprietary code that is typically delivered as microcode that includes trusted software or microcode specific to the underlying hardware and controls operating system access to the system hardware.

The logical partitions and logical partition hypervisor each comprise one or more programs residing in respective partitions of central storage associated with the central processors. One example of logical partition hypervisor 114 is the Processor Resource/System Manager (PR/SM), offered by International Business Machines Corporation, Armonk, N.Y.

Input/output subsystem 115 directs the flow of information between input/output devices 106 and main storage (a.k.a., main memory). It is coupled to the central processing complex, in that it can be a part of the central processing complex or separate therefrom. The I/O subsystem relieves the central processors of the task of communicating directly with the input/output devices and permits data processing to proceed concurrently with input/output processing. To provide communications, the I/O subsystem employs I/O communications adapters. There are various types of communications adapters including, for instance, channels, I/O adapters, PCI cards, Ethernet cards, Small Computer Storage Interface (SCSI) cards, etc. In the particular example described herein, the I/O communications adapters are channels, and therefore, the I/O subsystem is referred to herein as a channel subsystem. However, this is only one example. Other types of I/O subsystems can be used.

The I/O subsystem uses one or more input/output paths as communication links in managing the flow of information to or from input/output devices 106. In this particular example, these paths are called channel paths, since the communication adapters are channels.

The computing environment described above is only one example of a computing environment that can be used. Other environments, including but not limited to, non-partitioned environments, other partitioned environments, and/or emulated environments, may be used; embodiments are not limited to any one environment.

In accordance with one or more aspects, the transactional execution facility is a CPU enhancement that provides the means by which the CPU can execute a sequence of instructions—known as a transaction—that may access multiple storage locations, including the updating of those locations. As observed by other CPUs and the I/O subsystem, the transaction is either (a) completed in its entirety as a single atomic operation, or (b) aborted, potentially leaving no evidence that it ever executed (except for certain conditions described herein). Thus, a successfully completed transaction can update numerous storage locations without any special locking that is needed in the classic multiprocessing model.

The transactional execution facility includes, for instance, one or more controls; one or more instructions; transactional processing, including constrained and nonconstrained execution; and abort processing, each of which is further described below.

In one embodiment, three special purpose controls, including a transaction abort Program Status Word (PSW), a transaction diagnostic block (TDB) address, and a transaction nesting depth; five control register bits; and six general instructions, including TRANSACTION BEGIN (constrained and nonconstrained), TRANSACTION END, EXTRACT TRANSACTION NESTING DEPTH, TRANSACTION ABORT, and NONTRANSACTIONAL STORE, are used to control the transactional execution facility. When the facility is installed, it is installed, for instance, in all CPUs in the configuration. A facility indication, bit 73 in one implementation, when one, indicates that the transactional execution facility is installed.

When the transactional execution facility is installed, the configuration provides a nonconstrained transactional execution facility, and optionally, a constrained transactional execution facility, each of which is described below. When facility indications 50 and 73, as examples, are both one, the constrained transactional execution facility is installed. Both facility indications are stored in memory at specified locations.

As used herein, the instruction name TRANSACTION BEGIN refers to the instructions having the mnemonics TBEGIN (Transaction Begin for a nonconstrained transaction) and TBEGINC (Transaction Begin for a constrained transaction). Discussions pertaining to a specific instruction are indicated by the instruction name followed by the mnemonic in parentheses or brackets, or simply by the mnemonic.

Figure 2A:
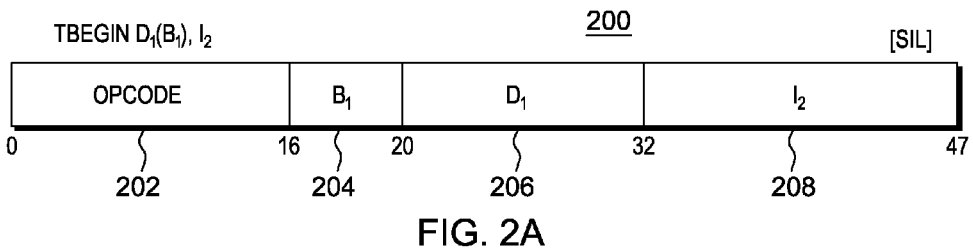
FIG. 2A depicts one example of a Transaction Begin (TBEGIN) instruction.
Figure 2B:
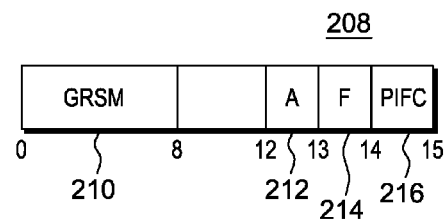
FIG. 2B depicts one embodiment of further details of a field of the TBEGIN instruction of FIG. 2A.

One embodiment of a format of a TRANSACTION BEGIN (TBEGIN) instruction is depicted in FIGS. 2A-2B. As one example, a TBEGIN instruction 200 includes an opcode field 202 that includes an opcode specifying a transaction begin nonconstrained operation; a base field ($B_1$) 204; a displacement field ($D_1$) 206; and an immediate field ($I_2$) 208. When the $B_1$ field is nonzero, the contents of the general register specified by $B_1$ 204 are added to $D_1$ 206 to obtain the first operand address.

When the $B_1$ field is nonzero, the following applies:
When the transaction nesting depth is initially zero, the first operand address designates the location of the 256 byte transaction diagnostic block, called the TBEGIN-specified TDB (described further below) into which various diagnostic information may be stored if the transaction is aborted. When the CPU is in the primary space mode or access register mode, the first operand address designates a location in the primary address space. When the CPU is in the secondary space or home space mode, the first operand address designates a location in the secondary or home address space, respectively. When DAT is off, the transaction diagnostic block (TDB) address (TDBA) designates a location in real storage.

Store accessibility to the first operand is determined. If accessible, the logical address of the operand is placed into the transaction diagnostic block address (TDBA), and the TDBA is valid.
When the CPU is already in the nonconstrained transactional execution mode, the TDBA is not modified, and it is unpredictable whether the first operand is tested for accessibility.

When the $B_1$ field is zero, no access exceptions are detected for the first operand and, for the outermost TBEGIN instruction, the TDBA is invalid.

The bits of the $I_2$ field are defined as follows, in one example:
General Register Save Mask (GRSM) 210 (FIG. 2B):
Bits 0-7 of the $I_2$ field contain the general register save mask (GRSM). Each bit of the GRSM represents an even-odd pair of general registers, where bit 0 represents registers 0 and 1, bit 1 represents registers 2 and 3, and so forth. When a bit in the GRSM of the outermost TBEGIN instruction is zero, the corresponding register pair is not saved. When a bit in the GRSM of the outermost TBEGIN instruction is one, the corresponding register pair is saved in a model dependent location that is not directly accessible by the program.

If the transaction aborts, saved register pairs are restored to their contents when the outermost TBEGIN instruction was executed. The contents of all other (unsaved) general registers are not restored when a transaction aborts.

The general register save mask is ignored on all TBEGINs except for the outermost one.

Allow AR Modification (A) 212:

The A control, bit 12 of the $I_2$ field, controls whether the transaction is allowed to modify an access register. The effective allow AR modification control is the logical AND of the A control in the TBEGIN instruction for the current nesting level and for all outer levels.

If the effective A control is zero, the transaction will be aborted with abort code 11 (restricted instruction) if an attempt is made to modify any access register. If the effective A control is one, the transaction will not be aborted if an access register is modified (absent of any other abort condition).

Allow Floating Point Operation (F) 214:

The F control, bit 13 of the $I_2$ field, controls whether the transaction is allowed to execute specified floating point instructions. The effective allow floating point operation control is the logical AND of the F control in the TBEGIN instruction for the current nesting level and for all outer levels.

If the effective F control is zero, then (a) the transaction will be aborted with abort code 11 (restricted instruction) if an attempt is made to execute a floating point instruction, and (b) the data exception code (DXC) in byte 2 of the floating point control register (FPCR) will not be set by any data exception program exception condition. If the effective F control is one, then (a) the transaction will not be aborted if an attempt is made to execute a floating point instruction (absent any other abort condition), and (b) the DXC in the FPCR may be set by a data exception program exception condition.

Program Interruption Filtering Control (PIFC) 216:

Bits 14-15 of the $I_2$ field are the program interruption filtering control (PIFC). The PIFC controls whether certain classes of program exception conditions (e.g., addressing exception, data exception, operation exception, protection exception, etc.) that occur while the CPU is in the transactional execution mode result in an interruption.

The effective PIFC is the highest value of the PIFC in the TBEGIN instruction for the current nesting level and for all outer levels. When the effective PIFC is zero, all program exception conditions result in an interruption. When the effective PIFC is one, program exception conditions having a transactional execution class of 1 and 2 result in an interruption. (Each program exception condition is assigned at least one transactional execution class, depending on the severity of the exception. Severity is based on the likelihood of recovery during a repeated execution of the transactional execution, and whether the operating system needs to see the interruption.) When the effective PIFC is two, program exception conditions having a transactional execution class of 1 result in an interruption. A PIFC of 3 is reserved.

Bits 8-11 of the $I_2$ field (bits 40-43 of the instruction) are reserved and should contain zeros; otherwise, the program may not operate compatibly in the future.

Figure 3A:
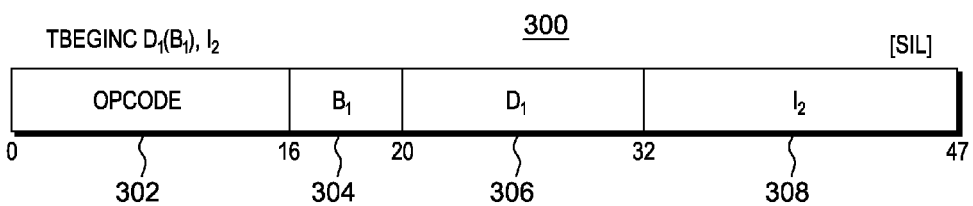
FIG. 3A depicts on example of a Transaction Begin constrained (TBEGINC) instruction.

One embodiment of a format of a Transaction Begin constrained (TBEGINC) instruction is described with reference to FIGS. 3A-3B. In one example, TBEGINC 300 includes an opcode field 302 that includes an opcode specifying a transaction begin constrained operation; a base field ($B_1$) 304; a displacement field ($D_1$) 306; and an immediate field ($I_2$) 308. The contents of the general register specified by $B_1$ 304 are added to $D_1$ 306 to obtain the first operand address. However, with the transaction begin constrained instruction, the first operand address is not used to access storage. Instead, the $B_1$ field of the instruction includes zeros; otherwise, a specification exception is recognized.

Figure 3B:
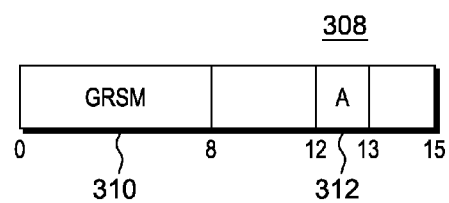
FIG. 3B depicts one embodiment of further details of a field of the TBEGINC instruction of FIG. 3A.

In one embodiment, the $I_2$ field includes various controls, an example of which is depicted in FIG. 3B.

The bits of the $I_2$ field are defined as follows, in one example:

General Register Save Mask (GRSM) 310:

Bits 0-7 of the $I_2$ field contain the general register save mask (GRSM). Each bit of the GRSM represents an even-odd pair of general registers, where bit 0 represents registers 0 and 1, bit 1 represents registers 2 and 3, and so forth. When a bit in the GRSM is zero, the corresponding register pair is not saved. When a bit in the GRSM is one, the corresponding register pair is saved in a model-dependent location that is not directly accessible by the program.

If the transaction aborts, saved register pairs are restored to their contents when the outermost TRANSACTION BEGIN instruction was executed. The contents of all other (unsaved) general registers are not restored when a constrained transaction aborts.

When TBEGINC is used to continue execution in the non-constrained transaction execution mode, the general register save mask is ignored.

Allow AR Modification (A) 312:

The A control, bit 12 of the $I_2$ field, controls whether the transaction is allowed to modify an access register. The effective allow-AR-modification control is the logical AND of the A control in the TBEGINC instruction for the current nesting level and for any outer TBEGIN or TBEGINC instructions.

If the effective A control is zero, the transaction will be aborted with abort code 11 (restricted instruction) if an attempt is made to modify any access register. If the effective A control is one, the transaction will not be aborted if an access register is modified (absent of any other abort condition).

Bits 8-11 and 13-15 of the $I_2$ field (bits 40-43 and 45-47 of the instruction) are reserved and should contain zeros.

Figure 4:
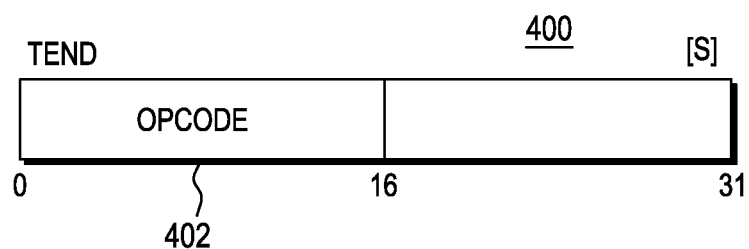
FIG. 4 depicts one example of a Transaction End (TEND) instruction.

The end of a Transaction Begin instruction is specified by a TRANSACTION END (TEND) instruction, a format of which is depicted in FIG. 4. As one example, a TEND instruction 400 includes an opcode field 402 that includes an opcode specifying a transaction end operation.

A number of terms are used with respect to the transactional execution facility, and therefore, solely for convenience, a list of terms is provided below in alphabetical order. In one embodiment, these terms have the following definition:

Abort: A transaction aborts when it is ended prior to a TRANSACTION END instruction that results in a transaction nesting depth of zero. When a transaction aborts, the following occurs, in one embodiment:

Transactional store accesses made by any and all levels of the transaction are discarded (that is, not committed).

Non-transactional store accesses made by any and all levels of the transaction are committed.

Registers designated by the general register save mask (GRSM) of the outermost TRANSACTION BEGIN instruction are restored to their contents prior to the transactional execution (that is, to their contents at execution of the outermost TRANSACTION BEGIN instruction). General registers not designated by the general register save mask of the outermost TRANSACTION BEGIN instruction are not restored.

Access registers, floating-point registers, and the floating-point control register are not restored. Any changes made to these registers during transaction execution are retained when the transaction aborts.

A transaction may be aborted due to a variety of reasons, including attempted execution of a restricted instruction, attempted modification of a restricted resource, transactional conflict, exceeding various CPU resources, any interpretive-execution interception condition, any interruption, a TRANSACTION ABORT instruction, and other reasons. A transaction-abort code provides specific reasons why a transaction may be aborted.

Figure 5:
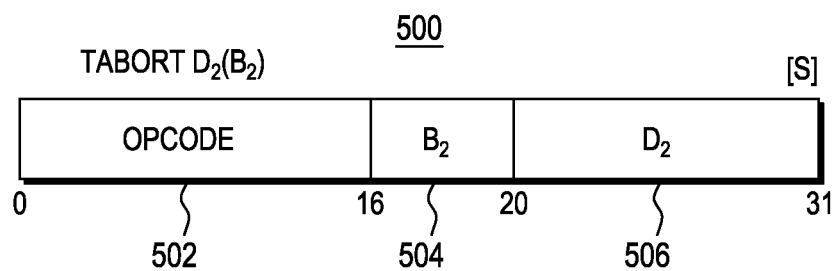
FIG. 5 depicts one example of a Transaction Abort (TABORT) instruction.

One example of a format of a TRANSACTION ABORT (TABORT) instruction is described with reference to FIG. 5. As one example, a TABORT instruction 500 includes an opcode field 502 that includes an opcode specifying a transaction abort operation; a base field ($B_2$) 504; and a displacement field ($D_2$) 506. When the $B_2$ field is nonzero, the contents of the general register specified by $B_2$ 504 are added to $D_2$ 506 to obtain a second operand address; otherwise, the second operand address is formed solely from the $D_2$ field, and the $B_2$ field is ignored. The second operand address is not used to address data; instead, the address forms the transaction abort code which is placed in a transaction diagnostic block during abort processing. Address computation for the second operand address follows the rules of address arithmetic: in the 24-bit addressing mode, bits 0-29 are set to zeros; in the 31-bit addressing mode, bits 0-32 are set to zeros.

Commit: At the completion of an outermost TRANSACTION END instruction, the CPU commits the store accesses made by the transaction (i.e., the outermost transaction and any nested levels) such that they are visible to other CPUs and the I/O subsystem. As observed by other CPUs and by the I/O subsystem, all fetch and store accesses made by all nested levels of the transaction appear to occur as a single concurrent operation when the commit occurs.

The contents of the general registers, access registers, floating-point registers, and the floating-point control register are not modified by the commit process. Any changes made to these registers during transactional execution are retained when the transaction's stores are committed.

Conflict: A transactional access made by one CPU conflicts with either (a) a transactional access or non-transactional access made by another CPU, or (b) the non-transactional access made by the I/O subsystem, if both accesses are to any location within the same cache line, and one or more of the accesses is a store.

A conflict may be detected by a CPU's speculative execution of instructions, even though the conflict may not be detected in the conceptual sequence.

Constrained Transaction: A constrained transaction is a transaction that executes in the constrained transactional execution mode and is subject to the following limitations:

A subset of the general instructions is available.
A limited number of instructions may be executed.
A limited number of storage-operand locations may be accessed.
The transaction is limited to a single nesting level.

In the absence of repeated interruptions or conflicts with other CPUs or the I/O subsystem, a constrained transaction eventually completes, thus an abort-handler routine is not required. Constrained transactions are described in detail below.

When a TRANSACTION BEGIN constrained (TBEGINC) instruction is executed while the CPU is already in the nonconstrained transaction execution mode, execution continues as a nested nonconstrained transaction.

Constrained Transactional Execution Mode: When the transaction nesting depth is zero, and a transaction is initiated by a TBEGINC instruction, the CPU enters the constrained transactional execution mode. While the CPU is in the constrained transactional execution mode, the transaction nesting depth is one.

Nested Transaction: When the TRANSACTION BEGIN instruction is issued while the CPU is in the nonconstrained transactional execution mode, the transaction is nested.

The transactional execution facility uses a model called flattened nesting. In the flattened nesting mode, stores made by an inner transaction are not observable by other CPUs and by the I/O subsystem until the outermost transaction commits its stores. Similarly, if a transaction aborts, all nested transactions abort, and all transactional stores of all nested transactions are discarded.

Figure 6:
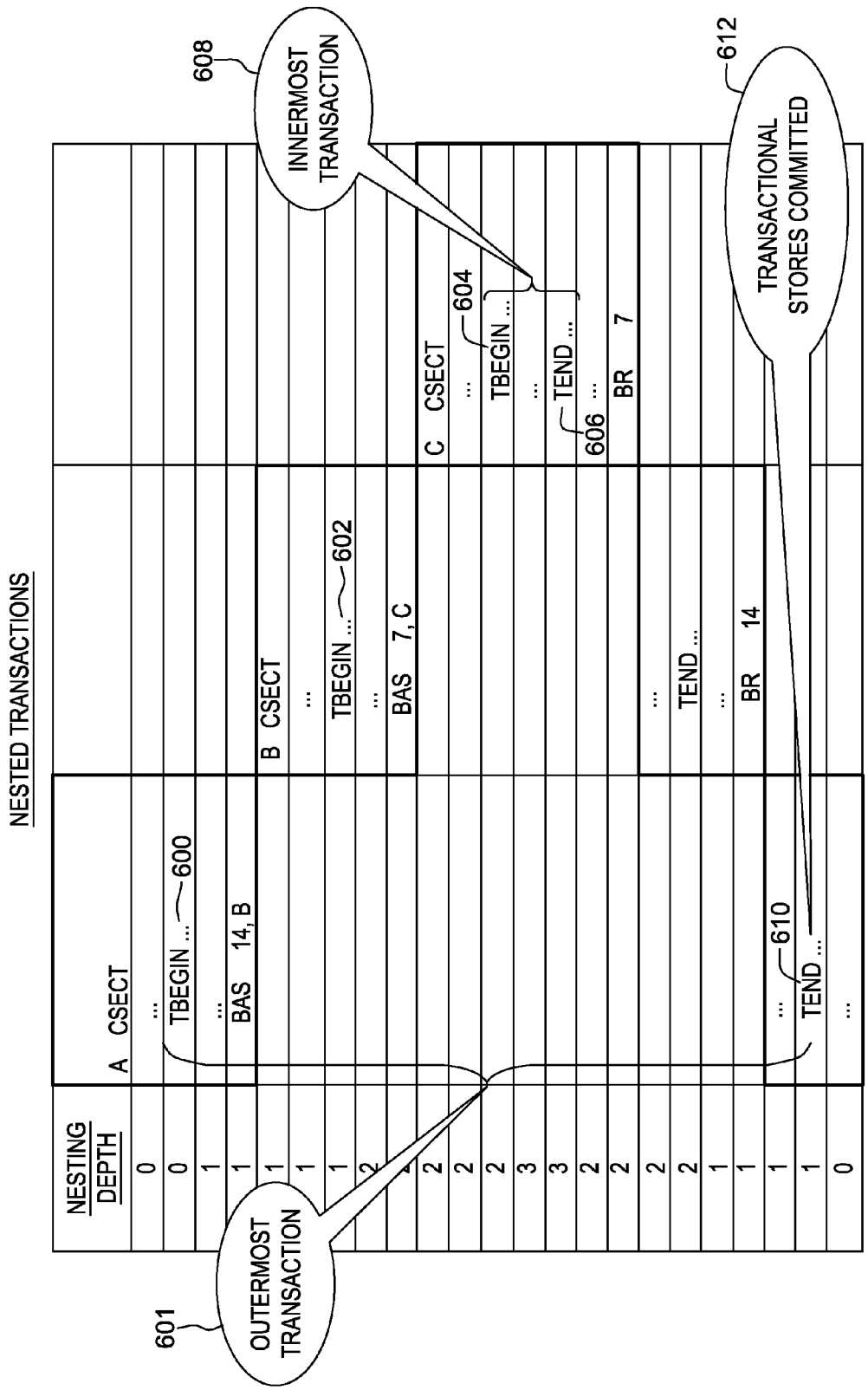
FIG. 6 depicts one example of nested transactions.

One example of nested transactions is depicted in FIG. 6. As shown, a first TBEGIN 600 starts an outermost transaction 601, TBEGIN 602 starts a first nested transaction, and TBEGIN 604 starts a second nested transaction. In this example, TBEGIN 604 and TEND 606 define an innermost transaction 608. When TEND 610 executes, transactional stores are committed 612 for the outermost transaction and all inner transactions.

Nonconstrained Transaction: A nonconstrained transaction is a transaction that executes in the nonconstrained transactional execution mode. Although a nonconstrained transaction is not limited in the manner as a constrained transaction, it may still be aborted due to a variety of causes.

Nonconstrained Transactional Execution Mode: When a transaction is initiated by the TBEGIN instruction, the CPU enters the nonconstrained transactional execution mode. While the CPU is in the nonconstrained transactional execution mode, the transaction nesting depth may vary from one to the maximum transaction nesting depth.

Non-Transactional Access: Non-transactional accesses are storage operand accesses made by the CPU when it is not in the transactional execution mode (that is, classic storage accesses outside of a transaction). Further, accesses made by the I/O subsystem are non-transactional accesses. Additionally, the NONTRANSACTIONAL STORE instruction may be used to cause a non-transactional store access while the CPU is in the nonconstrained transactional execution mode.

Figure 7:
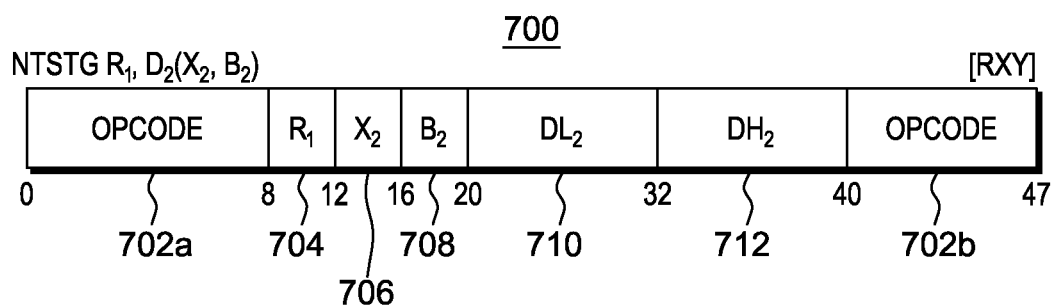
FIG. 7 depicts one example of a NONTRANSACTIONAL STORE (NTSTG) instruction.

One embodiment of a format of a NONTRANSACTIONAL STORE instruction is described with reference to FIG. 7. As one example, a NONTRANSACTIONAL STORE instruction 700 includes a plurality of opcode fields 702a, 702b specifying an opcode that designates a nontransactional store operation; a register field ($R_1$) 704 specifying a register, the contents of which are called the first operand; an index field ($X_2$) 706; a base field ($B_2$) 708; a first displacement field ($DL_2$) 710; and a second displacement field ($DH_2$) 712. The contents of the general registers designated by the $X_2$ and $B_2$ fields are added to the contents of a concatenation of contents of the $DH_2$ and $DL_2$ fields to form the second operand address. When either or both the $X_2$ or $B_2$ fields are zero, the corresponding register does not take part in the addition.

The 64 bit first operand is nontransactionally placed unchanged at the second operand location.

The displacement, formed by the concatenation of the $DH_2$ and $DL_2$ fields, is treated as a 20-bit signed binary integer.

The second operand is to be aligned on a double word boundary; otherwise, specification exception is recognized and the operation is suppressed.

Outer/Outermost Transaction: A transaction with a lower-numbered transaction nesting depth is an outer transaction. A transaction with a transaction nesting depth value of one is the outermost transaction.

An outermost TRANSACTION BEGIN instruction is one that is executed when the transaction nesting depth is initially zero. An outermost TRANSACTION END instruction is one that causes the transaction nesting depth to transition from one to zero. A constrained transaction is the outermost transaction, in this embodiment.

Program Interruption Filtering: When a transaction is aborted due to certain program exception conditions, the program can optionally prevent the interruption from occurring. This technique is called program interruption filtering. Program interruption filtering is subject to the transactional class of the interruption, the effective program interruption filtering control from the TRANSACTION BEGIN instruction, and the transactional execution program interruption filtering override in control register 0.

Transaction: A transaction includes the storage-operand accesses made, and selected general registers altered, while the CPU is in the transaction execution mode. For a nonconstrained transaction, storage-operand accesses may include both transactional accesses and non-transactional accesses. For a constrained transaction, storage-operand accesses are limited to transactional accesses. As observed by other CPUs and by the I/O subsystem, all storage-operand accesses made by the CPU while in the transaction execution mode appear to occur as a single concurrent operation. If a transaction is aborted, transactional store accesses are discarded, and any registers designated by the general register save mask of the outermost TRANSACTION BEGIN instruction are restored to their contents prior to transactional execution.

Transactional Accesses: Transactional accesses are storage operand accesses made while the CPU is in the transactional execution mode, with the exception of accesses made by the NONTRANSACTIONAL STORE instruction.

Transactional Execution Mode: The term transactional execution mode (a.k.a., transaction execution mode) describes the common operation of both the nonconstrained and the constrained transactional execution modes. Thus, when the operation is described, the terms nonconstrained and constrained are used to qualify the transactional execution mode.

When the transaction nesting depth is zero, the CPU is not in the transactional execution mode (also called the non-transactional execution mode).

As observed by the CPU, fetches and stores made in the transactional execution mode are no different than those made while not in the transactional execution mode.

In one embodiment of the z/Architecture, the transactional execution facility is under the control of bits 8-9 of control register 0, bits 61-63 of control register 2, the transaction nesting depth, the transaction diagnostic block address, and the transaction abort program status word (PSW).

Following an initial CPU reset, the contents of bit positions 8-9 of control register 0, bit positions 62-63 of control register 2, and the transaction nesting depth are set to zero. When the transactional execution control, bit 8 of control register 0, is zero, the CPU cannot be placed into the transactional execution mode.

Further details regarding the various controls are described below.

As indicated, the transactional execution facility is controlled by two bits in control register zero and three bits in control register two. For instance:

Control Register 0 Bits:

The bit assignments are as follows, in one embodiment:

Transactional Execution Control (TXC): Bit 8 of control register zero is the transactional execution control. This bit provides a mechanism whereby the control program (e.g., operating system) can indicate whether or not the transactional execution facility is usable by the program. Bit 8 is to be one to successfully enter the transactional execution mode.

When bit 8 of control register 0 is zero, attempted execution of the EXTRACT TRANSACTION NESTING DEPTH, TRANSACTION BEGIN and TRANSACTION END instructions results in a special operation execution.

Figure 8:
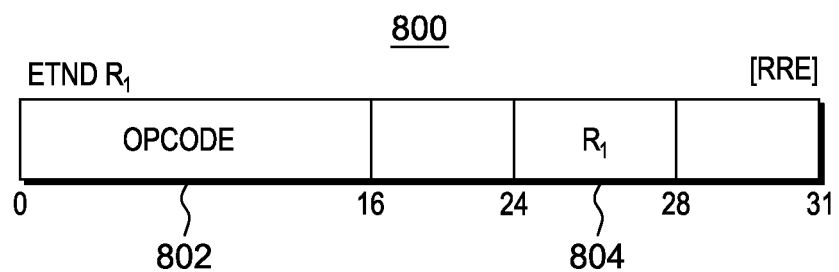
FIG. 8 depicts one example of an EXTRACT TRANSACTION NESTING DEPTH (ETND) instruction.

One embodiment of a format of an EXTRACT TRANSACTION NESTING DEPTH instruction is described with reference to FIG. 8. As one example, an EXTRACT TRANSACTION NESTING DEPTH instruction 800 includes an opcode field 802 specifying an opcode that indicates the extract transaction nesting depth operation; and a register field $R_1$ 804 that designates a general register.

The current transaction nesting depth is placed in bits 48-63 of general register $R_1$.

Bits 0-31 of the register remain unchanged, and bits 32-47 of the register are set to zero.

In a further embodiment, the maximum transaction nesting depth is also placed in general register $R_1$, such as in bits 16-31.

Transaction Execution Program Interruption Filtering Override (PIFO): Bit 9 of control register zero is the transactional execution program interruption filtering override. This bit provides a mechanism by which the control program can ensure that any program exception condition that occurs while the CPU is in the transactional execution mode results in an interruption, regardless of the effective program interruption filtering control specified or implied by the TRANSACTION BEGIN instruction(s).

Control Register 2 Bits:

The assignments are as follows, in one embodiment:

Transaction Diagnostic Scope (TDS): Bit 61 of control register 2 controls the applicability of the transaction diagnosis control (TDC) in bits 62-63 of the register, as follows:

| TDS | |
|---|---|
| Value | Meaning |
| 0 | The TDC applies regardless of whether the CPU is in the problem or supervisor state. |
| 1 | The TDC applies only when the CPU is in the problem state. When the CPU is in the supervisor state, processing is as if the TDC contained zero. |

Transaction Diagnostic Control (TDC): Bits 62-63 of control register 2 are a 2-bit unsigned integer that may be used to cause transactions to be randomly aborted for diagnostic purposes. The encoding of the TDC is as follows, in one example:

| TDC | |
|---|---|
| Value | Meaning |
| 0 | Normal operation; transactions are not aborted as a result of the TDC. |
| 1 | Abort every transaction at a random instruction, but before execution of the outermost TRANSACTION END instruction. |
| 2 | Abort random transactions at a random instruction. |
| 3 | Reserved |

When a transaction is aborted due to a nonzero TDC, then either of the following may occur:

The abort code is set to any of the codes 7-11, 13-16, or 255, with the value of the code randomly chosen by the CPU; the condition code is set corresponding to the abort code. Abort codes are further described below.

For a nonconstrained transaction, the condition code is set to one. In this case, the abort code is not applicable.

It is model dependent whether TDC value 1 is implemented. If not implemented, a value of 1 acts as if 2 was specified.

For a constrained transaction, a TDC value of 1 is treated as if a TDC value of 2 was specified.

If a TDC value of 3 is specified, the results are unpredictable.

Transaction Diagnostic Block Address (TDBA)

A valid transaction diagnostic block address (TDBA) is set from the first operand address of the outermost TRANSACTION BEGIN (TBEGIN) instruction when the $B_1$ field of the instruction is nonzero. When the CPU is in the primary space or access register mode, the TDBA designates a location in the primary address space. When the CPU is in the secondary space, or home space mode, the TDBA designates a location in the secondary or home address space, respectively. When DAT (Dynamic Address Translation) is off, the TDBA designates a location in real storage.

The TDBA is used by the CPU to locate the transaction diagnostic block—called the TBEGIN-specified TDB—if the transaction is subsequently aborted. The rightmost three bits of the TDBA are zero, meaning that the TBEGIN-specified TDB is on a doubleword boundary.

When the $B_1$ field of an outermost TRANSACTION BEGIN (TBEGIN) instruction is zero, the transactional diagnostic block address is invalid, and no TBEGIN-specified TDB is stored if the transaction is subsequently aborted.

Transaction Abort PSW (TAPSW)

During execution of the TRANSACTION BEGIN (TBEGIN) instruction when the nesting depth is initially zero, the transaction abort PSW is set to the contents of the current PSW; and the instruction address of the transaction abort PSW designates the next sequential instruction (that is, the instruction following the outermost TBEGIN). During execution of the TRANSACTION BEGIN constrained (TBEGINC) instruction when the nesting depth is initially zero, the transaction abort PSW is set to the contents of the current PSW, except that the instruction address of the transaction abort PSW designates the TBEGINC instruction (rather than the next sequential instruction following the TBEGINC).

When a transaction is aborted, the condition code in the transaction abort PSW is replaced with a code indicating the severity of the abort condition. Subsequently, if the transaction was aborted due to causes that do not result in an interruption, the PSW is loaded from the transaction abort PSW; if the transaction was aborted due to causes that result in an interruption, the transaction abort PSW is stored as the interruption old PSW.

The transaction abort PSW is not altered during the execution of any inner TRANSACTION BEGIN instruction.

Transaction Nesting Depth (TND)

The transaction nesting depth is, for instance, a 16-bit unsigned value that is incremented each time a TRANSACTION BEGIN instruction is completed with condition code 0 and decremented each time a TRANSACTION END instruction is completed. The transaction nesting depth is reset to zero when a transaction is aborted or by CPU reset.

In one embodiment, a maximum TND of 15 is implemented.

In one implementation, when the CPU is in the constrained transactional execution mode, the transaction nesting depth is one. Additionally, although the maximum TND can be represented as a 4-bit value, the TND is defined to be a 16-bit value to facilitate its inspection in the transaction diagnostic block.

Transaction Diagnostic Block (TDB)

When a transaction is aborted, various status information may be saved in a transaction diagnostic block (TDB), as follows:

1. TBEGIN-specified TDB: For a nonconstrained transaction, when the $B_1$ field of the outermost TBEGIN instruction is nonzero, the first operand address of the instruction designates the TBEGIN-specified TDB. This is an application program specified location that may be examined by the application's abort handler.
2. Program-Interruption (PI) TDB: If a nonconstrained transaction is aborted due to a non-filtered program exception condition, or if a constrained transaction is aborted due to any program exception condition (that is, any condition that results in a program interruption being recognized), the PI-TDB is stored into locations in the prefix area. This is available for the operating system to inspect and log out in any diagnostic reporting that it may provide.
3. Interception TDB: If the transaction is aborted due to any program exception condition that results in interception (that is, the condition causes interpretive execution to end and control to return to the host program), a TDB is stored into a location specified in the state description block for the guest operating system.

The TBEGIN-specified TDB is only stored, in one embodiment, when the TDB address is valid (that is, when the outermost TBEGIN instruction's $B_1$ field is nonzero).

For aborts due to unfiltered program exception conditions, only one of either the PI-TDB or Interception TDB will be stored. Thus, there may be zero, one, or two TDBs stored for an abort.

Further details regarding one example of each of the TDBs are described below:

TBEGIN-Specified TDB:

The 256-byte location specified by a valid transaction diagnostic block address. When the transaction diagnostic block address is valid, the TBEGIN-specified TDB is stored on a transaction abort. The TBEGIN-specified TDB is subject to all storage protection mechanisms that are in effect at the execution of the outermost TRANSACTION BEGIN instruction. A PER (Program Event Recording) storage alteration event for any portion of the TBEGIN-specified TDB is detected during the execution of the outermost TBEGIN, not during the transaction abort processing.

One purpose of PER is to assist in debugging programs. It permits the program to be alerted to the following types of events, as examples:

Execution of a successful branch instruction. The option is provided of having an event occur only when the branch target location is within the designated storage area.

Fetching of an instruction from the designated storage area.

Alteration of the contents of the designated storage area. The option is provided of having an event occur only when the storage area is within designated address spaces.

Execution of a STORE USING REAL ADDRESS instruction.

Execution of the TRANSACTION END instruction.

The program can selectively specify that one or more of the above types of events be recognized, except that the event for STORE USING REAL ADDRESS can be specified only along with the storage alteration event. The information concerning a PER event is provided to the program by means of a program interruption, with the cause of the interruption being identified in the interruption code.

When the transaction diagnostic block address is not valid, a TBEGIN-specified TDB is not stored.

Program-Interruption TDB:

Real locations 6,144-6,399 (1800-18FF hex). The program interruption TDB is stored when a transaction is aborted due to program interruption. When a transaction is aborted due to other causes, the contents of the program interruption TDB are unpredictable.

The program interruption TDB is not subject to any protection mechanism. PER storage alteration events are not detected for the program interruption TDB when it is stored during a program interruption.

Interception TDB:

The 256-byte host real location specified by locations 488-495 of the state description. The interception TDB is stored when an aborted transaction results in a guest program interruption interception (that is, interception code 8). When a transaction is aborted due to other causes, the contents of the interception TDB are unpredictable. The interception TDB is not subject to any protection mechanism.

Figure 9:
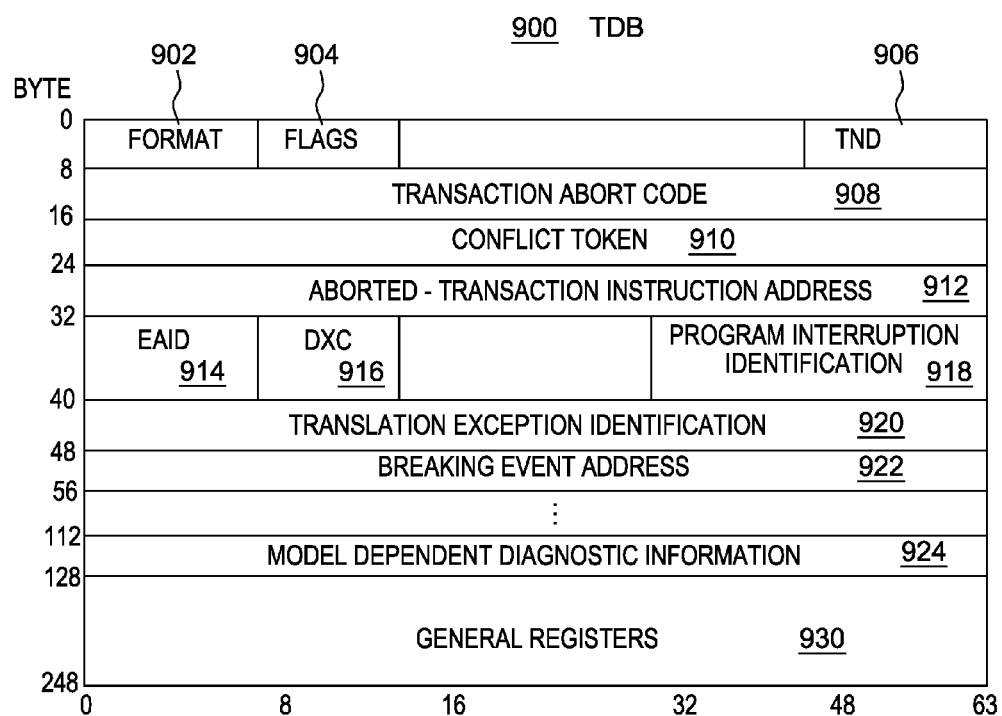
FIG. 9 depicts one example of a transaction diagnostic block.

As depicted in FIG. 9, the fields of a transaction diagnostic block 900 are as follows, in one embodiment:

Format 902: Byte 0 contains a validity and format indication, as follows:

| Value | Meaning |
|---|---|
| 0 | The remaining fields of the TDB are unpredictable. |
| 1 | A format-1 TDB, the remaining fields of which are described below. |
| 2-255 | Reserved |

A TDB in which the format field is zero is referred to as a null TDB.

Flags 904: Byte 1 contains various indications, as follows:

Conflict Token Validity (CTV): When a transaction is aborted due to a fetch or store conflict (that is, abort codes 9 or 10, respectively), bit 0 of byte 1 is the conflict token validity indication. When the CTV indication is one, the conflict token 910 in bytes 16-23 of the TDB contain the logical address at which the conflict was detected. When the CTV indication is zero, bytes 16-23 of the TDB are unpredictable.

When a transaction is aborted due to any reason other than a fetch or store conflict, bit 0 of byte 1 is stored as zero.

Constrained-Transaction Indication (CTI): When the CPU is in the constrained transactional execution mode, bit 1 of byte 1 is set to one. When the CPU is in the nonconstrained transactional execution mode, bit 1 of byte 1 is set to zero.

Reserved: Bits 2-7 of byte 1 are reserved, and stored as zeros.

Transaction Nesting Depth (TND) 906: Bytes 6-7 contain the transaction nesting depth when the transaction was aborted.

Transaction Abort Code (TAC) 908: Bytes 8-15 contain a 64-bit unsigned transaction abort code. Each code point indicates a reason for a transaction being aborted.

It is model dependent whether the transaction abort code is stored in the program interruption TDB when a transaction is aborted due to conditions other than a program interruption.

Conflict Token 910: For transactions that are aborted due to fetch or store conflict (that is, abort codes 9 and 10, respectively), bytes 16-23 contain the logical address of the storage location at which the conflict was detected. The conflict token is meaningful when the CTV bit, bit 0 of byte 1, is one.

When the CTV bit is zero, bytes 16-23 are unpredictable.

Because of speculative execution by the CPU, the conflict token may designate a storage location that would not necessarily be accessed by the transaction's conceptual execution sequence.

Aborted Transaction Instruction Address (ATIA) 912: Bytes 24-31 contain an instruction address that identifies the instruction that was executing when an abort was detected. When a transaction is aborted due to abort codes 2, 5, 6, 11, 13, or 256 or higher, or when a transaction is aborted due to abort codes 4 or 13 and the program exception condition is nullifying, the ATIA points directly to the instruction that was being executed. When a transaction is aborted due to abort codes 4 or 12, and the program exception condition is not nullifying, the ATIA points past the instruction that was being executed.

When a transaction is aborted due to abort codes 7-10, 14-16, or 255, the ATIA does not necessarily indicate the exact instruction causing the abort, but may point to an earlier or later instruction within the transaction.

If a transaction is aborted due to an instruction that is the target of an execute-type instruction, the ATIA identifies the execute-type instruction, either pointing to the instruction or past it, depending on the abort code as described above. The ATIA does not indicate the target of the execute-type instruction.

The ATIA is subject to the addressing mode when the transaction is aborted. In the 24-bit addressing mode, bits 0-40 of the field contain zeros. In the 31-bit addressing mode, bits 0-32 of the field contain zeros.

It is model dependent whether the aborted transaction instruction address is stored in the program interruption TDB when a transaction is aborted due to conditions other than a program interruption.

When a transaction is aborted due to abort code 4 or 12, and the program exception condition is not nullifying, the ATIA does not point to the instruction causing the abort. By subtracting the number of halfwords indicated by the interruption length code (ILC) from the ATIA, the instruction causing the abort can be identified in conditions that are suppressing or terminating, or for non-PER events that are completing. When a transaction is aborted due to a PER event, and no other program exception condition is present, the ATIA is unpredictable.

When the transaction diagnostic block address is valid, the ILC may be examined in program interruption identification (PIID) in bytes 36-39 of the TBEGIN-specified TDB. When filtering does not apply, the ILC may be examined in the PIID at location 140-143 in real storage.

Exception Access Identification (EAID) 914: For transactions that are aborted due to certain filtered program exception conditions, byte 32 of the TBEGIN-specified TDB contains the exception access identification. In one example of the z/Architecture, the format of the EAID, and the cases for which it is stored, are the same as those described in real location 160 when the exception condition results in an interruption, as described in the above-incorporated by reference Principles of Operation.

For transactions that are aborted for other reasons, including any exception conditions that result in a program interruption, byte 32 is unpredictable. Byte 32 is unpredictable in the program interruption TDB.

This field is stored only in the TDB designated by the transaction diagnostic block address; otherwise, the field is reserved. The EAID is stored only for access list controlled or DAT protection, ASCE-type, page translation, region first translation, region second translation, region third translation, and segment translation program exception conditions.

Data Exception Code (DXC) 916: For transactions that are aborted due to filtered data exception program exception conditions, byte 33 of the TBEGIN specified TDB contains the data exception code. In one example of the z/Architecture, the format of the DXC, and the cases for which it is stored, are the same as those described in real location 147 when the exception condition results in an interruption, as described in the above-incorporated by reference Principles of Operation. In one example, location 147 includes the DXC.

For transactions that are aborted for other reasons, including any exception conditions that result in a program interruption, byte 33 is unpredictable. Byte 33 is unpredictable in the program interruption TDB.

This field is stored only in the TDB designated by the transaction diagnostic block address; otherwise, the field is reserved. The DXC is stored only for data program exception conditions.

Program Interruption Identification (PIID) 918: For transactions that are aborted due to filtered program exception conditions, bytes 36-39 of the TBEGIN-specified TDB contain the program interruption identification. In one example of the z/Architecture, the format of the PIID is the same as that described in real locations 140-143 when the condition results in an interruption (as described in the above-incorporated by reference Principles of Operation), except that the instruction length code in bits 13-14 of the PIID is respective to the instruction at which the exception condition was detected.

For transactions that are aborted for other reasons, including exception conditions that result in a program interruption, bytes 36-39 are unpredictable. Bytes 36-39 are unpredictable in the program interruption TDB.

This field is stored only in the TDB designated by the transaction diagnostic block address; otherwise, the field is reserved. The program interruption identification is only stored for program exception conditions.

Translation Exception Identification (TEID) 920: For transactions that are aborted due to any of the following filtered program exception conditions, bytes 40-47 of the TBEGIN-specified TDB contain the translation exception identification.

Access list controlled or DAT protection
ASCE-type
Page translation
Region-first translation
Region-second translation
Region-third translation
Segment translation exception In one example of the z/Architecture, the format of the TEID is the same as that described in real locations 168-175 when the condition results in an interruption, as described in the above-incorporated by reference Principles of Operation.

For transactions that are aborted for other reasons, including exception conditions that result in a program interruption, bytes 40-47 are unpredictable. Bytes 40-47 are unpredictable in the program interruption TDB.

This field is stored only in the TDB designated by the transaction diagnostic block address; otherwise, the field is reserved.

Breaking Event Address 922: For transactions that are aborted due to filtered program exception conditions, bytes 48-55 of the TBEGIN-specified TDB contain the breaking event address. In one example of the z/Architecture, the format of the breaking event address is the same as that described in real locations 272-279 when the condition results in an interruption, as described in the above-incorporated by reference Principles of Operation.

For transactions that are aborted for other reasons, including exception conditions that result in a program interruption, bytes 48-55 are unpredictable. Bytes 48-55 are unpredictable in the program interruption TDB.

This field is stored only in the TDB designated by the transaction diagnostic block address; otherwise, the field is reserved.

Further details relating to breaking events are described below.

In one embodiment of the z/Architecture, when the PER-3 facility is installed, it provides the program with the address of the last instruction to cause a break in the sequential execution of the CPU. Breaking event address recording can be used as a debugging assist for wild branch detection. This facility provides, for instance, a 64-bit register in the CPU, called the breaking event address register. Each time an instruction other than TRANSACTION ABORT causes a break in the sequential instruction execution (that is, the instruction address in the PSW is replaced, rather than incremented by the length of the instruction), the address of that instruction is placed in the breaking event address register. Whenever a program interruption occurs, whether or not PER is indicated, the current contents of the breaking event address register are placed in real storage locations 272-279.

If the instruction causing the breaking event is the target of an execute-type instruction (EXECUTE or EXECUTE RELATIVE LONG), then the instruction address used to fetch the execute-type instruction is placed in the breaking event address register.

In one embodiment of the z/Architecture, a breaking event is considered to occur whenever one of the following instructions causes branching: BRANCH AND LINK (BAL, BALR); BRANCH AND SAVE (BAS, BASR); BRANCH AND SAVE AND SET MODE (BASSM); BRANCH AND SET MODE (BSM); BRANCH AND STACK (BAKR); BRANCH ON CONDITION (BC, BCR); BRANCH ON COUNT (BCT, BCTR, BCTG, BCTGR); BRANCH ON INDEX HIGH (BXH, BXHG); BRANCH ON INDEX LOW OR EQUAL (BXLE, BXLEG); BRANCH RELATIVE ON CONDITION (BRC); BRANCH RELATIVE ON CONDITION LONG (BRCL); BRANCH RELATIVE ON COUNT (BRCT, BRCTG); BRANCH RELATIVE ON INDEX HIGH (BRXH, BRXHG); BRANCH RELATIVE ON INDEX LOW OR EQUAL (BRXLE, BRXLG); COMPARE AND BRANCH (CRB, CGRB); COMPARE AND BRANCH RELATIVE (CRJ, CGRJ); COMPARE IMMEDIATE AND BRANCH (CIB, CGIB); COMPARE IMMEDIATE AND BRANCH RELATIVE (CIJ, CGIJ); COMPARE LOGICAL AND BRANCH (CLRB, CLGRB); COMPARE LOGICAL AND BRANCH RELATIVE (CLRJ, CLGRJ); COMPARE LOGICAL IMMEDIATE AND BRANCH (CLIB, CLGIB); and COMPARE LOGICAL IMMEDIATE AND BRANCH RELATIVE (CLIJ, CLGIJ).

A breaking event is also considered to occur whenever one of the following instructions completes: BRANCH AND SET AUTHORITY (BSA); BRANCH IN SUBSPACE GROUP (BSG); BRANCH RELATIVE AND SAVE (BRAS); BRANCH RELATIVE AND SAVE LONG (BRASL); LOAD PSW (LPSW); LOAD PSW EXTENDED (LPSWE); PROGRAM CALL (PC); PROGRAM RETURN (PR); PROGRAM TRANSFER (PT); PROGRAM TRANSFER WITH INSTANCE (PTI); RESUME PROGRAM (RP); and TRAP (TRAP2, TRAP4).

A breaking event is not considered to occur as a result of a transaction being aborted (either implicitly or as a result of the TRANSACTION ABORT instruction).

Model Dependent Diagnostic Information 924: Bytes 112-127 contain model dependent diagnostic information.

For all abort codes except 12 (filtered program interruption), the model dependent diagnostic information is saved in each TDB that is stored.

In one embodiment, the model dependent diagnostic information includes the following:

Bytes 112-119 contain a vector of 64 bits called the transactional execution branch indications (TXBI). Each of the first 63 bits of the vector indicates the results of executing a branching instruction while the CPU was in the transactional execution mode, as follows:

| Value | Meaning |
| --- | --- |
| 0 | The instruction completed without branching. |
| 1 | The instruction completed with branching. |

Bit 0 represents the result of the first such branching instruction, bit 1 represents the result of the second such instruction, and so forth.

If fewer than 63 branching instructions were executed while the CPU was in the transactional execution mode, the rightmost bits that do not correspond to branching instructions are set to zeros (including bit 63). When more than 63 branching instructions were executed, bit 63 of the TXBI is set to one.

Bits in the TXBI are set by instructions which are capable of causing a breaking event, as listed above, except for the following:

Any restricted instruction does not cause a bit to be set in the TXBI.

For instructions of, for instance, the z/Architecture, when the $M_1$ field of the BRANCH ON CONDITION, BRANCH RELATIVE ON CONDITION, or BRANCH RELATIVE ON CONDITION LONG instruction is zero, or when the $R_2$ field of the following instructions is zero, it is model dependent whether the execution of the instruction causes a bit to be set in the TXBI.

BRANCH AND LINK (BALR); BRANCH AND SAVE (BASR); BRANCH AND SAVE AND SET MODE (BASSM); BRANCH AND SET MODE (BSM); BRANCH ON CONDITION (BCR); and BRANCH ON COUNT (BCTR, BCTGR)

For abort conditions that were caused by a host access exception, bit position 0 of byte 127 is set to one. For all other abort conditions, bit position 0 of byte 127 is set to zero.

For abort conditions that were detected by the load/store unit (LSU), the rightmost five bits of byte 127 contain an indication of the cause. For abort conditions that were not detected by the LSU, byte 127 is reserved.

General Registers 930: Bytes 128-255 contain the contents of general registers 0-15 at the time the transaction was aborted. The registers are stored in ascending order, beginning with general register 0 in bytes 128-135, general register 1 in bytes 136-143, and so forth.

Reserved: All other fields are reserved. Unless indicated otherwise, the contents of reserved fields are unpredictable.

As observed by other CPUs and the I/O subsystem, storing of the TDB(s) during a transaction abort is a multiple access reference occurring after any non-transactional stores.

A transaction may be aborted due to causes that are outside the scope of the immediate configuration in which it executes. For example, transient events recognized by a hypervisor (such as LPAR or z/VM) may cause a transaction to be aborted.

The information provided in the transaction diagnostic block is intended for diagnostic purposes and is substantially correct. However, because an abort may have been caused by an event outside the scope of the immediate configuration, information such as the abort code or program interruption identification may not accurately reflect conditions within the configuration, and thus, should not be used in determining program action.

In addition to the diagnostic information saved in the TDB, when a transaction is aborted due to any data exception program exception condition and both the AFP register control, bit 45 of control register 0, and the effective allow floating point operation control (F) are one, the data exception code (DXC) is placed into byte 2 of the floating point control register (FPCR), regardless of whether filtering applies to the program exception condition. When a transaction is aborted, and either or both the AFP register control or effective allow floating point operation control are zero, the DXC is not placed into the FPCR.

In one embodiment, as indicated herein, when the transactional execution facility is installed, the following general instructions are provided.

EXTRACT TRANSACTION NESTING DEPTH
NONTRANSACTIONAL STORE
TRANSACTION ABORT
TRANSACTION BEGIN
TRANSACTION END

When the CPU is in the transactional execution mode, attempted execution of certain instructions is restricted and causes the transaction to be aborted.

When issued in the constrained transactional execution mode, attempted execution of restricted instructions may also result in a transaction constraint program interruption, or may result in execution proceeding as if the transaction was not constrained.

In one example of the z/Architecture, restricted instructions include, as examples, the following non-privileged instructions: COMPARE AND SWAP AND STORE; MODIFY RUNTIME INSTRUMENTATION CONTROLS; PERFORM LOCKED OPERATION; PREFETCH DATA (RELATIVE LONG), when the code in the $M_1$ field is 6 or 7; STORE CHARACTERS UNDER MASK HIGH, when the $M_3$ field is zero and the code in the $R_1$ field is 6 or 7; STORE FACILITY LIST EXTENDED; STORE RUNTIME INSTRUMENTATION CONTROLS; SUPERVISOR CALL; and TEST RUNTIME INSTRUMENTATION CONTROLS.

In the above list, COMPARE AND SWAP AND STORE and PERFORM LOCKED OPERATION are complex instructions which can be more efficiently implemented by the use of basic instructions in the TX mode. The cases for PREFETCH DATA and PREFETCH DATA RELATIVE LONG are restricted as the codes of 6 and 7 release a cache line, necessitating the commitment of the data potentially prior to the completion of a transaction. SUPERVISOR CALL is restricted as it causes an interruption (which causes a transaction to be aborted).

Under the conditions listed below, the following instructions are restricted:

BRANCH AND LINK (BALR), BRANCH AND SAVE (BASR), and BRANCH AND SAVE AND SET MODE, when the $R_2$ field of the instruction is nonzero and branch tracing is enabled.

BRANCH AND SAVE AND SET MODE and BRANCH AND SET MODE, when the $R_2$ field is nonzero and mode tracing is enabled; SET ADDRESSING MODE, when mode tracing is enabled.

MONITOR CALL, when a monitor event condition is recognized.

The above list includes instructions that may form trace entries. If these instructions were allowed to execute transactionally and formed trace entries, and the transaction subsequently aborted, the trace table pointer in control register 12 would be advanced, but the stores to the trace table would be discarded. This would leave an inconsistent gap in the trace table. Thus, the instructions are restricted in the cases where they would form trace entries.

When the CPU is in the transactional execution mode, it is model dependent whether the following instructions are restricted: CIPHER MESSAGE; CIPHER MESSAGE WITH CFB; CIPHER MESSAGE WITH CHAINING; CIPHER MESSAGE WITH COUNTER; CIPHER MESSAGE WITH OFB; COMPRESSION CALL; COMPUTE INTERMEDIATE MESSAGE DIGEST; COMPUTE LAST MESSAGE DIGEST; COMPUTE MESSAGE AUTHENTICATION CODE; CONVERT UNICODE-16 TO UNICODE-32; CONVERT UNICODE-16 TO UNICODE-8; CONVERT UNICODE-32 TO UNICODE-16; CONVERT UNICODE-32 TO UNICODE-8; CONVERT UNICODE-8 TO UNICODE-16; CONVERT UNICODE-8 TO UNICODE-32; PERFORM CRYPTOGRAPHIC COMPUTATION; RUNTIME INSTRUMENTATION OFF; and RUNTIME INSTRUMENTATION ON.

Each of the above instructions is either currently implemented by the hardware co-processor, or has been in past machines, and thus, is considered restricted.

When the effective allow AR modification (A) control is zero, the following instructions are restricted: COPY ACCESS; LOAD ACCESS MULTIPLE; LOAD ADDRESS EXTENDED; and SET ACCESS.

Each of the above instructions causes the contents of an access register to be modified. If the A control in the TRANSACTION BEGIN instruction is zero, then the program has explicitly indicated that access register modification is not to be allowed.

When the effective allow floating point operation (F) control is zero, floating point instructions are restricted.

Under certain circumstances, the following instructions may be restricted: EXTRACT CPU TIME; EXTRACT PSW; STORE CLOCK; STORE CLOCK EXTENDED; and STORE CLOCK FAST.

Each of the above instructions is subject to an interception control in the interpretative execution state description. If the hypervisor has set the interception control for these instructions, then their execution may be prolonged due to hypervisor implementation; thus, they are considered restricted if an interception occurs.

When a nonconstrained transaction is aborted because of the attempted execution of a restricted instruction, the transaction abort code in the transaction diagnostic block is set to 11 (restricted instruction), and the condition code is set to 3, except as follows: when a nonconstrained transaction is aborted due to the attempted execution of an instruction that would otherwise result in a privileged operation exception, it is unpredictable whether the abort code is set to 11 (restricted instruction) or 4 (unfiltered program interruption resulting from the recognition of the privileged operation program interruption). When a nonconstrained transaction is aborted due to the attempted execution of PREFETCH DATA (RELATIVE LONG) when the code in the $M_1$ field is 6 or 7 or STORE CHARACTERS UNDER MASK HIGH when the $M_3$ field is zero and the code in the $R_1$ field is 6 or 7, it is unpredictable whether the abort code is set to 11 (restricted instruction) or 16 (cache other). When a nonconstrained transaction is aborted due to the attempted execution of MONITOR CALL, and both a monitor event condition and a specification exception condition are present it is unpredictable whether the abort code is set to 11 or 4, or, if the program interruption is filtered, 12.

Additional instructions may be restricted in a constrained transaction. Although these instructions are not currently defined to be restricted in a nonconstrained transaction, they may be restricted under certain circumstances in a nonconstrained transaction on future processors.

Certain restricted instructions may be allowed in the transactional execution mode on future processors. Therefore, the program should not rely on the transaction being aborted due to the attempted execution of a restricted instruction. The TRANSACTION ABORT instruction should be used to reliably cause a transaction to be aborted.

In a nonconstrained transaction, the program should provide an alternative non-transactional code path to accommodate a transaction that aborts due to a restricted instruction.

In operation, when the transaction nesting depth is zero, execution of the TRANSACTION BEGIN (TBEGIN) instruction resulting in condition code zero causes the CPU to enter the nonconstrained transactional execution mode. When the transaction nesting depth is zero, execution of the TRANSACTION BEGIN constrained (TBEGINC) instruction resulting in condition code zero causes the CPU to enter the constrained transactional execution mode.

Except where explicitly noted otherwise, all rules that apply for non-transactional execution also apply to transactional execution. Below are additional characteristics of processing while the CPU is in the transactional execution mode.

When the CPU is in the nonconstrained transactional execution mode, execution of the TRANSACTION BEGIN instruction resulting in condition code zero causes the CPU to remain in the nonconstrained transactional execution mode.

As observed by the CPU, fetches and stores made in the transaction execution mode are no different than those made while not in the transactional execution mode. As observed by other CPUs and by the I/O subsystem, all storage operand accesses made while a CPU is in the transactional execution mode appear to be a single block concurrent access. That is, the accesses to all bytes within a halfword, word, doubleword, or quadword are specified to appear to be block concurrent as observed by other CPUs and I/O (e.g., channel) programs. The halfword, word, doubleword, or quadword is referred to in this section as a block. When a fetch-type reference is specified to appear to be concurrent within a block, no store access to the block by another CPU or I/O program is permitted during the time that bytes contained in the block are being fetched. When a store-type reference is specified to appear to be concurrent within a block, no access to the block, either fetch or store, is permitted by another CPU or I/O program during the time that the bytes within the block are being stored.

Storage accesses for instruction and DAT and ART (Access Register Table) table fetches follow the non-transactional rules.

The CPU leaves the transactional execution mode normally by means of a TRANSACTION END instruction that causes the transaction nesting depth to transition to zero, in which case, the transaction completes.

When the CPU leaves the transactional execution mode by means of the completion of a TRANSACTION END instruction, all stores made while in the transactional execution mode are committed; that is, the stores appear to occur as a single block-concurrent operation as observed by other CPUs and by the I/O subsystem.

A transaction may be implicitly aborted for a variety of causes, or it may be explicitly aborted by the TRANSACTION ABORT instruction. Example possible causes of a transaction abort, the corresponding abort code, and the condition code that is placed into the transaction abort PSW are described below.

External Interruption: The transaction abort code is set to 2, and the condition code in the transaction abort PSW is set to 2. The transaction abort PSW is stored as the external old PSW as a part of external interruption processing.

Program Interruption (Unfiltered): A program exception condition that results in an interruption (that is, an unfiltered condition) causes the transaction to be aborted with code 4. The condition code in the transaction abort PSW is set specific to the program interruption code. The transaction abort PSW is stored as the program old PSW as a part of program interruption processing.

An instruction that would otherwise result in a transaction being aborted due to an operation exception may yield alternate results: for a nonconstrained transaction, the transaction may instead abort with abort code 11 (restricted instruction); for a constrained transaction, a transaction constraint program interruption may be recognized instead of the operation exception.

When a PER (Program Event Recording) event is recognized in conjunction with any other unfiltered program exception condition, the condition code is set to 3.

Machine Check Interruption: The transaction abort code is set to 5, and the condition code in the transaction abort PSW is set to 2. The transaction abort PSW is stored as the machine check old PSW as a part of machine check interruption processing.

I/O Interruption: The transaction abort code is set to 6, and the condition code in the transaction abort PSW is set to 2. The transaction abort PSW is stored as the I/O old PSW as a part of I/O interruption processing.

Fetch Overflow: A fetch overflow condition is detected when the transaction attempts to fetch from more locations than the CPU supports. The transaction abort code is set to 7, and the condition code is set to either 2 or 3.

Store Overflow: A store overflow condition is detected when the transaction attempts to store to more locations than the CPU supports. The transaction abort code is set to 8, and the condition code is set to either 2 or 3.

Allowing the condition code to be either 2 or 3 in response to a fetch or store overflow abort allows the CPU to indicate potentially retryable situations (e.g., condition code 2 indicates re-execution of the transaction may be productive; while condition code 3 does not recommend re-execution).

Fetch Conflict: A fetch conflict condition is detected when another CPU or the I/O subsystem attempts to store into a location that has been transactionally fetched by this CPU. The transaction abort code is set to 9, and the condition code is set to 2.

Store Conflict: A store conflict condition is detected when another CPU or the I/O subsystem attempts to access a location that has been stored during transactional execution by this CPU. The transaction abort code is set to 10, and the condition code is set to 2.

Restricted Instruction: When the CPU is in the transactional execution mode, attempted execution of a restricted instruction causes the transaction to be aborted. The transaction abort code is set to 11, and the condition code is set to 3.

When the CPU is in the constrained transactional execution mode, it is unpredictable whether attempted execution of a restricted instruction results in a transaction constraint program interruption or an abort due to a restricted instruction. The transaction is still aborted but the abort code may indicate either cause.

Program Exception Condition (Filtered): A program exception condition that does not result in an interruption (that is, a filtered condition) causes the transaction to be aborted with a transaction abort code of 12. The condition code is set to 3.

Nesting Depth Exceeded: The nesting depth exceeded condition is detected when the transaction nesting depth is at the maximum allowable value for the configuration, and a TRANSACTION BEGIN instruction is executed. The transaction is aborted with a transaction abort code of 13, and the condition code is set to 3.

Cache Fetch Related Condition: A condition related to storage locations fetched by the transaction is detected by the CPU's cache circuitry. The transaction is aborted with a transaction abort code of 14, and the condition code is set to either 2 or 3.

Cache Store Related Condition: A condition related to storage locations stored by the transaction is detected by the CPU's cache circuitry. The transaction is aborted with a transaction abort code of 15, and the condition code is set to either 2 or 3.

Cache Other Condition: A cache other condition is detected by the CPU's cache circuitry. The transaction is aborted with a transaction abort code of 16, and the condition code is set to either 2 or 3.

During transactional execution, if the CPU accesses instructions or storage operands using different logical addresses that are mapped to the same absolute address, it is model dependent whether the transaction is aborted. If the transaction is aborted due to accesses using different logical addresses mapped to the same absolute address, abort code 14, 15, or 16 is set, depending on the condition.

Miscellaneous Condition: A miscellaneous condition is any other condition recognized by the CPU that causes the transaction to abort. The transaction abort code is set to 255 and the condition code is set to either 2 or 3.

When multiple configurations are executing in the same machine (for example, logical partitions or virtual machines), a transaction may be aborted due to an external machine check or I/O interruption that occurred in a different configuration.

Although examples are provided above, other causes of a transaction abort with corresponding abort codes and condition codes may be provided. For instance, a cause may be a Restart Interruption, in which the transaction abort code is set to 1, and the condition code in the transaction abort PSW is set to 2. The transaction abort PSW is stored as the restart-old PSW as a part of restart processing. As a further example, a cause may be a Supervisor Call condition, in which the abort code is set to 3, and the condition code in the transaction abort PSW is set to 3. Other or different examples are also possible.

Notes:
1. The miscellaneous condition may result from any of the following:
   Instructions, such as, in the z/Architecture, COMPARE AND REPLACE DAT TABLE ENTRY, COMPARE AND SWAP AND PURGE, INVALIDATE DAT TABLE ENTRY, INVALIDATE PAGE TABLE ENTRY, PERFORM FRAME MANAGEMENT FUNCTION in which the NQ control is zero and the SK control is one, SET STORAGE KEY EXTENDED in which the NQ control is zero, performed by another CPU in the configuration; the condition code is set to 2.

An operator function, such as reset, restart or stop, or the equivalent SIGNAL PROCESSOR order is performed on the CPU.

Any other condition not enumerated above; the condition code is set to 2 or 3.

2. The location at which fetch and store conflicts are detected may be anywhere within the same cache line.

3. Under certain conditions, the CPU may not be able to distinguish between similar abort conditions. For example, a fetch or store overflow may be indistinguishable from a respective fetch or store conflict.

4. Speculative execution of multiple instruction paths by the CPU may result in a transaction being aborted due to conflict or overflow conditions, even if such conditions do not occur in the conceptual sequence. While in the constrained transactional execution mode, the CPU may temporarily inhibit speculative execution, allowing the transaction to attempt to complete without detecting such conflicts or overflows speculatively.

Execution of a TRANSACTION ABORT instruction causes the transaction to abort. The transaction abort code is set from the second operand address. The condition code is set to either 2 or 3, depending on whether bit 63 of the second operand address is zero or one, respectively.

FIG. 10 summarizes example abort codes stored in a transaction diagnostic block, and the corresponding condition code (CC). The description in FIG. 10 illustrates one particular implementation. Other implementations and encodings of values are possible.

In one embodiment, and as mentioned above, the transactional facility provides for both constrained transactions and nonconstrained transactions, as well as processing associated therewith. Initially, constrained transactions are discussed and then nonconstrained transactions A constrained transaction executes in transactional mode without a fall-back path. It is a mode of processing useful for compact functions. In the absence of repeated interruptions or conflicts with other CPUs or the I/O subsystem (i.e., caused by conditions that will not allow the transaction to complete successfully), a constrained transaction will eventually complete; thus, an abort handler routine is not required and is not specified. For instance, in the absence of violation of a condition that cannot be addressed (e.g., divide by 0); a condition that does not allow the transaction to complete (e.g., a timer interruption that does not allow an instruction to run; a hot I/O; etc.); or a violation of a restriction or constraint associated with a constrained transaction, the transaction will eventually complete.

A constrained transaction is initiated by a TRANSACTION BEGIN constrained (TBEGINC) instruction when the transaction nesting depth is initially zero. A constrained transaction is subject to the following constraints, in one embodiment.

1. The transaction executes no more than 32 instructions, not including the TRANSACTION BEGIN constrained (TBEGINC) and TRANSACTION END instructions.

2. All instructions in the transaction are to be within 256 contiguous bytes of storage, including the TRANSACTION BEGIN constrained (TBEGINC) and any TRANSACTION END instructions.

3. In addition to the restricted instructions, the following restrictions apply to a constrained transaction.

a. Instructions are limited to those referred to as General Instructions, including, for instance, add, subtract, multiply, divide, shift, rotate, etc.

b. Branching instructions are limited to the following (the instructions listed are of the z/Architecture in one example):

BRANCH RELATIVE ON CONDITION in which the $M_1$ is nonzero and the $RI_2$ field contains a positive value.

BRANCH RELATIVE ON CONDITION LONG in which the $M_1$ field is nonzero, and the $RI_2$ field contains a positive value that does not cause address wraparound.

COMPARE AND BRANCH RELATIVE, COMPARE IMMEDIATE AND BRANCH RELATIVE, COMPARE LOGICAL AND BRANCH RELATIVE, and COMPARE LOGICAL IMMEDIATE AND BRANCH RELATIVE in which the $M_3$ field is nonzero and the $RI_4$ field contains a positive value. (That is, only forward branches with nonzero branch masks.)

c. Except for TRANSACTION END and instructions which cause a specified operand serialization, instructions which cause a serialization function are restricted.

d. Storage-and-storage operations (SS-), and storage-and-storage operations with an extended opcode (SSE-) instructions are restricted.

e. All of the following general instructions (which are of the z/Architecture in this example) are restricted: CHECKSUM; CIPHER MESSAGE; CIPHER MESSAGE WITH CFB; CIPHER MESSAGE WITH CHAINING; CIPHER MESSAGE WITH COUNTER; CIPHER MESSAGE WITH OFB; COMPARE AND FORM CODEWORD; COMPARE LOGICAL LONG; COMPARE LOGICAL LONG EXTENDED; COMPARE LOGICAL LONG UNICODE; COMPARE LOGICAL STRING; COMPARE UNTIL SUBSTRING EQUAL; COMPRESSION CALL; COMPUTE INTERMEDIATE MESSAGE DIGEST; COMPUTE LAST MESSAGE DIGEST; COMPUTE MESSAGE AUTHENTICATION CODE; CONVERT TO BINARY; CONVERT TO DECIMAL; CONVERT UNICODE-16 TO UNICODE-32; CONVERT UNICODE-16 TO UNICODE-8; CONVERT UNICODE-32 TO UNICODE-16; CONVERT UNICODE-32 TO UNICODE-8; CONVERT UNICODE-8 TO UNICODE-16; CONVERT UNICODE-8 TO UNICODE-32; DIVIDE; DIVIDE LOGICAL; DIVIDE SINGLE; EXECUTE; EXECUTE RELATIVE LONG; EXTRACT CACHE ATTRIBUTE; EXTRACT CPU TIME; EXTRACT PSW; EXTRACT TRANSACTION NESTING DEPTH; LOAD AND ADD; LOAD AND ADD LOGICAL; LOAD AND AND; LOAD AND EXCLUSIVE OR; LOAD AND OR; LOAD PAIR DISJOINT; LOAD PAIR FROM QUADWORD; MONITOR CALL; MOVE LONG; MOVE LONG EXTENDED; MOVE LONG UNICODE; MOVE STRING; NON-TRANSACTIONAL STORE; PERFORM CRYPTOGRAPHIC COMPUTATION; PREFETCH DATA; PREFETCH DATA RELATIVE LONG; RUNTIME INSTRUMENTATION EMIT; RUNTIME INSTRUMENTATION NEXT; RUNTIME INSTRUMENTATION OFF; RUNTIME INSTRUMENTATION ON; SEARCH STRING; SEARCH; STRING UNICODE; SET ADDRESSING MODE; STORE CHARACTERS UNDER MASK HIGH, when the $M_3$ field is zero, and the code in the $R_1$ field is 6 or 7; STORE CLOCK; STORE CLOCK EXTENDED; STORE CLOCK FAST; STORE FACILITY LIST EXTENDED; STORE PAIR TO QUADWORD; TEST ADDRESSING MODE; TRANSACTION ABORT; TRANSACTION BEGIN (both TBEGIN and TBEGINC); TRANSLATE AND TEST EXTENDED; TRANSLATE AND TEST REVERSE EXTENDED; TRANSLATE EXTENDED; TRANSLATE ONE TO ONE; TRANSLATE ONE TO TWO TRANSLATE TWO TO ONE; and TRANSLATE TWO TO TWO.
4. The transaction's storage operands access no more than four octowords. Note: LOAD ON CONDITION and STORE ON CONDITION are considered to reference storage regardless of the condition code. An octoword is, for instance, a group of 32 consecutive bytes on a 32 byte boundary.
5. The transaction executing on this CPU, or stores by other CPUs or the I/O subsystem, do not access storage operands in any 4 K-byte blocks that contain the 256 bytes of storage beginning with the TRANSACTION BEGIN constrained (TBEGINC) instruction.
6. The transaction does not access instructions or storage operands using different logical addresses that are mapped to the same absolute address.
7. Operand references made by the transaction are to be within a single doubleword, except that for LOAD ACCESS MULTIPLE, LOAD MULTIPLE, LOAD MULTIPLE HIGH, STORE ACCESS MULTIPLE, STORE MULTIPLE, and STORE MULTIPLE HIGH, operand references are to be within a single octoword.

If a constrained transaction violates any of constraints 1-7, listed above, then either (a) a transaction constraint program interruption is recognized, or (b) execution proceeds as if the transaction was not constrained, except that further constraint violations may still result in a transaction constrained program interruption. It is unpredictable which action is taken, and the action taken may differ based on which constraint is violated.

In the absence of constraint violations, repeated interruptions, or conflicts with other CPUs or the I/O subsystem, a constrained transaction will eventually complete, as described above.
1. The chance of successfully completing a constrained transaction improves if the transaction meets the following criteria:
   a. The instructions issued are fewer than the maximum of 32.
   b. The storage operand references are fewer than the maximum of 4 octowords.
   c. The storage operand references are on the same cache line.
   d. Storage operand references to the same locations occur in the same order by all transactions.
2. A constrained transaction is not necessarily assured of successfully completing on its first execution. However, if a constrained transaction that does not violate any of the listed constraints is aborted, the CPU employs circuitry to ensure that a repeated execution of the transaction is subsequently successful.
3. Within a constrained transaction, TRANSACTION BEGIN is a restricted instruction, thus a constrained transaction cannot be nested.
4. Violation of any of constrains 1-7 above by a constrained transaction may result in a program loop.
5. The limitations of a constrained transaction are similar to those of a compare-and-swap loop. Because of potential interference from other CPUs and the I/O subsystem, there is no architectural assurance that a COMPARE AND SWAP instruction will ever complete with condition code 0. A constrained transaction may suffer from similar interference in the form of fetch- or store-conflict aborts or hot interruptions.

The CPU employs fairness algorithms to ensure that, in the absence of any constraint violations, a constrained transaction eventually completes.
6. In order to determine the number of repeated iterations required to complete a constrained transaction, the program may employ a counter in a general register that is not subject to the general register save mask. An example is shown below.

|      | LH1     | 15,0        | Zero retry counter. |
|------|---------|-------------|---------------------|
| Loop | TBEGINC | 0(0),X 'FE00' | Preserve GRs 0-13 |
|      | AHI     | 15,1        | Increment counter   |
|      | ...     |             |                     |
|      | ...     |             | Constrained transactional-execution code |
|      | ...     |             |                     |
|      | TEND    |             | End of transaction. |

* R15 now contains count of repeated transactional attempts.

Note that both registers 14 and 15 are not restored in this example. Also note that on some models, the count in general register 15 may be low if the CPU detects the abort condition following the completion of the TBEGINC instruction, but before the completion of the AHI instruction.

As observed by the CPU, fetches and stores made in the transactional execution mode are no different than those made while not in the transaction execution mode.

In one embodiment, the user (i.e., the one creating the transaction) selects whether or not a transaction is to be constrained. One embodiment of the logic associated with the processing of constrained transactions, and, in particular, the processing associated with a TBEGINC instruction, is described with reference to FIG. 11. Execution of the TBEGINC instruction causes the CPU to enter the constrained transactional execution mode or remain in the nonconstrained execution mode. The CPU (i.e., the processor) executing TBEGINC performs the logic of FIG. 11.

Figure 11:
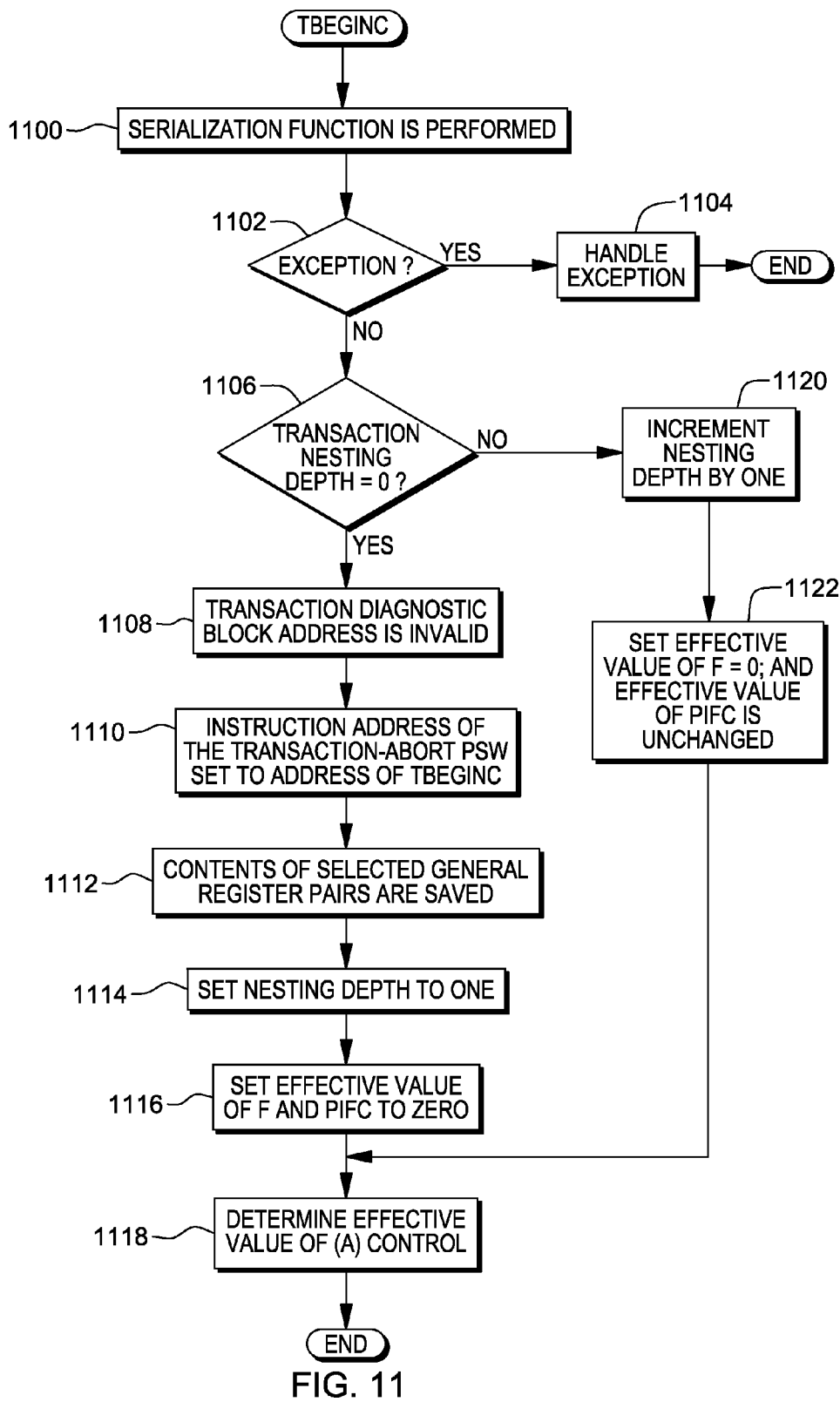
FIG. 11 depicts one embodiment of the logic associated with executing a TBEGINC instruction.

Referring to FIG. 11, based on execution of a TBEGINC instruction, a serialization function is performed, STEP 1100. A serialization function or operation includes completing all conceptually previous storage accesses (and, for the z/Architecture, as an example, related reference bit and change bit settings) by the CPU, as observed by other CPUs and by the I/O subsystem, before the conceptually subsequent storage accesses (and related reference bit and change bit settings) occur. Serialization affects the sequence of all CPU accesses to storage and to the storage keys, except for those associated with ART table entry and DAT table entry fetching.

As observed by a CPU in the transactional execution mode, serialization operates normally (as described above). As observed by other CPUs and by the I/O subsystem, a serializing operation performed while a CPU is in the transactional execution mode occurs when the CPU leaves the transactional execution mode, either as a result of a TRANSAC- TION END instruction that decrements the transaction nesting depth to zero (normal ending), or as a result of the transaction being aborted.

Subsequent to performing serialization, a determination is made as to whether an exception is recognized, INQUIRY 1102. If so, the exception is handled, STEP 1104. For instance, a special operation exception is recognized and the operation is suppressed if the transactional execution control, bit 8 of control register 0, is 0. As further examples, a specification exception is recognized and the operation is suppressed, if the $B_1$ field, bits 16-19 of the instruction, is nonzero; an execute exception is recognized and the operation is suppressed, if the TBEGINC is the target of an execute-type instruction; and an operation exception is recognized and the operation is suppressed, if the transactional execution facility is not installed in the configuration. If the CPU is already in the constrained transaction execution mode, then a transaction constrained exception program exception is recognized and the operation is suppressed. Further, if the transaction nesting depth, when incremented by 1, would exceed a model dependent maximum transaction nesting depth, the transaction is aborted with abort code 13. Other or different exceptions may be recognized and handled.

However, if there is not an exception, then a determination is made as to whether the transaction nesting depth is zero, INQUIRY 1106. If the transaction nesting depth is zero, then the transaction diagnostic block address is considered to be invalid, STEP 1108; the transaction abort PSW is set from the contents of the current PSW, except that the instruction address of the transaction abort PSW designates the TBEGINC instruction, rather than the next sequential instruction, STEP 1110; and the contents of the general register pairs as designated by the general register save mask are saved in a model dependent location that is not directly accessible by the program, STEP 1112. Further, the nesting depth is set to 1, STEP 1114. Additionally, the effective value of the allow floating point operation (F) and program interruption filtering controls (PIFC) are set to zero, STEP 1316. Further, the effective value of the allow AR modification (A) control, bit 12 field of the $I_2$ field of the instruction, is determined, STEP 1118. For example, the effective A control is the logical AND of the A control in the TBEGINC instruction for the current level and for any outer TBEGIN instructions.

Returning to INQUIRY 1106, if the transaction nesting depth is greater than zero, then the nesting depth is incremented by 1, STEP 1120. Further, the effective value of the allow floating point operation (F) is set to zero, and the effective value of the program interruption filtering control (PIFC) is unchanged, STEP 1122. Processing then continues with STEP 1118. In one embodiment, a successful initiation of the transaction results in condition code 0. This concludes one embodiment of the logic associated with executing a TBEGINC instruction.

In one embodiment, the exception checking provided above can occur in varying order. One particular order for the exception checking is as follows:

Exceptions with the same priority as the priority of program interruption conditions for the general case.

Specification exception due to the $B_1$ field containing a nonzero value.

Abort due to exceeding transaction nesting depth.

Condition code 0 due to normal completion.

Additionally, the following applies in one or more embodiments:

1. Registers designated to be saved by the general register save mask are only restored if the transaction aborts, not when the transaction ends normally by means of TRANSACTION END. Only the registers designated by the GRSM of the outermost TRANSACTION BEGIN instruction are restored on abort.

The $I_2$ field should designate all register pairs that provide input values that are changed by a constrained transaction. Thus, if the transaction is aborted, the input register values will be restored to their original contents when the constrained transaction is re-executed.

2. On most models, improved performance may be realized, both on TRANSACTION BEGIN and when a transaction aborts, by specifying the minimum number of registers needed to be saved and restored in the general register save mask.

3. The following illustrates the results of the TRANSACTION BEGIN instruction (both TBEGIN and TBEGINC) based on the current transaction nesting depth (TND) and, when the TND is nonzero, whether the CPU is in the nonconstrained or constrained transactional-execution mode:

| Instruction | TND = 0 | |
|---|---|---|
| TBEGIN | Enter the nonconstrained transactional-execution mode | |
| TBEGINC | Enter the constrained transactional-execution mode | |

| | TND > 0 | |
|---|---|---|
| Instruction | NTX Mode | CTX Mode |
| TBEGIN | Continue in the nonconstrained transactional-execution mode | Transaction-constrained exception |
| TBEGINC | Continue in the nonconstrained transactional-execution mode | Transaction-constrained exception |

Explanation:
CTX CPU is in the constrained transactional-execution mode
NTX CPU is in the nonconstrained transactional-execution mode
TND Transaction nesting depth at the beginning of the instruction.

As described herein, in one aspect, a constrained transaction is assured of completion, assuming it does not contain a condition that makes it unable to complete. To ensure it completes, the processor (e.g., CPU) executing the transaction may take certain actions. For instance, if a constrained transaction has an abort condition, the CPU may temporarily:

(a) inhibit out-of-order execution;

(b) inhibit other CPUs from accessing the conflicting storage locations;

(c) induce random delays in abort processing; and/or (d) invoke other measures to facilitate successful completion.

To summarize, processing of a constrained transaction is, as follows:

If already in the constrained-TX mode, a transaction-constrained exception is recognized.

If current TND (Transaction Nesting Depth)>0, execution proceeds as if nonconstrained transaction Effective F control set to zero Effective PIFC is unchanged Allows outer nonconstrained TX to call service function that may or may not use constrained TX.

If current TND=0:

Transaction diagnostic block address is invalid

No instruction-specified TDB stored on abort

Transaction-abort PSW set to address of TBEGINC

Not the next sequential instruction

General-register pairs designated by GRSM saved in a model-dependent location not accessible by program Transaction token optionally formed (from $D_2$ operand). The transaction token is an identifier of the transaction. It may be equal to the storage operand address or another value.

Effective A=TBEGINC A & any outer A

TND incremented

If TND transitions from 0 to 1, CPU enters the constrained TX mode

Otherwise, CPU remains in the nonconstrained TX mode

Instruction completes with CC0

Exceptions:

Specification exception (PIC (Program Interruption Code) 0006) if $B_1$ field is nonzero Special operation exception (PIC 0013 hex) if transaction-execution control (CR0.8) is zero Transaction constraint exception (PIC 0018 hex) if issued in constrained TX mode Operation exception (PIC 0001) if the constrained transactional execution facility is not installed Execute exception (PIC 0003) if the instruction is the target of an execute-type instruction Abort code 13 if nesting depth exceeded Abort conditions in constrained transaction:

Abort PSW points to TBEGINC instruction

Not the instruction following it

Abort condition causes entire TX to be re-driven

No fail path

CPU takes special measures to ensure successful completion on re-drive

Assuming no persistent conflict, interrupt, or constrained violation, the transaction is assured of eventual completion.

Constraint violation:

PIC 0018 hex—indicates violation of transaction constraint

Or, transaction runs as if nonconstrained

As described above, in addition to constrained transaction processing, which is optional, in one embodiment, the transactional facility also provides nonconstrained transaction processing. Further details regarding the processing of nonconstrained transactions, and, in particular, the processing associated with a TBEGIN instruction are described with reference to FIG. 12. Execution of the TBEGIN instruction causes the CPU either to enter or to remain in the nonconstrained transactional execution mode. The CPU (i.e., the processor) that executes TBEGIN performs the logic of FIG. 12.

Figure 12:
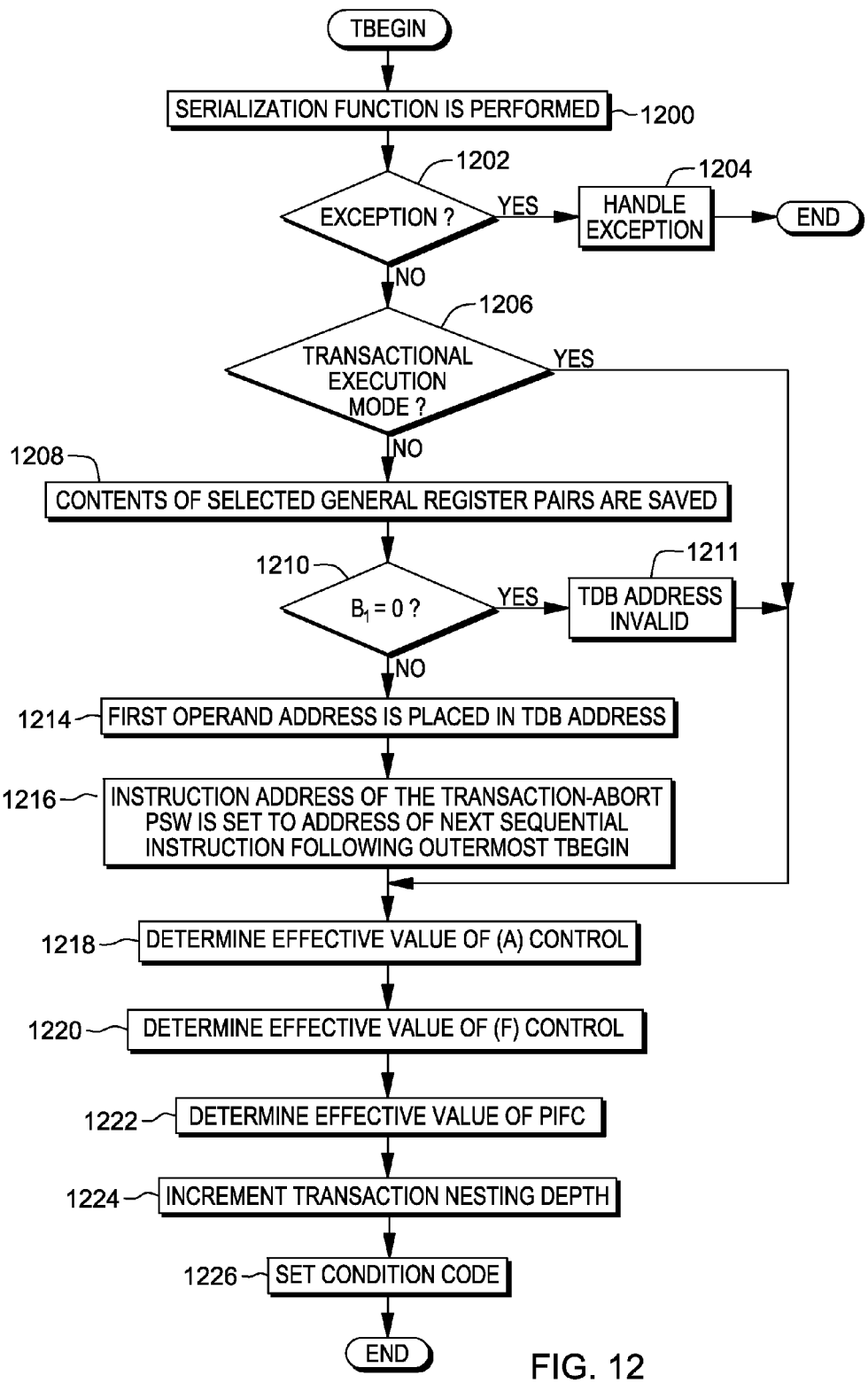
FIG. 12 depicts one embodiment of the logic associated with executing a TBEGIN instruction.

Referring to FIG. 12, based on execution of the TBEGIN instruction, a serialization function (described above) is performed, STEP 1200. Subsequent to performing serialization, a determination is made as to whether an exception is recognized, INQUIRY 1202. If so, then the exception is handled, STEP 1204. For instance, a special operation exception is recognized and the operation is suppressed if the transactional execution control, bit 8 of control register 0, is zero. Further, a specification exception is recognized and the operation is suppressed if the program interruption filtering control, bits 14-15 of the $I_2$ field of the instruction, contains the value 3; or the first operand address does not designate a double word boundary. An operation exception is recognized and the operation is suppressed, if the transactional execution facility is not installed in the configuration; and an execute exception is recognized and the operation is suppressed if the TBEGIN is the target of an execute-type instruction. Additionally, if the CPU is in the constrained transactional execution mode, then a transaction constrained exception program exception is recognized and the operation is suppressed. Further, if the transaction nesting depth, when incremented by 1, would exceed a model dependent maximum transaction nesting depth, the transaction is aborted with abort code 13.

Yet further, when the $B_1$ field of the instruction is nonzero and the CPU is not in the transactional execution mode, i.e., the transaction nesting depth is zero, then the store accessibility to the first operand is determined. If the first operand cannot be accessed for stores, then an access exception is recognized and the operation is either nullified, suppressed, or terminated, depending on the specific access-exception condition. Additionally, any PER storage alteration event for the first operand is recognized. When the $B_1$ field is nonzero and the CPU is already in the transactional execution mode, it is unpredictable whether store accessibility to the first operand is determined, and PER storage alteration events are detected for the first operand. If the $B_1$ field is zero, then the first operand is not accessed.

In addition to the exception checking, a determination is made as to whether the CPU is in the transactional execution mode (i.e., transaction nesting depth is zero), INQUIRY 1206. If the CPU is not in the transactional execution mode, then the contents of selected general register pairs are saved, STEP 1208. In particular, the contents of the general register pairs designated by the general register save mask are saved in a model dependent location that is not directly accessible by the program.

Further, a determination is made as to whether the $B_1$ field of the instruction is zero, INQUIRY 1210. If the $B_1$ field is not equal to zero, the first operand address is placed in the transaction diagnostic block address, STEP 1214, and the transaction diagnostic block address is valid. Further, the transaction abort PSW is set from the contents of the current PSW, STEP 1216. The instruction address of the transaction abort PSW designates the next sequential instruction (that is, the instruction following the outermost TBEGIN).

Moreover, a determination is made of the effective value of the allow AR modification (A) control, bit 12 of the $I_2$ field of the instruction, STEP 1218. The effective A control is the logical AND of the A control in the TBEGIN instruction for the current level and for all outer levels. Additionally, an effective value of the allow floating point operation (F) control, bit 13 of the $I_2$ field of the instruction, is determined, STEP 1220. The effective F control is the logical AND of the F control in the TBEGIN instruction for the current level and for all outer levels. Further, an effective value of the program interruption filtering control (PIFC), bits 14-15 of the $I_2$ field of the instruction, is determined, STEP 1222. The effective PIFC value is the highest value in the TBEGIN instruction for the current level and for all outer levels.

Additionally, a value of one is added to the transaction nesting depth, STEP 1224, and the instruction completes with setting condition code 0, STEP 1226. If the transaction nesting depth transitions from zero to one, the CPU enters the nonconstrained transactional execution mode; otherwise, the CPU remains in the nonconstrained transactional execution mode.

Returning to INQUIRY 1210, if $B_1$ is equal to zero, then the transaction diagnostic block address is invalid, STEP 1211, and processing continues with STEP 1218. Similarly, if the CPU is in transactional execution mode, INQUIRY 1206, processing continues with STEP 1218.

Resulting Condition Code of execution of TBEGIN include, for instance:

0 Transaction initiation successful

1 --

2 --

3 --

Program Exceptions include, for instance:
Access (store, first operand)
Operation (transactional execution facility not installed)
Special operation
Specification
Transaction constraint (due to restricted instruction)

In one embodiment, the exception checking provided above can occur in varying order. One particular order to the exception checking is as follows:

Exceptions with the same priority as the priority of program interruption conditions for the general case.
Specification exception due to reserved PIFC value.
Specification exception due to first operand address not on a doubleword boundary.
Access exception (when $B_1$ field is nonzero).
Abort due to exceeding maximum transaction nesting depth.
Condition code 0 due to normal completion.

Notes:
1. When the $B_1$ field is nonzero, the following applies:
   An accessible transaction diagnostic block (TDB) is to be provided when an outermost transaction is initiated—even if the transaction never aborts.
   Since it is unpredictable whether accessibility of the TDB is tested for nested transactions, an accessible TDB should be provided for any nested TBEGIN instruction.
   The performance of any TBEGIN in which the $B_1$ field is nonzero, and the performance of any abort processing that occurs for a transaction that was initiated by an outermost TBEGIN in which the $B_1$ field is nonzero, may be slower than when the $B_1$ field is zero.
2. Registers designated to be saved by the general register save mask are only restored, in one embodiment, if the transaction aborts, not when the transaction ends normally by means of TRANSACTION END. Only the registers designated by the GRSM of the outermost TRANSACTION BEGIN instruction are restored on abort.
   The $I_2$ field should designate all register pairs that provide input values that are changed by the transaction. Thus, if the transaction is aborted, the input register values will be restored to their original contents when the abort handler is entered.
3. The TRANSACTION BEGIN (TBEGIN) instruction is expected to be followed by a conditional branch instruction that will determine whether the transaction was successfully initiated.
4. If a transaction is aborted due to conditions that do not result in an interruption, the instruction designated by the transaction abort PSW receives control (that is, the instruction following the outermost TRANSACTION BEGIN (TBEGIN)). In addition to the condition code set by the TRANSACTION BEGIN (TBEGIN) instruction, condition codes 1-3 are also set when a transaction aborts.
   Therefore, the instruction sequence following the outermost TRANSACTION BEGIN (TBEGIN) instruction should be able to accommodate all four condition codes, even though the TBEGIN instruction only sets code 0, in this example.
5. On most models, improved performance may be realized, both on TRANSACTION BEGIN and when a transaction aborts, by specifying the minimum number of registers needed to be saved and restored in the general register save mask.
6. While in the nonconstrained transactional execution mode, a program may call a service function which may alter access registers or floating point registers (including the floating point control register). Although such a service routine may save the altered registers on entry and restore them at exit, the transaction may be aborted prior to normal exit of the routine. If the calling program makes no provision for preserving these registers while the CPU is in the nonconstrained transactional execution mode, it may not be able to tolerate the service function's alteration of the registers.
   To prevent inadvertent alteration of access registers while in the nonconstrained transactional execution mode, the program can set the allow AR modification control, bit 12 of the $I_2$ field of the TRANSACTION BEGIN instruction, to zero. Similarly, to prevent the inadvertent alteration of the floating point registers, the program can set the allow floating point operation control, bit 13 of the $I_2$ field of the TBEGIN instruction, to zero.
7. Program exception conditions recognized during execution of the TRANSACTION BEGIN (TBEGIN) instruction are subject to the effective program interruption filtering control set by any outer TBEGIN instructions. Program exception conditions recognized during the execution of the outermost TBEGIN instruction are not subject to filtering.
8. In order to update multiple storage locations in a serialized manner, conventional code sequences may employ a lock word (semaphore). If (a) transactional execution is used to implement updates of multiple storage locations, (b) the program also provides a "fall-back" path to be invoked if the transaction aborts, and (c) the fallback path employs a lock word, then the transactional execution path should also test for the availability of the lock, and, if the lock is unavailable, end the transaction by means of the TRANSACTION END instruction and branch to the fall back path. This ensures consistent access to the serialized resources, regardless of whether they are updated transactionally.
   Alternatively, the program could abort if the lock is unavailable, however the abort processing may be significantly slower than simply ending the transaction via TEND.
9. If the effective program interruption filtering control (PIFC) is greater than zero, the CPU filters most data exception program interruptions. If the effective allow floating point operation (F) control is zero, the data exception code (DXC) will not be set in the floating point control register as a result of an abort due to a data exception program exception condition. In this scenario (filtering applies and the effective F control is zero), the only location in which the DXC is inspected is in the TBEGIN-specified TDB. If the program's abort handler is to inspect the DXC in such a situation, general register $B_1$ should be nonzero, such that a valid transaction diagnostic block address (TDBA) is set.
10. If a PER storage alteration or zero address detection condition exists for the TBEGIN-specified TDB of the outermost TBEGIN instruction, and PER event suppression does not apply, the PER event is recognized during the execution of the instruction, thus causing the transaction to be aborted immediately, regardless of whether any other abort condition exists.

In one embodiment, the TBEGIN instruction implicitly sets the transaction abort address to be the next sequential instruction following the TBEGIN. This address is intended to be a conditional branch instruction which determines whether or not to branch depending on the condition code (CC). A successful TBEGIN sets CC0, whereas an aborted transaction sets CC1, CC2, or CC3.

In one embodiment, the TBEGIN instruction provides an optional storage operand designating the address of a transaction diagnostic block (TDB) into which information is stored if the transaction is aborted.

Further, it provides an immediate operand including the following:

A general register save mask (GRSM) indicating which pairs of general registers are to be saved at the beginning of transactional execution and restored if the transaction is aborted;

A bit (A) to allow aborting of the transaction if the transaction modifies access registers;

A bit (F) to allow aborting of the transaction if the transaction attempts to execute floating point instructions; and A program interruption filtering control (PIFC) that allows individual transaction levels to bypass the actual presentation of a program interruption if a transaction is aborted.

The A, F, and PIFC controls can be different at various nesting levels and restored to the previous level when inner transaction levels are ended.

Moreover, the TBEGIN (or in another embodiment, TBEGINC) is used to form a transaction token. Optionally, the token may be matched with a token formed by the TEND instruction. For each TBEGIN (or TBEGINC) instruction, as an example, a token is formed from the first operand address. This token may be formed independent of whether the base register is zero (unlike TDB address setting which only occurs when the base register is nonzero). For each TRANSACTION END instruction executed with a nonzero base register, a similar token is formed from its storage operand. If the tokens do not match, a program exception may be recognized to alert the program of an unpaired instruction.

Token matching provides a mechanism intended to improve software reliability by ensuring that a TEND statement is properly paired with a TBEGIN (or TBEGINC). When a TBEGIN instruction is executed at a particular nesting level, a token is formed from the storage operand address that identifies this instance of a transaction. When a corresponding TEND instruction is executed, a token is formed from the storage operand address of the instruction, and the CPU compares the begin token for the nesting level with the end token. If the tokens do not match, an exception condition is recognized. A model may implement token matching for only a certain number of nesting levels (or for no nesting levels). The token may not involve all bits of the storage operand address, or the bits may be combined via hashing or other methods. A token may be formed by the TBEGIN instruction even if its storage operand is not accessed.

To summarize, processing of a nonconstrained transaction is, as follows:

If TND=0:
    If $B_1 \neq 0$, transaction diagnostic block address set from first operand address.
    Transaction abort PSW set to next sequential instruction address.
    General register pairs designated by $I_2$ field are saved in model-dependent location.
    Not directly accessible by the program
Effective PIFC, A, & F controls computed
    Effective A=TBEGIN A & any outer A
    Effective F=TBEGIN F & any outer F
    Effective PIFC=max(TBEGIN PIFC, any outer PIFC)

Transaction nesting depth (TND) incremented
If TND transitions from 0 to 1, CPU enters the transactional execution mode
Condition code set to zero
    When instruction following TBEGIN receives control:
        TBEGIN success indicated by CC0
        Aborted transaction indicated by nonzero CC
Exceptions:
    Abort code 13 if nesting depth exceeded
    Access exception (one of various PICs) if the $B_1$ field is nonzero, and the storage operand cannot be accessed for a store operation
    Execute exception (PIC 0003) if the TBEGIN instruction is the target of an execute-type instruction
    Operation exception (PIC 0001) if the transactional execution facility is not installed
    PIC 0006 if either
        PIFC is invalid (value of 3)
        Second-operand address not doubleword aligned
    PIC 0013 hex if transactional-execution control (CR0.8) is zero
    PIC 0018 hex if issued in constrained TX mode As indicated above, a transaction, either constrained or nonconstrained, may be ended by a TRANSACTION END (TEND) instruction. Further details regarding the processing of a transaction end (TEND) instruction are described with reference to FIG. 13. The CPU (i.e., the processor) executing the TEND performs the logic of FIG. 13.

Figure 13:
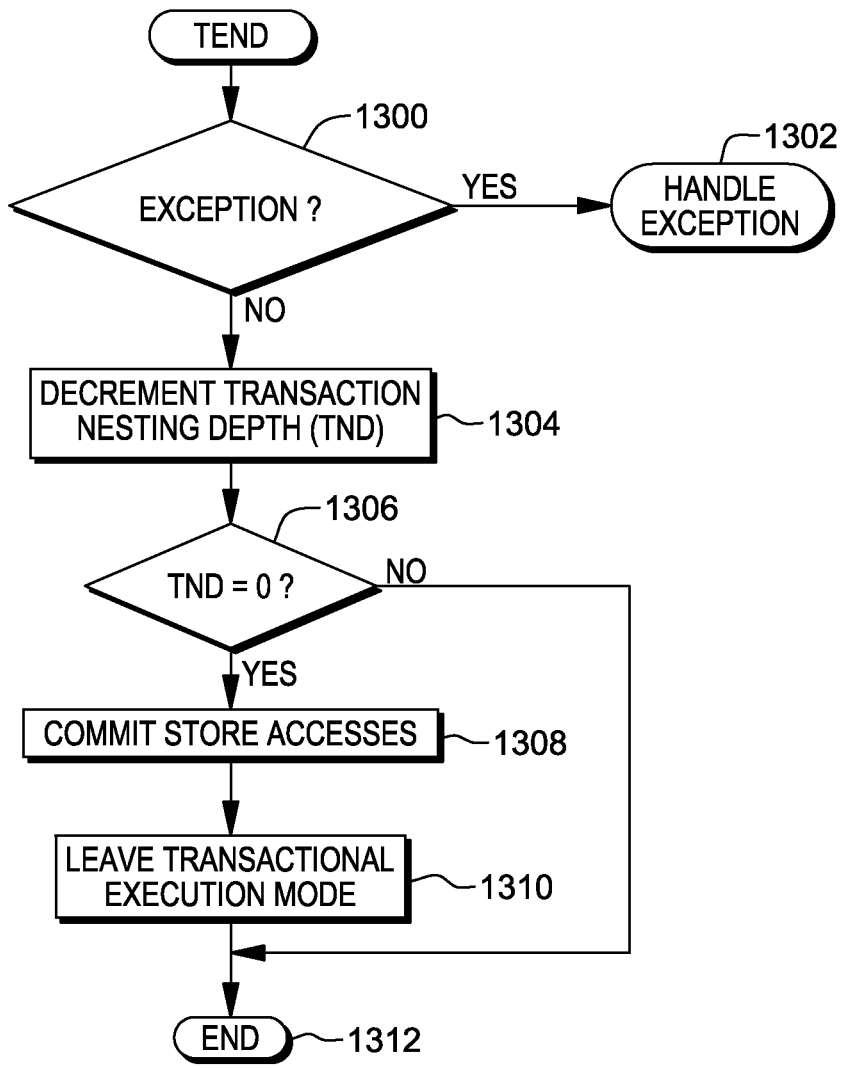
FIG. 13 depicts one embodiment of the logic associated with executing a TEND instruction.

Referring to FIG. 13, initially, based on the processor obtaining (e.g., fetching, receiving, etc.) the TEND instruction, various exception checking is performed and if there is an exception, INQUIRY 1300, then the exception is handled, STEP 1302. For instance, if the TRANSACTION END is the target of an execute-type instruction, the operation is suppressed and an execute exception is recognized; and a special operation exception is recognized and the operation is suppressed if the transactional execution control, bit 8 of CR0, is zero. Yet further, an operation exception is recognized and the operation is suppressed, if the transactional execution facility is not installed in the configuration.

Returning to INQUIRY 1300, if an exception is not recognized, then the transaction nesting depth is decremented (e.g., by one), STEP 1304. A determination is made as to whether the transactional nesting depth is zero following the decrementing, INQUIRY 1306. If the transaction nesting depth is zero, then all store accesses made by the transaction (and other transactions within the nest of transactions, if any, of which this transaction is a part) are committed, STEP 1308. Further, the CPU leaves the transactional execution mode, STEP 1310, and the instruction completes, STEP 1312.

Returning to INQUIRY 1306, if the transaction nesting depth is not equal to zero, then the TRANSACTION END instruction just completes.

If the CPU is in the transaction execution mode at the beginning of the operation, the condition code is set to 0; otherwise, the condition code is set to 2.

It is noted that the effective allow floating point operation (F) control, allow AR modification (A) control, and program interruption filtering control (PIFC) are reset to their respective values prior to the TRANSACTION BEGIN instruction that initiated the level being ended. Further, a serialization function is performed at the completion of the operation.

The PER instruction fetching and transaction end events that are recognized at the completion of the outermost TRANSACTION END instruction do not result in the transaction being aborted.

In one example, the TEND instruction also includes a base field B$_2$ and a displacement field D$_2$, which are combined (e.g., added) to create a second operand address. In this example, token matching may be performed. For instance, when B$_2$ is nonzero, selected bits of the second operand address are matched against a transaction token formed by the corresponding TBEGIN. If there is a mismatch, there is an exception (e.g., PIC 0006).

In addition to the above, a transaction may be aborted implicitly or explicitly by a TRANSACTION ABORT instruction. Aborting a transaction by TABORT or otherwise includes performing a number of steps. An example of the steps for abort processing, in general, is described with reference to FIG. 14. If there is a difference in processing based on whether the abort is initiated by TABORT or otherwise, it is indicated in the description below. In one example, a processor (e.g., CPU) is performing the logic of FIG. 14.

Figure 14:
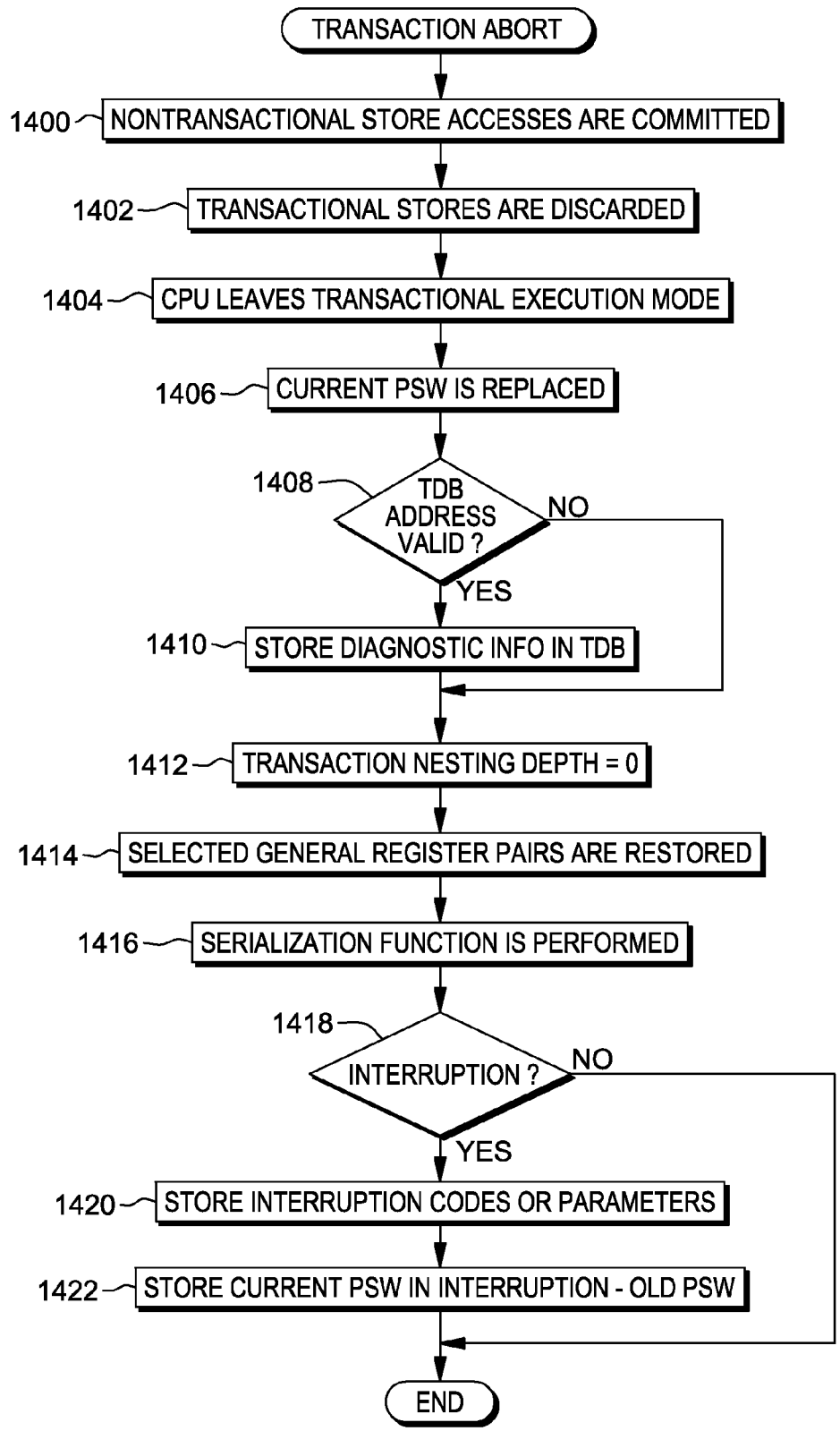
FIG. 14 depicts one embodiment of the logic associated with transaction abort processing.

Referring to FIG. 14, initially, based on execution of the TABORT instruction or an implicit abort, non-transactional store accesses made while the CPU was in the transactional execution mode are committed, STEP 1400. Other stores (e.g., transactional stores) made while the CPU was in the transactional execution mode are discarded, STEP 1402.

The CPU leaves the transactional execution mode, STEP 1404, and subsequent stores occur non-transactionally. The current PSW is replaced with the contents of the transaction abort PSW, except that the condition code is set as described above (other than the situation below, in which if TDBA is valid, but the block is inaccessible, then CC=1), STEP 1406. As a part of or subsequent to abort processing, processing branches to the transaction abort PSW specified location to perform an action. In one example in which the transaction is a constrained transaction, the location is the TBEGINC instruction and the action is re-execution of that instruction; and in a further example in which the transaction is a nonconstrained transaction, the location is the instruction after TBEGIN, and the action is execution of that instruction, which may be, for instance, a branch to an abort handler.

Next, a determination is made as to whether the transaction diagnostic block address is valid, INQUIRY 1408. When the transaction diagnostic block address is valid, diagnostic information identifying the reason for the abort and the contents of the general registers are stored into the TBEGIN-specified transaction diagnostic block, STEP 1410. The TDB fields stored and conditions under which they are stored are described above with reference to the transaction diagnostic block.

If the transaction diagnostic block address is valid, but the block has become inaccessible, subsequent to the execution of the outermost TBEGIN instruction, the block is not accessed, and condition code 1 applies.

For transactions that are aborted due to program exception conditions that result in an interruption, the program interruption TDB is stored.

Returning to INQUIRY 1408, if the transaction diagnostic block address is not valid, no TBEGIN-specified TDB is stored and condition code 2 or 3 applies, depending on the reason for aborting.

In addition to the above, the transaction nesting depth is set equal to zero, STEP 1412. Further, any general register pairs designated to be saved by the outermost TBEGIN instruction are restored, STEP 1414. General register pairs that were not designated to be saved by the outermost TBEGIN instruction are not restored when a transaction is aborted.

Further, a serialization function is performed, STEP 1416. A serialization function or operation includes completing all conceptually previous storage accesses (and, for the z/Architecture, as an example, related reference bit and change bit settings) by the CPU, as observed by other CPUs and by the I/O subsystem, before the conceptionally subsequent storage accesses (and related reference bit and change bit settings) occur. Serialization effects the sequence of all CPU accesses to storage and to the storage keys, except for those associated with ART table entry and DAT table entry fetching.

As observed by a CPU in the transactional execution mode, serialization operates normally (as described above). As observed by other CPUs and by the I/O subsystem, a serializing operation performed while a CPU is in the transactional execution mode occurs when the CPU leaves the transactional execution mode, either as a result of a TRANSACTION END instruction that decrements the transaction nesting depth to zero (normal ending) or as a result of the transaction being aborted.

For abort processing initiated other than by TABORT, if the transaction is aborted due to an exception condition that results in an interruption, INQUIRY 1418, interruption codes or parameters associated with the interruption are stored at the assigned storage locations corresponding to the type of interruption, STEP 1420. Further, the current PSW, as set above, is stored into the interruption old PSW, STEP 1422. Thereafter, or if the transaction was not aborted due to an exception condition that resulted in an interruption, the instruction ends with condition code zero.

In addition to the above, in one embodiment for interpretive execution of the z/Architecture, when the CPU is in the transactional execution mode, and a guest condition occurs that would normally result in interception codes 4, 12, 44, 56, 64, 68 or 72, interception does not occur. Rather, the CPU remains in the interpretive execution mode, and the abort conditions are indicated to the guest as follows:

For a nonconstrained transaction, the transaction is aborted due to a restricted instruction (abort code 11). If a concurrent PER event was detected and the CPU is enabled for PER, a program interruption occurs with interruption code 0280 hex.

For a constrained transaction, a transaction constraint exception is recognized. If a concurrent PER event was detected and the CPU is enabled for PER, a program interruption occurs with interruption code 0298 hex.

When a transaction is aborted due to a program exception condition, program interruption filtering can inhibit the presentation of an interruption. For program interruptions that can result in interception, filtering also inhibits the interception.

As indicated above, in one embodiment, when a program initiates a nonconstrained transaction (that is, a transaction for which an abort handler recovery routine is provided), the program may designate a storage location into which diagnostic information is to be recorded if the transaction aborts. Diagnostic information may also be provided if a transaction is aborted due to a program interruption or if the abort results in an interpretive execution interception, such as a program-interruption interception.

In one embodiment, based on an abort of a transaction, diagnostic information is provided in a transaction diagnostic block (TDB). The information includes, for instance: transaction nesting depth; transaction abort code; conflict token (for transactions that are aborted due to conflicts); aborting transaction instruction address; program interruption parameters for transactions that are aborted due to filtered program exception conditions; model dependent diagnostic information, including transactional execution branch indications; general purpose registers at the time of the abort; and/or other information, as described above with reference to FIG. 9.

Zero, one or two TDBs may be stored on an abort, including: a program-specified TDB (a.k.a., TBEGIN-TDB) which may or may not be present for a nonconstrained transaction; a program-interruption TDB provided to the control program when a transaction is aborted due to a non-filtered program exception condition (that is, a condition that actually results in a program interruption); and/or an interception TDB provided to a host program (e.g., operating system) when a transaction is aborted due to certain interception conditions.

One embodiment of processing associated with storing zero or more TDBs is described with reference to FIG. 15A. This logic is performed by a processor, such as the processor detecting an abort condition.

Figure 15A:
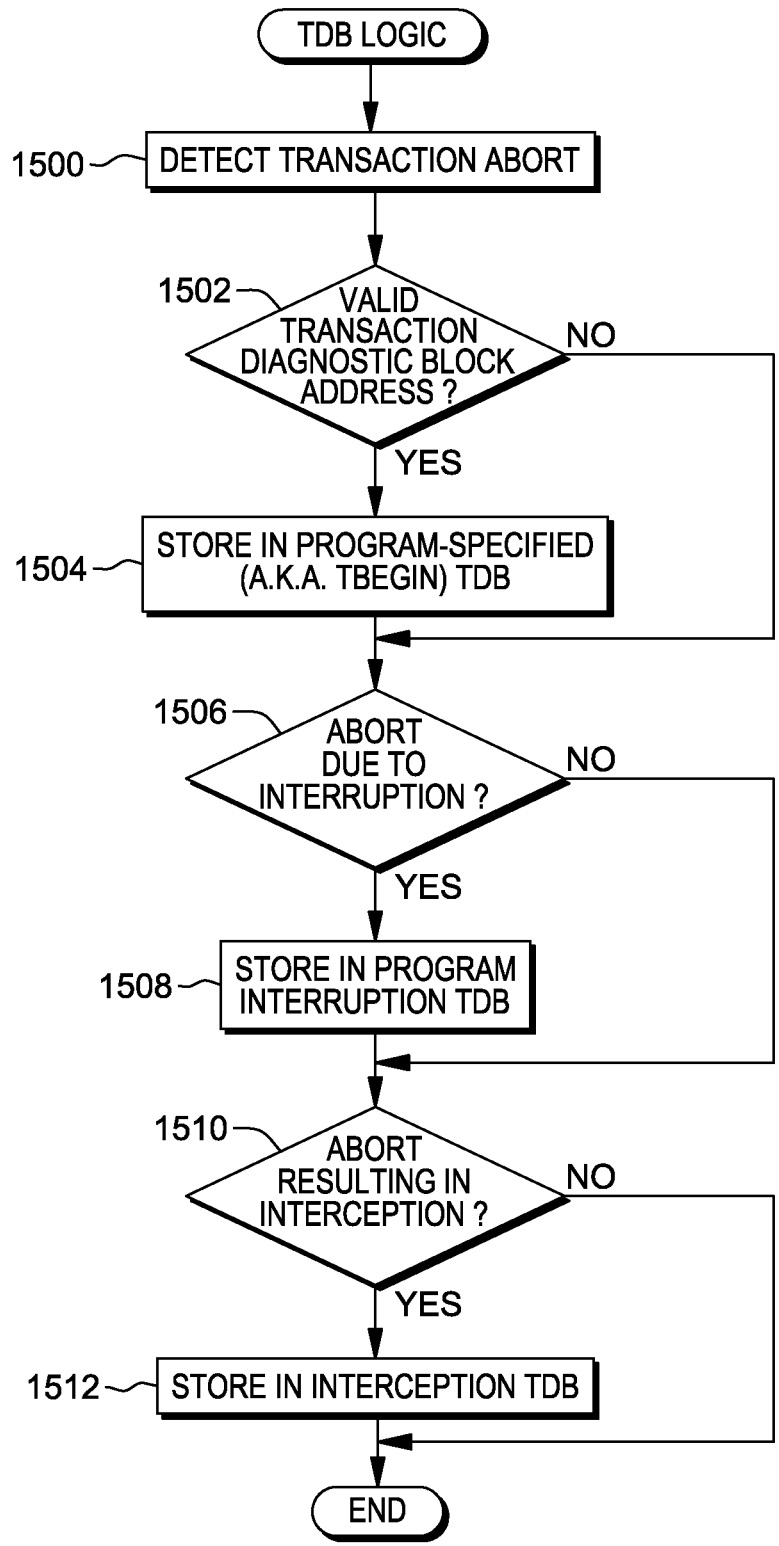
FIG. 15A depicts one embodiment of the logic associated with selectively storing information in one or more transaction diagnostic blocks.

Referring to FIG. 15A, initially an abort (i.e., an abnormal end) of a transaction is detected, STEP 1500. Thereafter, a determination is made as to whether a valid transaction diagnostic block address (TDBA) has been specified, INQUIRY 1502. For instance, is a valid transaction diagnostic block address specified by a TBEGIN instruction (e.g., $B_1$ of TBEGIN>0). If a valid TDBA is provided, information is stored in the program-specified TDB, as described above, STEP 1504.

Thereafter, or if a valid TDBA is not provided, a further determination is made as to whether the abort condition is due to an interruption, INQUIRY 1506. If so, then information is stored in the program interruption TDB, as indicated above, STEP 1508.

Thereafter, or if the abort is not due to a program interruption, a determination is made as to whether the abort resulted in an interception, INQUIRY 1510. If the abort did not result in an interception, this processing is complete. Otherwise, information is stored in an interception TDB, as described above, STEP 1512. This concludes processing.

As indicated herein, one or more TDBs or even no TDBs may be stored as a result of an abort. However, each TDB that is stored provides diagnostic information relating to the abort that may facilitate debugging. In one embodiment, the diagnostic information includes transactional execution branch indications that provided a branch history that may be useful in debugging a failing transaction.

Further details relating to providing branch indications are described with reference to FIG. 15B. In one embodiment, this logic is performed by a processor, such as the processor executing the transaction.

Figure 15B:
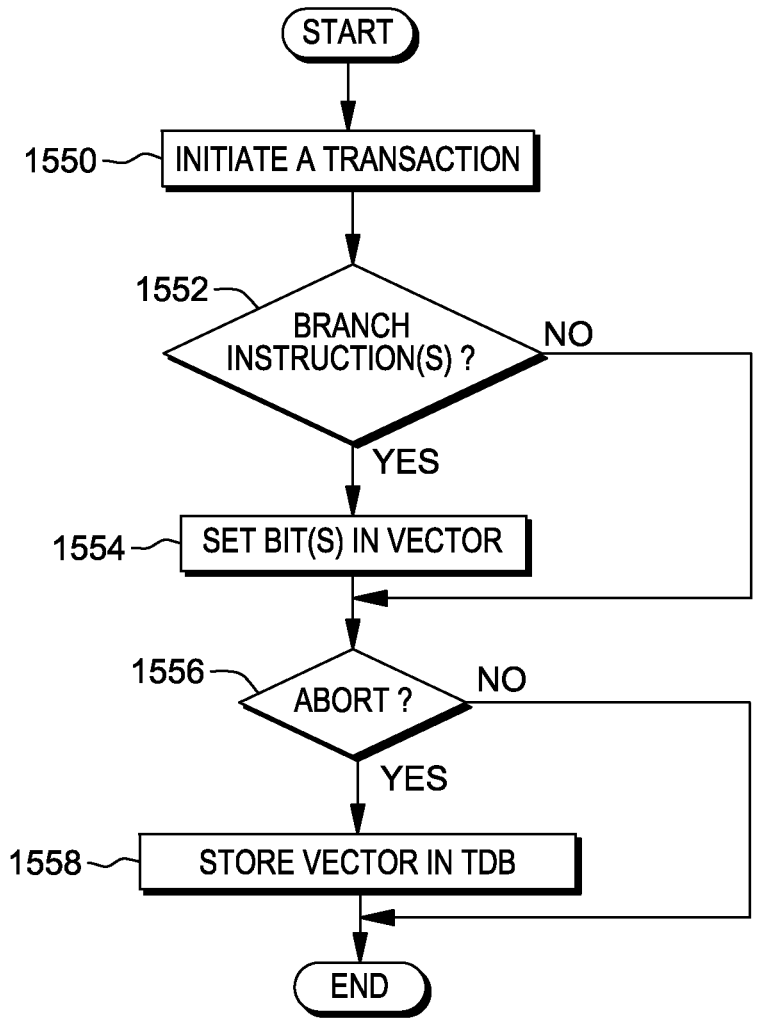
FIG. 15B depicts one embodiment of the logic associated with providing branch indications.

Referring to FIG. 15B, initially, a transaction is initiated via, for instance, a TRANSACTION BEGIN instruction, STEP 1550. In one example, the transaction is a nonconstrained transaction, and therefore, the TBEGIN instruction is employed. During execution of the transaction, a determination is made as to whether one or more branch instructions are executed, INQUIRY 1552. As a branch instruction is encountered, a bit in a vector, called a transactional execution branch indication (TXBI), is set to indicate whether the branch was taken, STEP 1554. If the branch was taken, then the bit is set to, e.g., one; and if the branch was not taken, then the bit is set to, e.g., zero. This is performed for each branch instruction encountered.

In particular, in one example, the vector includes 64 bits. Each of the first 63 bits of the vector indicates the results of executing a branching instruction while the CPU was in the transactional execution mode, as follows: 0—the instruction completed without branching; and 1—the instruction completed with branching. Bit 0 represents the result of the first such branching instruction, bit 1 represents the result of the second such instruction, and so forth. This does not necessarily mean separate branch instructions are present. If the transaction is looping, the same branch may be executed multiple times, resulting in the setting of multiple vector bits.

If fewer than 63 branching instructions are executed while the CPU was in the transactional execution mode, the rightmost bits that do not correspond to branching instructions are set to zeros (including bit 63). When more than 63 branching instructions are executed, bit 63 of the TXBI is set to one. Thus, in one example, if a transaction executed in a straight line of code (that is, no loops) containing lots of branches—none of which were taken—it is possible for the vector to contain all zeros except for the rightmost bit.

If during processing of the transaction, the transaction is aborted, INQUIRY 1556, then, in one example, the vector is stored in a transaction diagnostic block, STEP 1558. In one example, there are a plurality of transaction diagnostic blocks, as described above, and the vector may be stored in zero or more of those blocks depending on the type of abort and/or whether a valid transaction diagnostic block address is provided in the TRANSACTION BEGIN instruction. For instance, if TBEGIN provides a valid TDB address, then the vector is stored in a program-specified TDB, as described above; if the abort was due to an interruption, then the vector is stored in a program interruption TDB, as described above; and/or if the abort results in an interception, then the vector is stored in an interception TDB, as described above.

By providing the bits in a transaction diagnostic block, a branch history is provided that can be used in diagnosing the failed transaction.

In addition to the providing of diagnostic information, as described above, further provided is an efficient means of updating multiple, discontiguous objects in memory without classic (course-grained) serialization, such as locking, that provides a potential for significant multiprocessor performance improvement. That is, multiple, discontiguous objects are updated without the enforcement of more course-grained storage-access ordering that is provided by classic techniques, such as locks and semaphores. Speculative execution is provided without onerous recovery setup, and constrained transactions are offered for simple, small-footprint updates.

Transactional execution can be used in a variety of scenarios, including, but not limited to, partial inlining, speculative processing, and lock elision. In partial inlining, the partial region to be included in the executed path is wrapped in TBEGIN/TEND. TABORT can be included therein to roll back state on a side-exit. For speculation, such as in Java, nullchecks on de-referenced pointers can be delayed to loop edge by using a transaction. If the pointer is null, the transaction can abort safely using TABORT, which is included within TBEGIN/TEND.

As for lock elision, one example of its use is described with reference to FIGS. 16A-16B and the code fragment provided below.

Figure 16A:
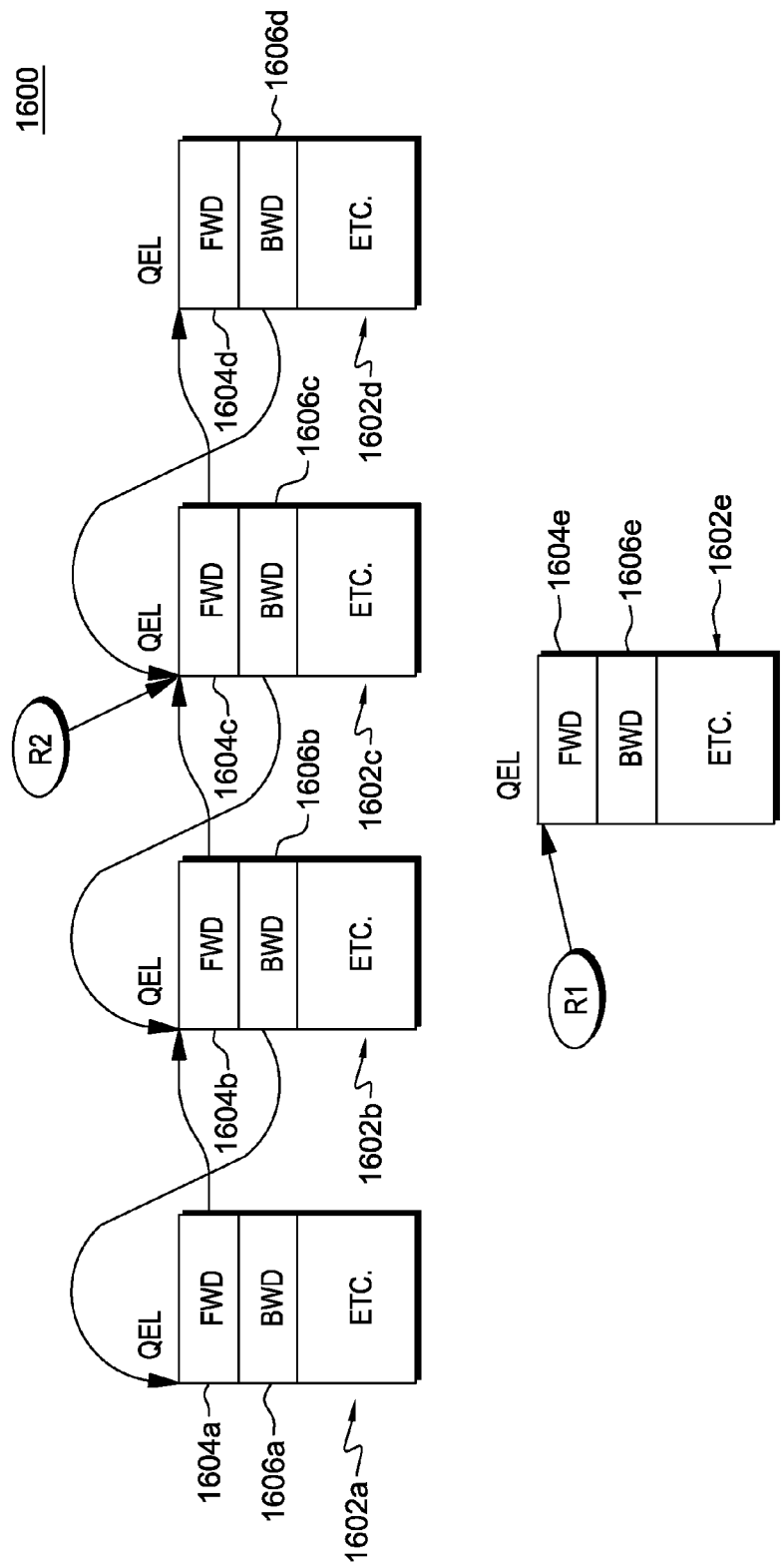
FIGS. 16A-16B depict an example of inserting a queue element into a doubly linked list of queue elements.

FIG. 16A depicts a doubly linked list 1600 of a plurality of queue elements 1602a-1602d. A new queue element 1602e is to be inserted into the doubly linked list of queue elements 1600. Each queue element 1602a-1602e includes a forward pointer 1604a-1604e and a backward pointer 1606a-1606e. As shown in FIG. 16B, to add queue element 1602e between queue elements 1602b and 1602c, (1) backward pointer 1606e is set to point to queue element 1602b, (2) forward pointer 1604e is set to point to queue element 1602c, (3) backward pointer 1606c is set to point to queue element 1602e, and (4) forward pointer 1604b is set to point to queue element 1602e.

Figure 16B:
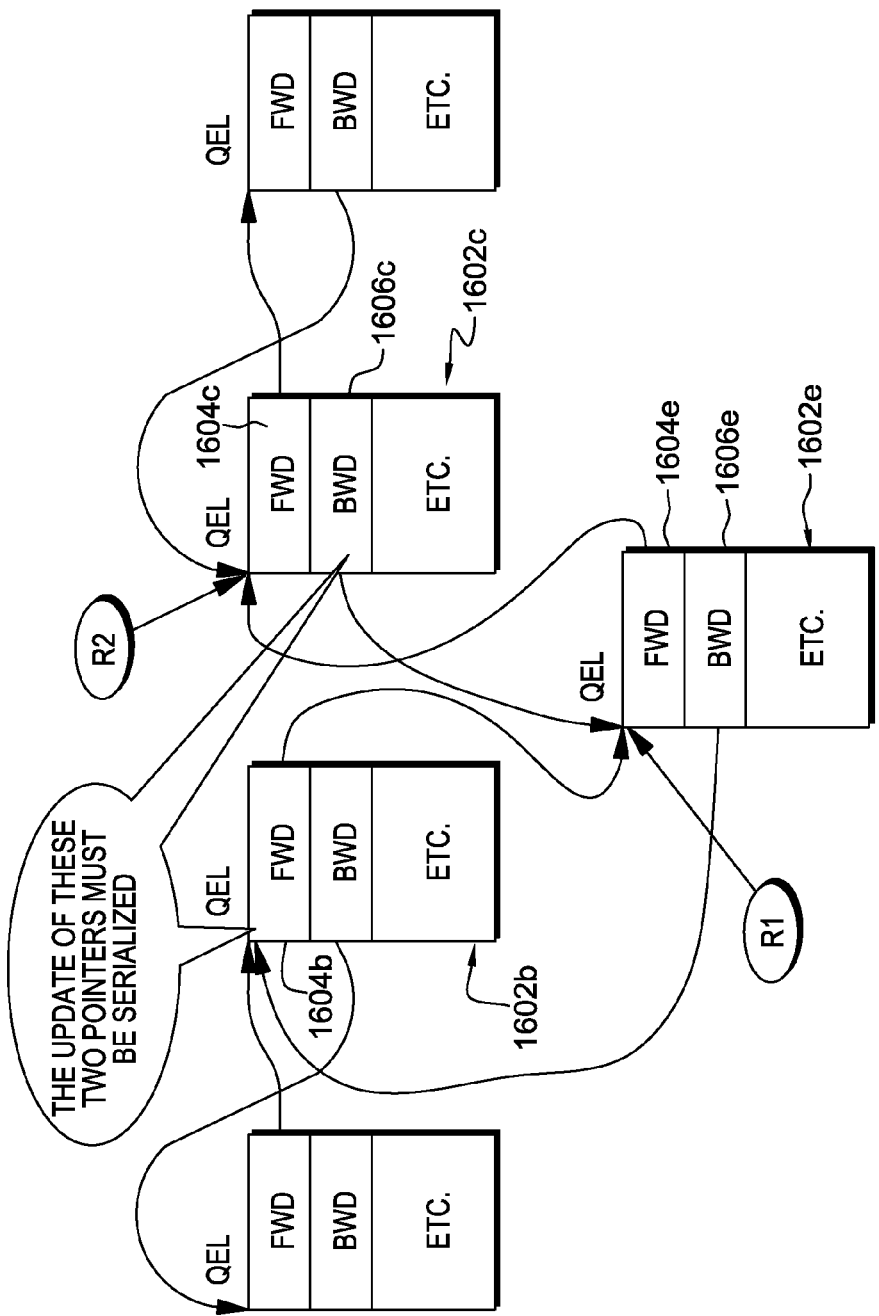

An example code fragment corresponding to FIGS. 16A-16B is below:

| | | | |
|---|---|---|---|
| NEW | USING | QEL, R1 | |
| CURR | USING | QEL, R2 | |
| | LHI | R15, 10 | Load retry count. |
| LOOP | TBEGIN | TDB, X'C000' | Begin transaction (save GRs 0-3) |
| | JNZ | ABORTED | Nonzero CC means aborted. |
| | LG | R3, CURR.BWD | Point to previous element. |
| PREV | USING | QEL, R3 | Make it addressable. |
| | STG | R1, PREV.FWD | Update prev. forward ptr. |
| | STG | R1, CURR.BWD | Update curr. backward ptr. |
| | STG | R2, NEW.FWD | Update new forward ptr. |
| | STG | R3, NEW.BWD | Update new backward ptr. |
| | TEND | | End transaction. |
| | ... | | |
| ABORTED | JO | NO_RETRY | CC3: Nonretryable abort. |
| | JCT | R15, LOOP | Retry transaction a few times. |
| | J | NO_RETRY | No joy after 10x; do it the hard way. |

\* R1 - address of the new queue element to be inserted.
\* R2 - address of the insertion point; new element is inserted before the element pointed to by R2.

In one example, if the transaction is used for lock elision, but the fallback path uses a lock, the transaction is to at least fetch the lock word to see that it is available. The processor ensures that the transaction aborts, if another CPU accesses the lock non-transactionally.

As used herein, storage, central storage, main storage, memory and main memory are used interchangeably, unless otherwise noted, implicitly by usage or explicitly. Further, while in one embodiment, a transaction effectively delaying includes delaying committing transactional stores to main memory until completion of a selected transaction; in another embodiment, the transaction effectively delaying includes allowing transactional updates to memory, but keeping the old values and restoring memory to the old values on an abort.

As will be appreciated by one skilled in the art, one or more aspects may be embodied as a system, method or computer program product. Accordingly, one or more aspects may take the form of an entirely hardware embodiment, an entirely software embodiment (including firmware, resident software, micro-code, etc.) or an embodiment combining software and hardware aspects that may all generally be referred to herein as a "circuit," "module" or "system". Furthermore, one or more aspects may take the form of a computer program product embodied in one or more computer readable medium(s) having computer readable program code embodied thereon.

Any combination of one or more computer readable medium(s) may be utilized. The computer readable medium may be a computer readable storage medium. A computer readable storage medium may be, for example, but not limited to, an electronic, magnetic, optical, electromagnetic, infrared or semiconductor system, apparatus, or device, or any suitable combination of the foregoing. More specific examples (a non-exhaustive list) of the computer readable storage medium include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

Figure 17:
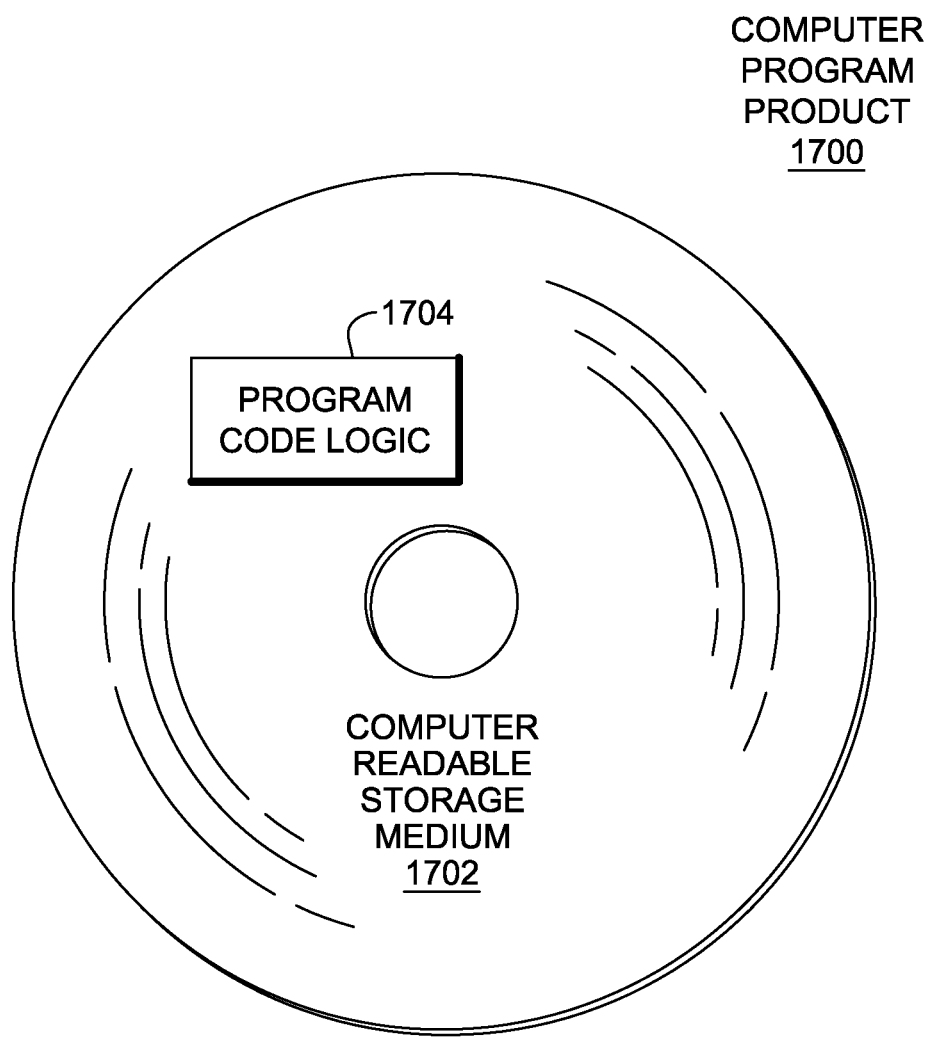
FIG. 17 depicts one embodiment of a computer program product.

Referring now to FIG. 17, in one example, a computer program product 1700 includes, for instance, one or more non-transitory computer readable storage media 1702 to store computer readable program code means or logic 1704 thereon to provide and facilitate one or more aspects.

Program code embodied on a computer readable medium may be transmitted using an appropriate medium, including but not limited to wireless, wireline, optical fiber cable, RF, etc., or any suitable combination of the foregoing.

Computer program code for carrying out operations for one or more aspects may be written in any combination of one or more programming languages, including an object oriented programming language, such as Java, Smalltalk, C++ or the like, and conventional procedural programming languages, such as the "C" programming language, assembler or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

One or more aspects are described herein with reference to flowchart illustrations and/or block diagrams of methods, apparatus (systems) and computer program products. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In addition to the above, one or more aspects may be provided, offered, deployed, managed, serviced, etc. by a service provider who offers management of customer environments. For instance, the service provider can create, maintain, support, etc. computer code and/or a computer infrastructure that performs one or more aspects for one or more customers. In return, the service provider may receive payment from the customer under a subscription and/or fee agreement, as examples. Additionally or alternatively, the service provider may receive payment from the sale of advertising content to one or more third parties.

In one aspect, an application may be deployed for performing one or more embodiment. As one example, the deploying of an application comprises providing computer infrastructure operable to perform one or more embodiments.

As a further aspect, a computing infrastructure may be deployed comprising integrating computer readable code into a computing system, in which the code in combination with the computing system is capable of performing one or more embodiments.

As yet a further aspect, a process for integrating computing infrastructure comprising integrating computer readable code into a computer system may be provided. The computer system comprises a computer readable medium, in which the computer medium comprises one or more embodiments. The code in combination with the computer system is capable of performing one or more embodiments.

Although various embodiments are described above, these are only examples. For example, computing environments of other architectures can be used incorporate and use one or more embodiments. Further, different instructions, instruction formats, instruction fields and/or instruction values may be used. Moreover, different, other, and/or additional diagnostic information and/or types of transaction diagnostic blocks may be provided/used. Many variations are possible.

Further, other types of computing environments can benefit and be used. As an example, a data processing system suitable for storing and/or executing program code is usable that includes at least two processors coupled directly or indirectly to memory elements through a system bus. The memory elements include, for instance, local memory employed during actual execution of the program code, bulk storage, and cache memory which provide temporary storage of at least some program code in order to reduce the number of times code must be retrieved from bulk storage during execution.

Input/Output or I/O devices (including, but not limited to, keyboards, displays, pointing devices, DASD, tape, CDs, DVDs, thumb drives and other memory media, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems, and Ethernet cards are just a few of the available types of network adapters.

Figure 18:
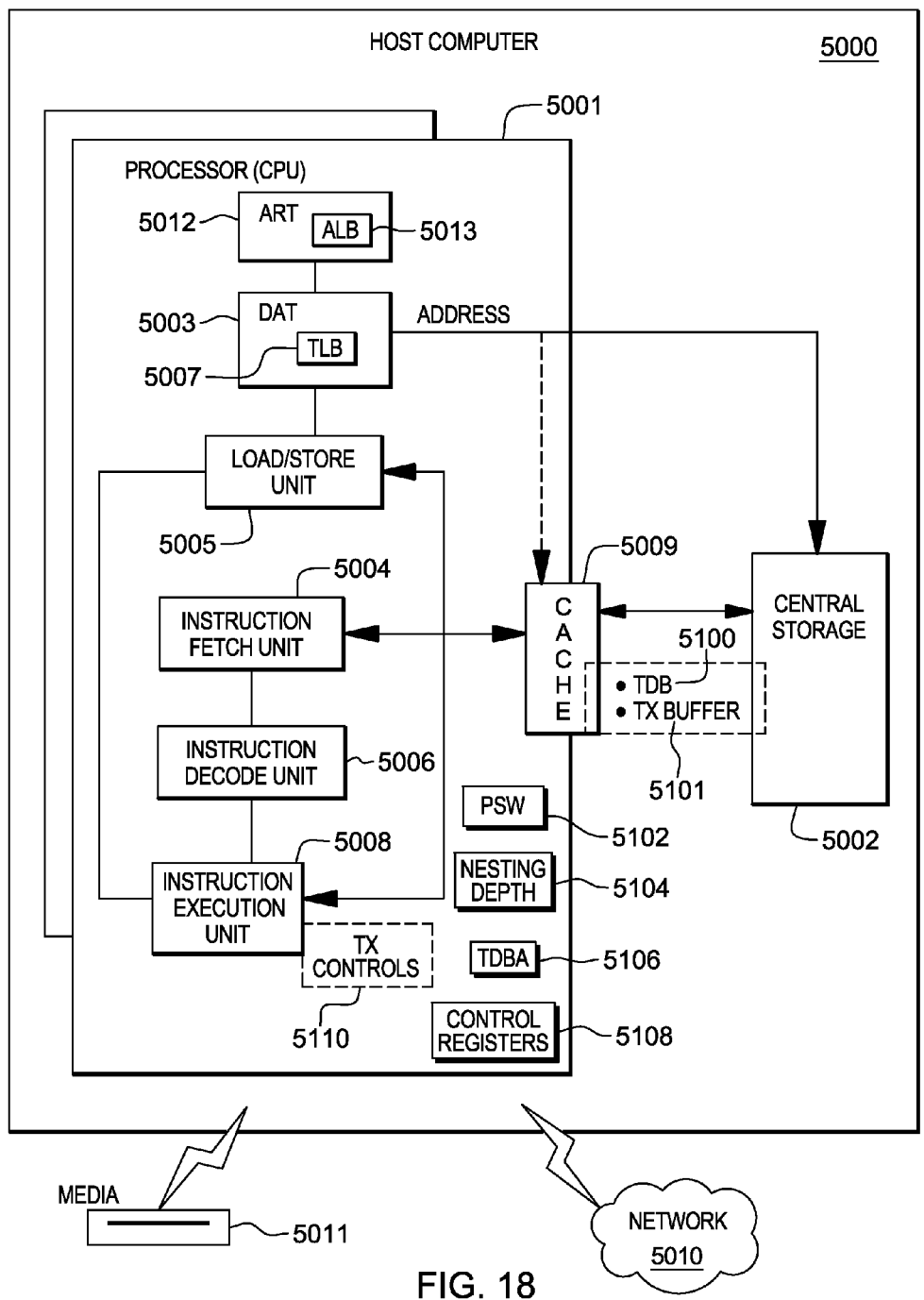
FIG. 18 depicts one embodiment of a host computer system.

Referring to FIG. 18, representative components of a Host Computer system 5000 to implement one or more embodiments are portrayed. The representative host computer 5000 comprises one or more CPUs 5001 in communication with computer memory (i.e., central storage) 5002, as well as I/O interfaces to storage media devices 5011 and networks 5010 for communicating with other computers or SANs and the like. The CPU 5001 is compliant with an architecture having an architected instruction set and architected functionality. The CPU 5001 may have access register translation (ART) 5012, which includes an ART lookaside buffer (ALB) 5013, for selecting an address space to be used by dynamic address translation (DAT) 5003 for transforming program addresses (virtual addresses) into real addresses of memory. A DAT typically includes a translation lookaside buffer (TLB) 5007 for caching translations so that later accesses to the block of computer memory 5002 do not require the delay of address translation. Typically, a cache 5009 is employed between computer memory 5002 and the processor 5001. The cache 5009 may be hierarchical having a large cache available to more than one CPU and smaller, faster (lower level) caches between the large cache and each CPU. In some implementations, the lower level caches are split to provide separate low level caches for instruction fetching and data accesses. In one embodiment, for the TX facility, a transaction diagnostic block (TDB) 5100 and one or more buffers 5101 may be stored in one or more of cache 5009 and memory 5002. In one example, in TX mode, data is initially stored in a TX buffer, and when TX mode ends (e.g., outermost TEND), the data in the buffer is stored (committed) to memory, or if there is an abort, the data in the buffer is discarded.

In one embodiment, an instruction is fetched from memory 5002 by an instruction fetch unit 5004 via a cache 5009. The instruction is decoded in an instruction decode unit 5006 and dispatched (with other instructions in some embodiments) to instruction execution unit or units 5008. Typically several execution units 5008 are employed, for example an arithmetic execution unit, a floating point execution unit and a branch instruction execution unit. Further, in one embodiment of the TX facility, various TX controls 5110 may be employed. The instruction is executed by the execution unit, accessing operands from instruction specified registers or memory as needed. If an operand is to be accessed (loaded or stored) from memory 5002, a load/store unit 5005 typically handles the access under control of the instruction being executed. Instructions may be executed in hardware circuits or in internal microcode (firmware) or by a combination of both.

In accordance with an aspect of the TX facility, processor 5001 also includes a PSW 5102 (e.g., TX and/or abort PSW), a nesting depth 5104, a TDBA 5106, and one or more control registers 5108.

As noted, a computer system includes information in local (or main) storage, as well as addressing, protection, and reference and change recording. Some aspects of addressing include the format of addresses, the concept of address spaces, the various types of addresses, and the manner in which one type of address is translated to another type of address. Some of main storage includes permanently assigned storage locations. Main storage provides the system with directly addressable fast-access storage of data. Both data and programs are to be loaded into main storage (from input devices) before they can be processed.

Main storage may include one or more smaller, faster-access buffer storages, sometimes called caches. A cache is typically physically associated with a CPU or an I/O processor. The effects, except on performance, of the physical construction and use of distinct storage media are generally not observable by the program.

Separate caches may be maintained for instructions and for data operands. Information within a cache is maintained in contiguous bytes on an integral boundary called a cache block or cache line (or line, for short). A model may provide an EXTRACT CACHE ATTRIBUTE instruction which returns the size of a cache line in bytes. A model may also provide PREFETCH DATA and PREFETCH DATA RELATIVE LONG instructions which effects the prefetching of storage into the data or instruction cache or the releasing of data from the cache.

Storage is viewed as a long horizontal string of bits. For most operations, accesses to storage proceed in a left-to-right sequence. The string of bits is subdivided into units of eight bits. An eight-bit unit is called a byte, which is the basic building block of all information formats. Each byte location in storage is identified by a unique nonnegative integer, which is the address of that byte location or, simply, the byte address. Adjacent byte locations have consecutive addresses, starting with 0 on the left and proceeding in a left-to-right sequence. Addresses are unsigned binary integers and are 24, 31, or 64 bits.

Information is transmitted between storage and a CPU or a channel subsystem one byte, or a group of bytes, at a time. Unless otherwise specified, in, for instance, the z/Architecture, a group of bytes in storage is addressed by the leftmost byte of the group. The number of bytes in the group is either implied or explicitly specified by the operation to be performed. When used in a CPU operation, a group of bytes is called a field. Within each group of bytes, in, for instance, the z/Architecture, bits are numbered in a left-to-right sequence. In the z/Architecture, the leftmost bits are sometimes referred to as the "high-order" bits and the rightmost bits as the "low-order" bits. Bit numbers are not storage addresses, however. Only bytes can be addressed. To operate on individual bits of a byte in storage, the entire byte is accessed. The bits in a byte are numbered 0 through 7, from left to right (in, e.g., the z/Architecture). The bits in an address may be numbered 8-31 or 40-63 for 24-bit addresses, or 1-31 or 33-63 for 31-bit addresses; they are numbered 0-63 for 64-bit addresses. In one example, bits 8-31 and 1-31 apply to addresses that are in a location (e.g., register) that is 32 bits wide, whereas bits 40-63 and 33-63 apply to addresses that are in a 64-bit wide location. Within any other fixed-length format of multiple bytes, the bits making up the format are consecutively numbered starting from 0. For purposes of error detection, and in preferably for correction, one or more check bits may be transmitted with each byte or with a group of bytes. Such check bits are generated automatically by the machine and cannot be directly controlled by the program. Storage capacities are expressed in number of bytes. When the length of a storage-operand field is implied by the operation code of an instruction, the field is said to have a fixed length, which can be one, two, four, eight, or sixteen bytes. Larger fields may be implied for some instructions. When the length of a storage-operand field is not implied but is stated explicitly, the field is said to have a variable length. Variable-length operands can vary in length by increments of one byte (or with some instructions, in multiples of two bytes or other multiples). When information is placed in storage, the contents of only those byte locations are replaced that are included in the designated field, even though the width of the physical path to storage may be greater than the length of the field being stored.

Certain units of information are to be on an integral boundary in storage. A boundary is called integral for a unit of information when its storage address is a multiple of the length of the unit in bytes. Special names are given to fields of 2, 4, 8, 16, and 32 bytes on an integral boundary. A halfword is a group of two consecutive bytes on a two-byte boundary and is the basic building block of instructions. A word is a group of four consecutive bytes on a four-byte boundary. A doubleword is a group of eight consecutive bytes on an eight-byte boundary. A quadword is a group of 16 consecutive bytes on a 16-byte boundary. An octoword is a group of 32 consecutive bytes on a 32-byte boundary. When storage addresses designate halfwords, words, doublewords, quadwords, and octowords, the binary representation of the address contains one, two, three, four, or five rightmost zero bits, respectively. Instructions are to be on two-byte integral boundaries. The storage operands of most instructions do not have boundary-alignment requirements.

On devices that implement separate caches for instructions and data operands, a significant delay may be experienced if the program stores into a cache line from which instructions are subsequently fetched, regardless of whether the store alters the instructions that are subsequently fetched.

In one example, embodiments may be practiced by software (sometimes referred to licensed internal code, firmware, micro-code, milli-code, pico-code and the like, any of which would be consistent with one or more embodiments). Referring to FIG. 18, software program code which embodies one or more aspects may be accessed by processor 5001 of the host system 5000 from long-term storage media devices 5011, such as a CD-ROM drive, tape drive or hard drive. The software program code may be embodied on any of a variety of known media for use with a data processing system, such as a diskette, hard drive, or CD-ROM. The code may be distributed on such media, or may be distributed to users from computer memory 5002 or storage of one computer system over a network 5010 to other computer systems for use by users of such other systems.

The software program code includes an operating system which controls the function and interaction of the various computer components and one or more application programs. Program code is normally paged from storage media device 5011 to the relatively higher-speed computer storage 5002 where it is available for processing by processor 5001. The techniques and methods for embodying software program code in memory, on physical media, and/or distributing software code via networks are well known and will not be further discussed herein. Program code, when created and stored on a tangible medium (including but not limited to electronic memory modules (RAM), flash memory, Compact Discs (CDs), DVDs, Magnetic Tape and the like is often referred to as a "computer program product". The computer program product medium is typically readable by a processing circuit preferably in a computer system for execution by the processing circuit.

Figure 19:
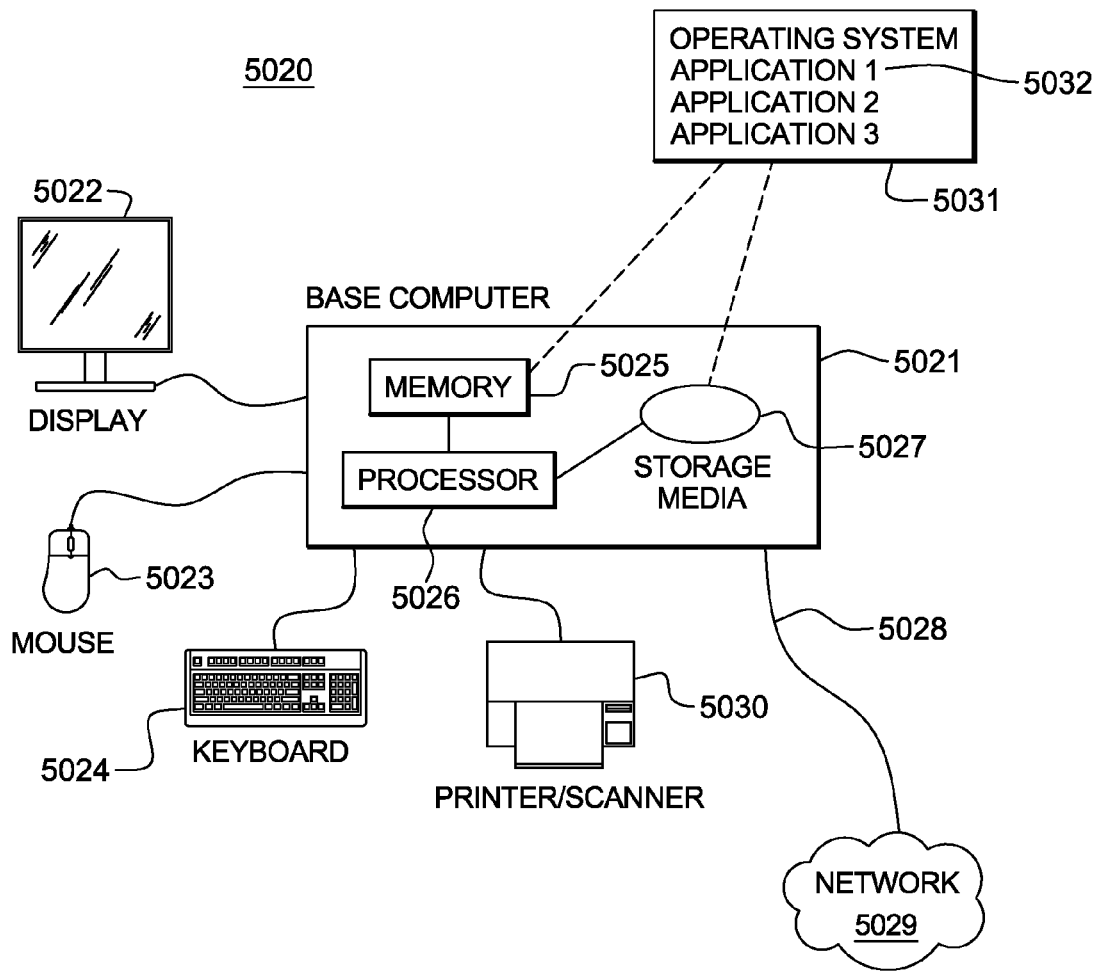
FIG. 19 depicts a further example of a computer system.

FIG. 19 illustrates a representative workstation or server hardware system in which one or more embodiments may be practiced. The system 5020 of FIG. 19 comprises a representative base computer system 5021, such as a personal computer, a workstation or a server, including optional peripheral devices. The base computer system 5021 includes one or more processors 5026 and a bus employed to connect and enable communication between the processor(s) 5026 and the other components of the system 5021 in accordance with known techniques. The bus connects the processor 5026 to memory 5025 and long-term storage 5027 which can include a hard drive (including any of magnetic media, CD, DVD and Flash Memory for example) or a tape drive for example. The system 5021 might also include a user interface adapter, which connects the microprocessor 5026 via the bus to one or more interface devices, such as a keyboard 5024, a mouse 5023, a printer/scanner 5030 and/or other interface devices, which can be any user interface device, such as a touch sensitive screen, digitized entry pad, etc. The bus also connects a display device 5022, such as an LCD screen or monitor, to the microprocessor 5026 via a display adapter.

The system 5021 may communicate with other computers or networks of computers by way of a network adapter capable of communicating 5028 with a network 5029. Example network adapters are communications channels, token ring, Ethernet or modems. Alternatively, the system 5021 may communicate using a wireless interface, such as a CDPD (cellular digital packet data) card. The system 5021 may be associated with such other computers in a Local Area Network (LAN) or a Wide Area Network (WAN), or the system 5021 can be a client in a client/server arrangement with another computer, etc. All of these configurations, as well as the appropriate communications hardware and software, are known in the art.

Figure 20:
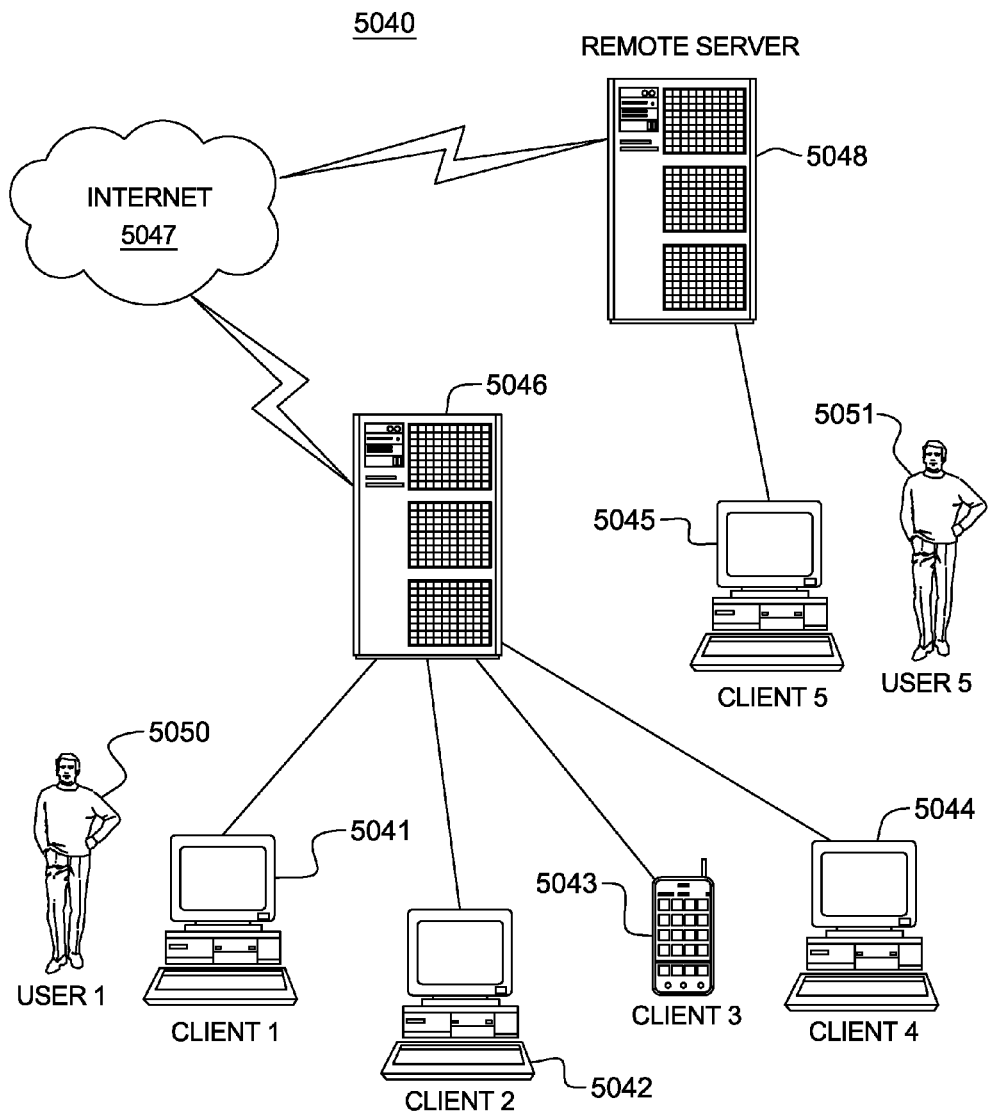
FIG. 20 depicts another example of a computer system comprising a computer network.

FIG. 20 illustrates a data processing network 5040 in which one or more embodiments may be practiced. The data processing network 5040 may include a plurality of individual networks, such as a wireless network and a wired network, each of which may include a plurality of individual workstations 5041, 5042, 5043, 5044. Additionally, as those skilled in the art will appreciate, one or more LANs may be included, where a LAN may comprise a plurality of intelligent workstations coupled to a host processor.

Still referring to FIG. 20, the networks may also include mainframe computers or servers, such as a gateway computer (client server 5046) or application server (remote server 5048 which may access a data repository and may also be accessed directly from a workstation 5045). A gateway computer 5046 serves as a point of entry into each individual network. A gateway is needed when connecting one networking protocol to another. The gateway 5046 may be preferably coupled to another network (the Internet 5047 for example) by means of a communications link. The gateway 5046 may also be directly coupled to one or more workstations 5041, 5042, 5043, 5044 using a communications link. The gateway computer may be implemented utilizing an IBM eServer System z server available from International Business Machines Corporation.

Referring concurrently to FIG. 19 and FIG. 20, software programming code 5031 which may embody one or more aspects may be accessed by the processor 5026 of the system 5020 from long-term storage media 5027, such as a CD-ROM drive or hard drive. The software programming code may be embodied on any of a variety of known media for use with a data processing system, such as a diskette, hard drive, or CD-ROM. The code may be distributed on such media, or may be distributed to users 5050, 5051 from the memory or storage of one computer system over a network to other computer systems for use by users of such other systems.

Alternatively, the programming code may be embodied in the memory 5025, and accessed by the processor 5026 using the processor bus. Such programming code includes an operating system which controls the function and interaction of the various computer components and one or more application programs 5032. Program code is normally paged from storage media 5027 to high-speed memory 5025 where it is available for processing by the processor 5026. The techniques and methods for embodying software programming code in memory, on physical media, and/or distributing software code via networks are well known and will not be further discussed herein. Program code, when created and stored on a tangible medium (including but not limited to electronic memory modules (RAM), flash memory, Compact Discs (CDs), DVDs, Magnetic Tape and the like is often referred to as a "computer program product". The computer program product medium is typically readable by a processing circuit preferably in a computer system for execution by the processing circuit.

The cache that is most readily available to the processor (normally faster and smaller than other caches of the processor) is the lowest (L1 or level one) cache and main store (main memory) is the highest level cache (L3 if there are 3 levels). The lowest level cache is often divided into an instruction cache (I-Cache) holding machine instructions to be executed and a data cache (D-Cache) holding data operands.

Figure 21:
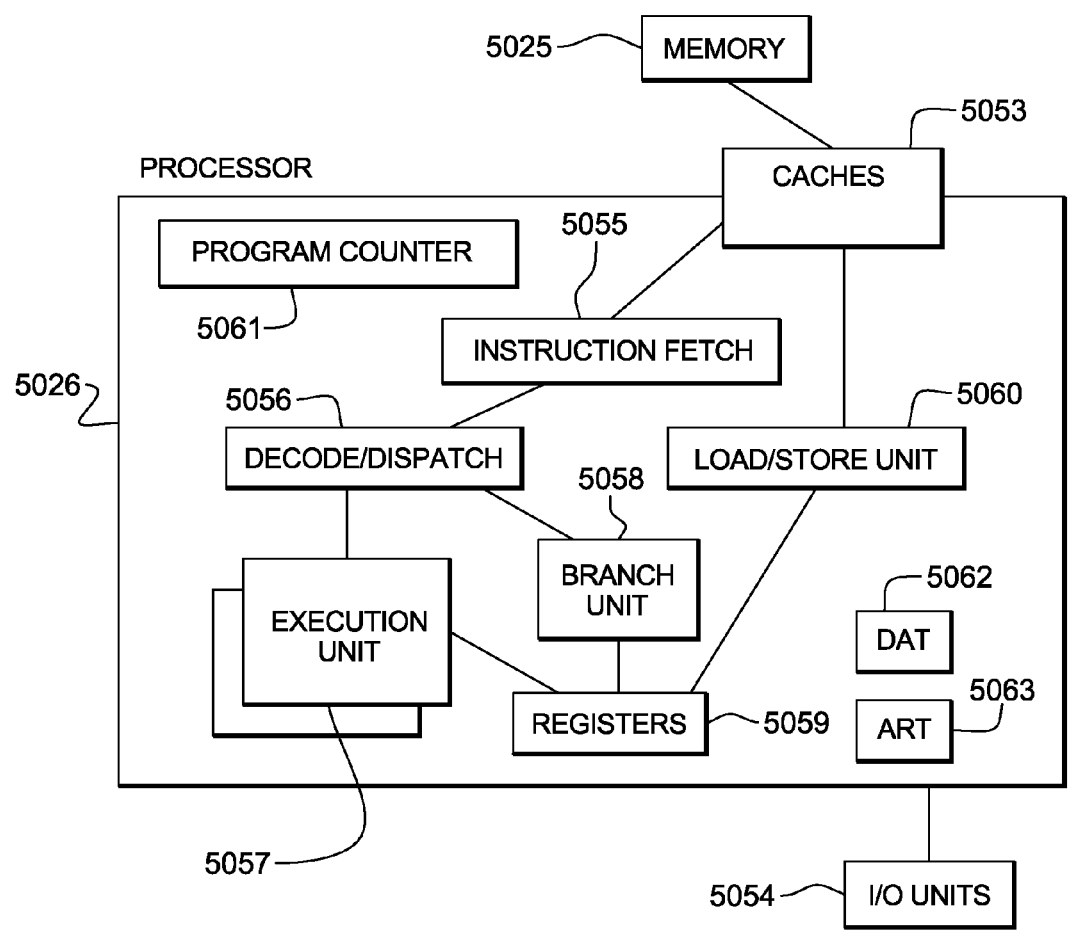
FIG. 21 depicts one embodiment of various elements of a computer system.

Referring to FIG. 21, an exemplary processor embodiment is depicted for processor 5026. Typically one or more levels of cache 5053 are employed to buffer memory blocks in order to improve processor performance. The cache 5053 is a high speed buffer holding cache lines of memory data that are likely to be used. Typical cache lines are 64, 128 or 256 bytes of memory data. Separate caches are often employed for caching instructions than for caching data. Cache coherence (synchronization of copies of lines in memory and the caches) is often provided by various "snoop" algorithms well known in the art. Main memory storage 5025 of a processor system is often referred to as a cache. In a processor system having 4 levels of cache 5053, main storage 5025 is sometimes referred to as the level 5 (L5) cache since it is typically faster and only holds a portion of the non-volatile storage (DASD, tape etc) that is available to a computer system. Main storage 5025 "caches" pages of data paged in and out of the main storage 5025 by the operating system.

A program counter (instruction counter) 5061 keeps track of the address of the current instruction to be executed. A program counter in a z/Architecture processor is 64 bits and can be truncated to 31 or 24 bits to support prior addressing limits. A program counter is typically embodied in a PSW (program status word) of a computer such that it persists during context switching. Thus, a program in progress, having a program counter value, may be interrupted by, for example, the operating system (context switch from the program environment to the operating system environment). The PSW of the program maintains the program counter value while the program is not active, and the program counter (in the PSW) of the operating system is used while the operating system is executing. Typically, the program counter is incremented by an amount equal to the number of bytes of the current instruction. RISC (Reduced Instruction Set Computing) instructions are typically fixed length while CISC (Complex Instruction Set Computing) instructions are typically variable length. Instructions of the IBM z/Architecture are CISC instructions having a length of 2, 4 or 6 bytes. The Program counter 5061 is modified by either a context switch operation or a branch taken operation of a branch instruction for example. In a context switch operation, the current program counter value is saved in the program status word along with other state information about the program being executed (such as condition codes), and a new program counter value is loaded pointing to an instruction of a new program module to be executed. A branch taken operation is performed in order to permit the program to make decisions or loop within the program by loading the result of the branch instruction into the program counter 5061.

Typically an instruction fetch unit 5055 is employed to fetch instructions on behalf of the processor 5026. The fetch unit either fetches "next sequential instructions", target instructions of branch taken instructions, or first instructions of a program following a context switch. Modern Instruction fetch units often employ prefetch techniques to speculatively prefetch instructions based on the likelihood that the prefetched instructions might be used. For example, a fetch unit may fetch 16 bytes of instruction that includes the next sequential instruction and additional bytes of further sequential instructions.

The fetched instructions are then executed by the processor 5026. In an embodiment, the fetched instruction(s) are passed to a dispatch unit 5056 of the fetch unit. The dispatch unit decodes the instruction(s) and forwards information about the decoded instruction(s) to appropriate units 5057, 5058, 5060. An execution unit 5057 will typically receive information about decoded arithmetic instructions from the instruction fetch unit 5055 and will perform arithmetic operations on operands according to the opcode of the instruction. Operands are provided to the execution unit 5057 preferably either from memory 5025, architected registers 5059 or from an immediate field of the instruction being executed. Results of the execution, when stored, are stored either in memory 5025, registers 5059 or in other machine hardware (such as control registers, PSW registers and the like).

Virtual addresses are transformed into real addresses using dynamic address translation 5062, and optionally, using access register translation 5063.

Figure 22A:
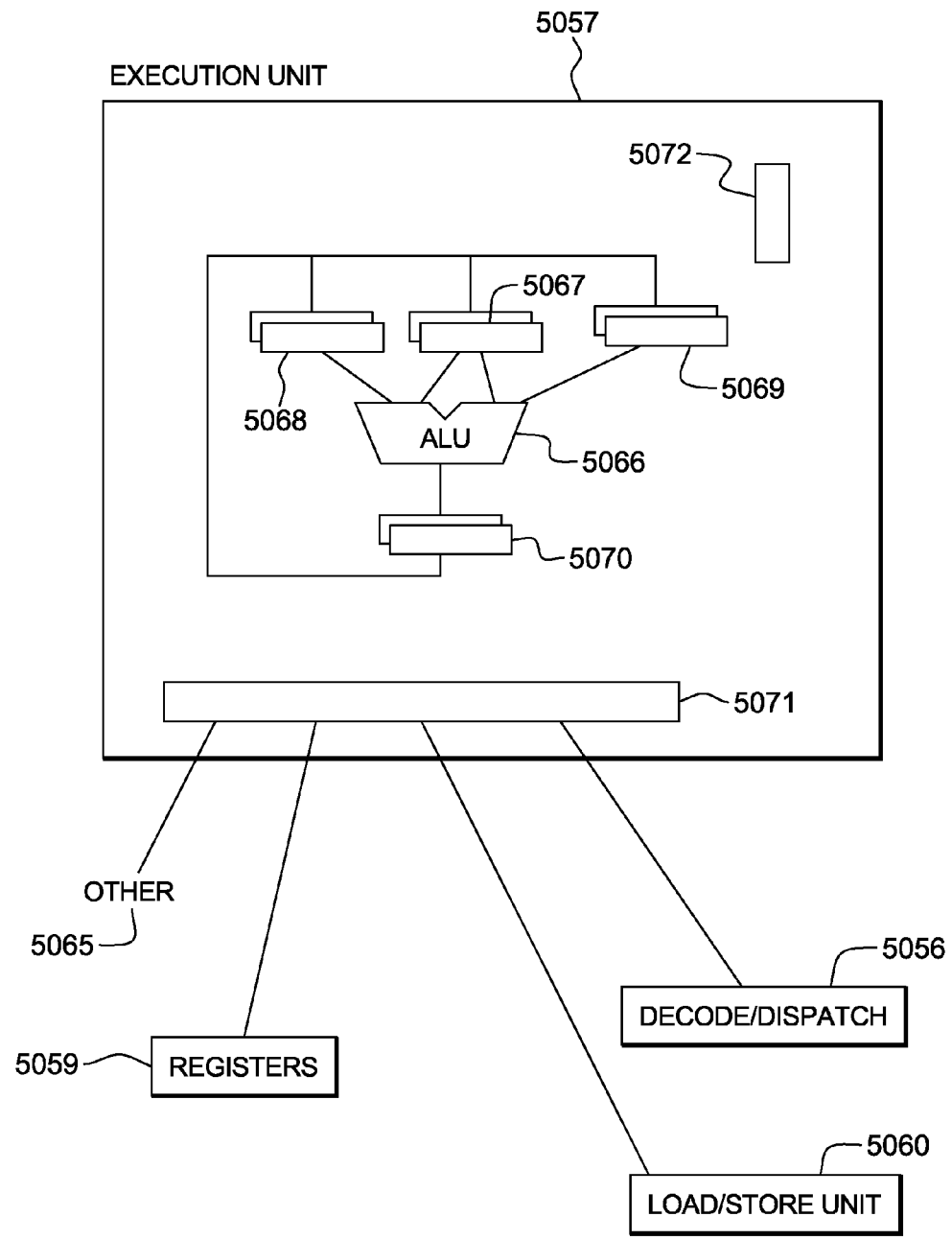
FIG. 22A depicts one embodiment of the execution unit of the computer system of FIG. 21.

A processor 5026 typically has one or more units 5057, 5058, 5060 for executing the function of the instruction. Referring to FIG. 22A, an execution unit 5057 may communicate with architected general registers 5059, a decode/dispatch unit 5056, a load store unit 5060, and other 5065 processor units by way of interfacing logic 5071. An execution unit 5057 may employ several register circuits 5067, 5068, 5069 to hold information that the arithmetic logic unit (ALU) 5066 will operate on. The ALU performs arithmetic operations such as add, subtract, multiply and divide as well as logical function such as and, or and exclusive-or (XOR), rotate and shift. Preferably the ALU supports specialized operations that are design dependent. Other circuits may provide other architected facilities 5072 including condition codes and recovery support logic for example. Typically the result of an ALU operation is held in an output register circuit 5070 which can forward the result to a variety of other processing functions. There are many arrangements of processor units, the present description is only intended to provide a representative understanding of one embodiment.

An ADD instruction for example would be executed in an execution unit 5057 having arithmetic and logical functionality while a floating point instruction for example would be executed in a floating point execution having specialized floating point capability. Preferably, an execution unit operates on operands identified by an instruction by performing an opcode defined function on the operands. For example, an ADD instruction may be executed by an execution unit 5057 on operands found in two registers 5059 identified by register fields of the instruction.

The execution unit 5057 performs the arithmetic addition on two operands and stores the result in a third operand where the third operand may be a third register or one of the two source registers. The execution unit preferably utilizes an Arithmetic Logic Unit (ALU) 5066 that is capable of performing a variety of logical functions such as Shift, Rotate, And, Or and XOR as well as a variety of algebraic functions including any of add, subtract, multiply, divide. Some ALUs 5066 are designed for scalar operations and some for floating point. Data may be Big Endian (where the least significant byte is at the highest byte address) or Little Endian (where the least significant byte is at the lowest byte address) depending on architecture. The IBM z/Architecture is Big Endian. Signed fields may be sign and magnitude, 1's complement or 2's complement depending on architecture. A 2's complement number is advantageous in that the ALU does not need to design a subtract capability since either a negative value or a positive value in 2's complement requires only an addition within the ALU. Numbers are commonly described in shorthand, where a 12 bit field defines an address of a 4,096 byte block and is commonly described as a 4 Kbyte (Kilo-byte) block, for example.

Figure 22B:
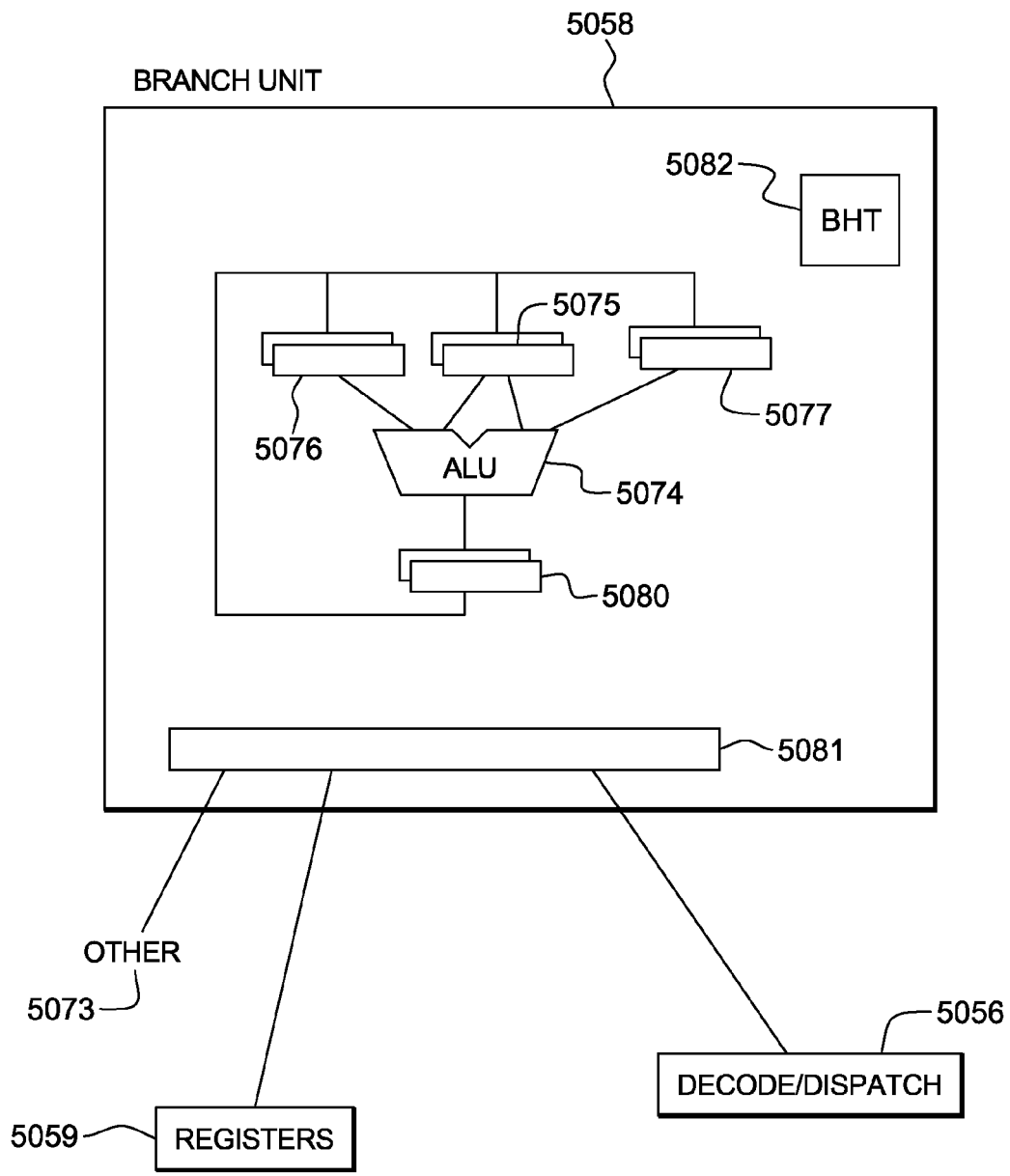
FIG. 22B depicts one embodiment of the branch unit of the computer system of FIG. 21.

Referring to FIG. 22B, branch instruction information for executing a branch instruction is typically sent to a branch unit 5058 which often employs a branch prediction algorithm such as a branch history table 5082 to predict the outcome of the branch before other conditional operations are complete. The target of the current branch instruction will be fetched and speculatively executed before the conditional operations are complete. When the conditional operations are completed the speculatively executed branch instructions are either completed or discarded based on the conditions of the conditional operation and the speculated outcome. A typical branch instruction may test condition codes and branch to a target address if the condition codes meet the branch requirement of the branch instruction, a target address may be calculated based on several numbers including ones found in register fields or an immediate field of the instruction for example. The branch unit 5058 may employ an ALU 5074 having a plurality of input register circuits 5075, 5076, 5077 and an output register circuit 5080. The branch unit 5058 may communicate 5081 with general registers 5059, decode dispatch unit 5056 or other circuits 5073, for example.

The execution of a group of instructions can be interrupted for a variety of reasons including a context switch initiated by an operating system, a program exception or error causing a context switch, an I/O interruption signal causing a context switch or multi-threading activity of a plurality of programs (in a multi-threaded environment), for example. Preferably a context switch action saves state information about a currently executing program and then loads state information about another program being invoked. State information may be saved in hardware registers or in memory for example. State information preferably comprises a program counter value pointing to a next instruction to be executed, condition codes, memory translation information and architected register content. A context switch activity can be exercised by hardware circuits, application programs, operating system programs or firmware code (microcode, pico-code or licensed internal code (LIC)) alone or in combination.

A processor accesses operands according to instruction defined methods. The instruction may provide an immediate operand using the value of a portion of the instruction, may provide one or more register fields explicitly pointing to either general purpose registers or special purpose registers (floating point registers for example). The instruction may utilize implied registers identified by an opcode field as operands. The instruction may utilize memory locations for operands. A memory location of an operand may be provided by a register, an immediate field, or a combination of registers and immediate field as exemplified by the z/Architecture long displacement facility wherein the instruction defines a base register, an index register and an immediate field (displacement field) that are added together to provide the address of the operand in memory for example. Location herein typically implies a location in main memory (main storage) unless otherwise indicated.

Figure 22C:
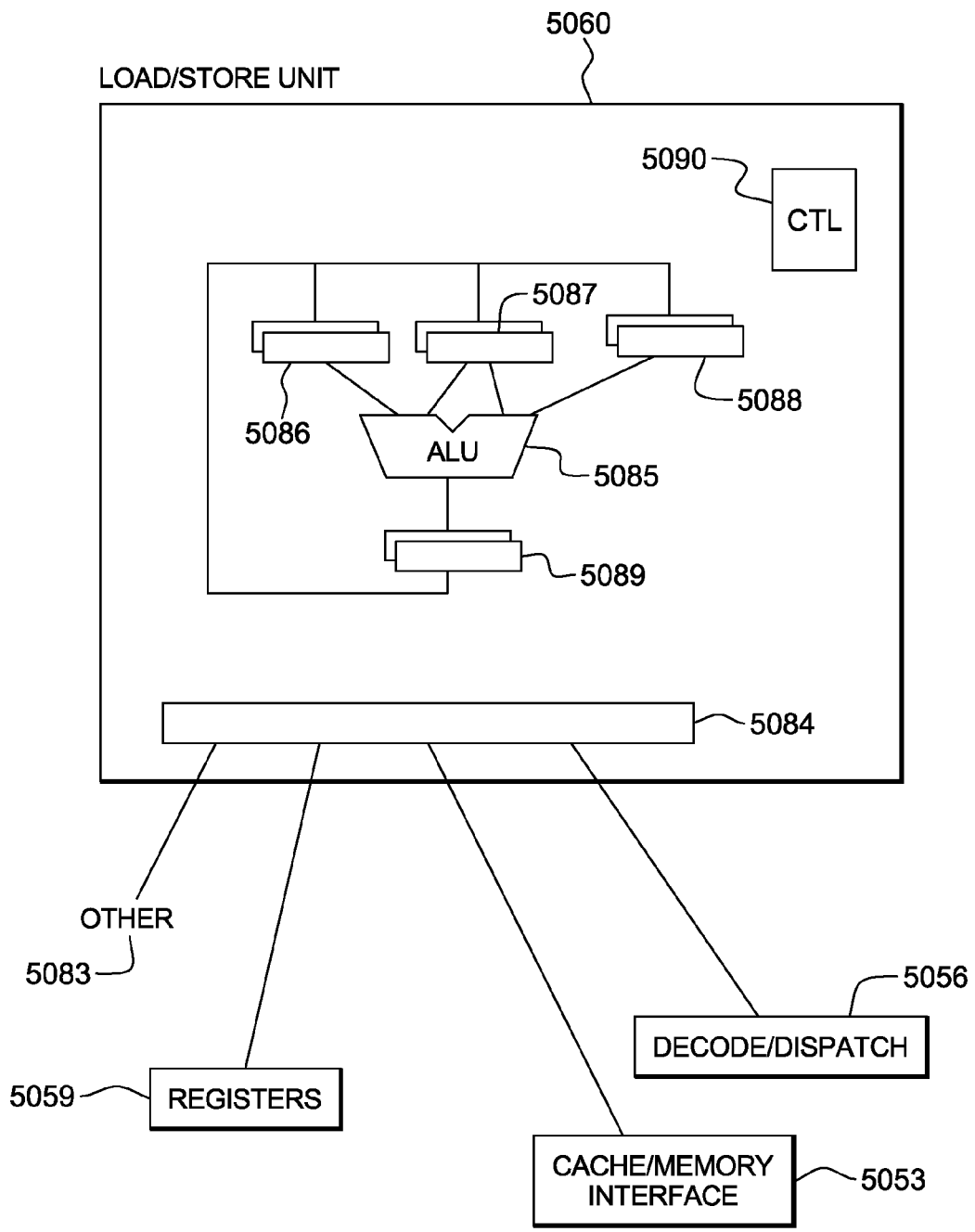
FIG. 22C depicts one embodiment of the load/store unit of the computer system of FIG. 21 n.

Referring to FIG. 22C, a processor accesses storage using a load/store unit 5060. The load/store unit 5060 may perform a load operation by obtaining the address of the target operand in memory 5053 and loading the operand in a register 5059 or another memory 5053 location, or may perform a store operation by obtaining the address of the target operand in memory 5053 and storing data obtained from a register 5059 or another memory 5053 location in the target operand location in memory 5053. The load/store unit 5060 may be speculative and may access memory in a sequence that is out-of-order relative to instruction sequence, however the load/store unit 5060 is to maintain the appearance to programs that instructions were executed in order. A load/store unit 5060 may communicate 5084 with general registers 5059, decode/dispatch unit 5056, cache/memory interface 5053 or other elements 5083 and comprises various register circuits 5086, 5087, 5088 and 5089, ALUs 5085 and control logic 5090 to calculate storage addresses and to provide pipeline sequencing to keep operations in-order. Some operations may be out of order but the load/store unit provides functionality to make the out of order operations to appear to the program as having been performed in order, as is well known in the art.

Preferably addresses that an application program "sees" are often referred to as virtual addresses. Virtual addresses are sometimes referred to as "logical addresses" and "effective addresses". These virtual addresses are virtual in that they are redirected to physical memory location by one of a variety of dynamic address translation (DAT) technologies including, but not limited to, simply prefixing a virtual address with an offset value, translating the virtual address via one or more translation tables, the translation tables preferably comprising at least a segment table a page table alone or in combination, preferably, the segment table having an entry pointing to the page table. In the z/Architecture, a hierarchy of translation is provided including a region first table, a region second table, a region third table, a segment table and an optional page table. The performance of the address translation is often improved by utilizing a translation lookaside buffer (TLB) which comprises entries mapping a virtual address to an associated physical memory location. The entries are created when the DAT translates a virtual address using the translation tables. Subsequent use of the virtual address can then utilize the entry of the fast TLB rather than the slow sequential translation table accesses. TLB content may be managed by a variety of replacement algorithms including LRU (Least Recently used).

In the case where the processor is a processor of a multi-processor system, each processor has responsibility to keep shared resources, such as I/O, caches, TLBs and memory, interlocked for coherency. Typically, "snoop" technologies will be utilized in maintaining cache coherency. In a snoop environment, each cache line may be marked as being in any one of a shared state, an exclusive state, a changed state, an invalid state and the like in order to facilitate sharing.

I/O units 5054 (FIG. 21) provide the processor with means for attaching to peripheral devices including tape, disc, printers, displays, and networks for example. I/O units are often presented to the computer program by software drivers. In mainframes, such as the System z from IBM®, channel adapters and open system adapters are I/O units of the mainframe that provide the communications between the operating system and peripheral devices.

Further, other types of computing environments can benefit from one or more aspects. As an example, an environment may include an emulator (e.g., software or other emulation mechanisms), in which a particular architecture (including, for instance, instruction execution, architected functions, such as address translation, and architected registers) or a subset thereof is emulated (e.g., on a native computer system having a processor and memory). In such an environment, one or more emulation functions of the emulator can implement one or more embodiments, even though a computer executing the emulator may have a different architecture than the capabilities being emulated. As one example, in emulation mode, the specific instruction or operation being emulated is decoded, and an appropriate emulation function is built to implement the individual instruction or operation.

In an emulation environment, a host computer includes, for instance, a memory to store instructions and data; an instruction fetch unit to fetch instructions from memory and to optionally, provide local buffering for the fetched instruction; an instruction decode unit to receive the fetched instructions and to determine the type of instructions that have been fetched; and an instruction execution unit to execute the instructions. Execution may include loading data into a register from memory; storing data back to memory from a register; or performing some type of arithmetic or logical operation, as determined by the decode unit. In one example, each unit is implemented in software. For instance, the operations being performed by the units are implemented as one or more subroutines within emulator software.

More particularly, in a mainframe, architected machine instructions are used by programmers, usually today "C" programmers, often by way of a compiler application. These instructions stored in the storage medium may be executed natively in a z/Architecture IBM® Server, or alternatively in machines executing other architectures. They can be emulated in the existing and in future IBM® mainframe servers and on other machines of IBM® (e.g., Power Systems servers and System x Servers). They can be executed in machines running Linux on a wide variety of machines using hardware manufactured by IBM®, Intel®, AMD, and others. Besides execution on that hardware under a z/Architecture, Linux can be used as well as machines which use emulation by Hercules, UMX, or FSI (Fundamental Software, Inc), where generally execution is in an emulation mode. In emulation mode, emulation software is executed by a native processor to emulate the architecture of an emulated processor.

The native processor typically executes emulation software comprising either firmware or a native operating system to perform emulation of the emulated processor. The emulation software is responsible for fetching and executing instructions of the emulated processor architecture. The emulation software maintains an emulated program counter to keep track of instruction boundaries. The emulation software may fetch one or more emulated machine instructions at a time and convert the one or more emulated machine instructions to a corresponding group of native machine instructions for execution by the native processor. These converted instructions may be cached such that a faster conversion can be accomplished. Notwithstanding, the emulation software is to maintain the architecture rules of the emulated processor architecture so as to assure operating systems and applications written for the emulated processor operate correctly. Furthermore, the emulation software is to provide resources identified by the emulated processor architecture including, but not limited to, control registers, general purpose registers, floating point registers, dynamic address translation function including segment tables and page tables for example, interrupt mechanisms, context switch mechanisms, Time of Day (TOD) clocks and architected interfaces to I/O subsystems such that an operating system or an application program designed to run on the emulated processor, can be run on the native processor having the emulation software.

A specific instruction being emulated is decoded, and a subroutine is called to perform the function of the individual instruction. An emulation software function emulating a function of an emulated processor is implemented, for example, in a "C" subroutine or driver, or some other method of providing a driver for the specific hardware as will be within the skill of those in the art after understanding the description of the preferred embodiment. Various software and hardware emulation patents including, but not limited to U.S. Pat. No. 5,551,013, entitled "Multiprocessor for Hardware Emulation", by Beausoleil et al.; and U.S. Pat. No. 6,009,261, entitled "Preprocessing of Stored Target Routines for Emulating Incompatible Instructions on a Target Processor", by Scalzi et al; and U.S. Pat. No. 5,574,873, entitled "Decoding Guest Instruction to Directly Access Emulation Routines that Emulate the Guest Instructions", by Davidian et al; and U.S. Pat. No. 6,308,255, entitled "Symmetrical Multiprocessing Bus and Chipset Used for Coprocessor Support Allowing Non-Native Code to Run in a System", by Gorishek et al; and U.S. Pat. No. 6,463,582, entitled "Dynamic Optimizing Object Code Translator for Architecture Emulation and Dynamic Optimizing Object Code Translation Method", by Lethin et al; and U.S. Pat. No. 5,790,825, entitled "Method for Emulating Guest Instructions on a Host Computer Through Dynamic Recompilation of Host Instructions", by Eric Traut, each of which is hereby incorporated herein by reference in its entirety; and many others, illustrate a variety of known ways to achieve emulation of an instruction format architected for a different machine for a target machine available to those skilled in the art.

Figure 23:
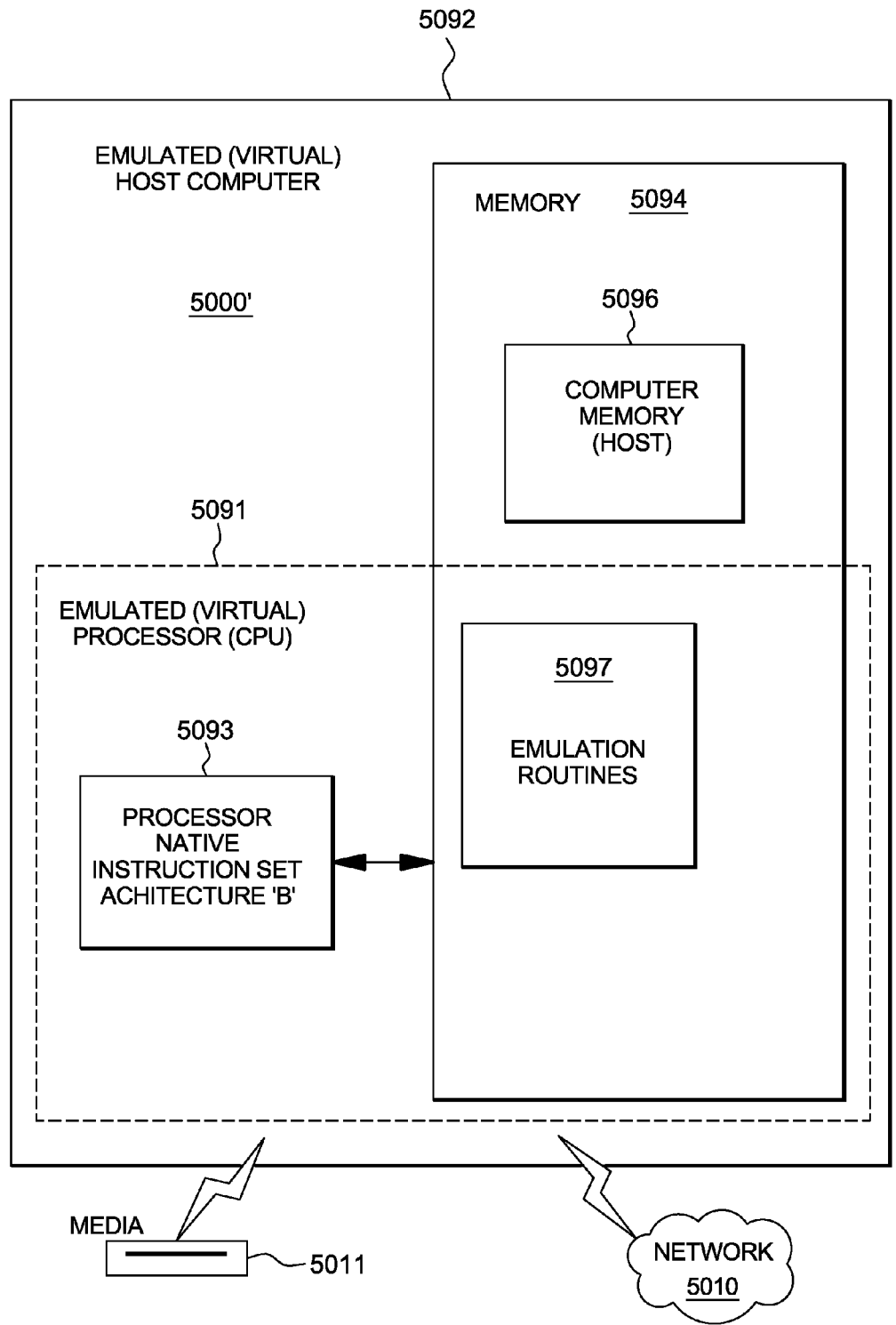
FIG. 23 depicts one embodiment of an emulated host computer system.

In FIG. 23, an example of an emulated host computer system 5092 is provided that emulates a host computer system 5000' of a host architecture. In the emulated host computer system 5092, the host processor (CPU) 5091 is an emulated host processor (or virtual host processor) and comprises an emulation processor 5093 having a different native instruction set architecture than that of the processor 5091 of the host computer 5000'. The emulated host computer system 5092 has memory 5094 accessible to the emulation processor 5093. In the example embodiment, the memory 5094 is partitioned into a host computer memory 5096 portion and an emulation routines 5097 portion. The host computer memory 5096 is available to programs of the emulated host computer 5092 according to host computer architecture. The emulation processor 5093 executes native instructions of an architected instruction set of an architecture other than that of the emulated processor 5091, the native instructions obtained from emulation routines memory 5097, and may access a host instruction for execution from a program in host computer memory 5096 by employing one or more instruction(s) obtained in a sequence & access/decode routine which may decode the host instruction(s) accessed to determine a native instruction execution routine for emulating the function of the host instruction accessed. Other facilities that are defined for the host computer system 5000' architecture may be emulated by architected facilities routines, including such facilities as general purpose registers, control registers, dynamic address translation and I/O subsystem support and processor cache, for example. The emulation routines may also take advantage of functions available in the emulation processor 5093 (such as general registers and dynamic translation of virtual addresses) to improve performance of the emulation routines. Special hardware and off-load engines may also be provided to assist the processor 5093 in emulating the function of the host computer 5000'.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components and/or groups thereof.

The corresponding structures, materials, acts, and equivalents of all means or step plus function elements in the claims below, if any, are intended to include any structure, material, or act for performing the function in combination with other claimed elements as specifically claimed. The description of one or more embodiments has been presented for purposes of illustration and description, but is not intended to be exhaustive or limited to the form disclosed. Many modifications and variations will be apparent to those of ordinary skill in the art. The embodiment was chosen and described in order to best explain various aspects and the practical application, and to enable others of ordinary skill in the art to understand the various embodiments with various modifications as are suited to the particular use contemplated.

What is claimed is:

1. A computer program product for providing diagnostic information on transaction aborts, the computer program product comprising:
   a non-transitory computer readable storage medium readable by a processing circuit and storing instructions for execution by the processing circuit for performing a method comprising:
      executing a transaction, the transaction effectively delaying committing transactional stores to main memory until completion of a selected transaction;
      based on executing the transaction, determining whether the transaction includes one or more branching instructions;
      based on determining the transaction includes one or more branching instructions, setting one or more indicators corresponding to the one or more branching instructions, wherein an indicator corresponds to a branching instruction and indicates whether a branch was taken by the branching instruction, wherein the setting of the indicator includes setting the indicator to a first value based on the branching instruction corresponding to the indicator taking a branch, and setting the indicator to a second value based on the branching instruction corresponding to the indicator not taking the branch;
      determining that the transaction has aborted; and
      based on determining the transaction has aborted, storing the one or more indicators in a transaction diagnostic block (TDB) associated with the transaction, wherein the transaction diagnostic block provides a branch history that indicates which branching instructions have taken the branch and which branching instructions have not taken the branch during a transactional execution mode that includes the transaction.

2. The computer program product of claim 1, wherein the method further comprises initiating the transaction via a transaction begin instruction, the transaction begin instruction specifying an address for the transaction diagnostic block.

3. The computer program product of claim 1, wherein the one or more indicators comprise one or more bits, the one or more bits being included within a vector of a plurality of bits, the plurality of bits, except for a selected bit, representing branching instructions executed within the transaction, the selected bit to indicate whether there are more branching instructions than bits in the vector.

4. The computer program product of claim 3, wherein the one or more indicators are bit significant and arranged in sequential order of the branch instructions of the transaction.

5. The computer program product of claim 1, wherein there are a plurality of types of transaction diagnostic blocks, and the method further comprises selecting one or more types of transaction diagnostic blocks to store the one or more indicators, the selecting being based on one or more of: a type of abort or information provided in initiating the transaction.

6. The computer program product of claim 5, wherein the plurality of types of transaction diagnostic blocks comprises a program-specified TDB, a program interruption TDB, and an interception TDB.

7. The computer program product of claim 6, wherein the transaction is initiated by a transaction begin instruction, and the selecting comprises determining whether a valid transaction block address is provided in the transaction begin instruction, wherein based on a valid transaction diagnostic block address being provided, the one or more indicators are stored in the program-specified TDB.

8. The computer program product of claim 1, wherein the method further comprises initiating the transaction via a transaction begin instruction, the transaction being a nonconstrained transaction.

9. The computer program product of claim 1, wherein the one or more indicators stored in the transaction diagnostic block provide a branch history of the transaction.

10. The computer program product of claim 1, wherein an address of the transaction diagnostic block is specified by an instruction initiating the transaction.

11. The computer program product of claim 1, wherein the indicator is a bit.

12. A computer system for providing diagnostic information on transaction aborts, the computer system comprising:
a memory; and
a processor in communications with the memory, wherein the computer system is configured to perform a method, said method comprising:
executing a transaction, the transaction effectively delaying committing transactional stores to main memory until completion of a selected transaction;
based on executing the transaction, determining whether the transaction includes one or more branching instructions;
based on determining the transaction includes one or more branching instructions, setting one or more indicators corresponding to the one or more branching instructions, wherein an indicator corresponds to a branching instruction and indicates whether a branch was taken by the branching instruction, wherein the setting of the indicator includes setting the indicator to a first value based on the branching instruction corresponding to the indicator taking a branch, and setting the indicator to a second value based on the branching instruction corresponding to the indicator not taking the branch;
determining that the transaction has aborted; and
based on determining the transaction has aborted, storing the one or more indicators in a transaction diagnostic block (TDB) associated with the transaction, wherein the transaction diagnostic block provides a branch history that indicates which branching instructions have taken the branch and which branching instructions have not taken the branch during a transactional execution mode that includes the transaction.

13. The computer system of claim 12, wherein the method further comprises initiating the transaction via a transaction begin instruction, the transaction being a nonconstrained transaction, and the transaction begin instruction specifying an address for the transaction diagnostic block.

14. The computer system of claim 12, wherein the one or more indicators comprise one or more bits, the one or more bits being included within a vector of a plurality of bits, the plurality of bits, except for a selected bit, representing branching instructions executed within the transaction, the selected bit to indicate whether there are more branching instructions than bits in the vector.

15. The computer system of claim 12, wherein there are a plurality of types of transaction diagnostic blocks, including a program-specified TDB, a program interruption TDB, and an interception TDB, and the method further comprises selecting one or more types of transaction diagnostic blocks to store the one or more indicators, the selecting being based on one or more of: a type of abort or information provided in initiating the transaction.

16. The computer system of claim 15, wherein the transaction is initiated by a transaction begin instruction, and the selecting comprises determining whether a valid transaction block address is provided in the transaction begin instruction, wherein based on a valid transaction diagnostic block address being provided, the one or more indicators are stored in the program-specified TDB.

17. The computer system of claim 12, wherein the one or more indicators stored in the transaction diagnostic block provide a branch history of the transaction.

18. The computer system of claim 12, wherein an address of the transaction diagnostic block is specified by an instruction initiating the transaction.

19. The computer system of claim 12, wherein the indicator is a bit.

* * * * *